(12) United States Patent
Levasseur et al.

(10) Patent No.: US 7,981,650 B2
(45) Date of Patent: Jul. 19, 2011

(54) FUSION PROTEINS BETWEEN PLANT CELL-WALL DEGRADING ENZYMES, AND THEIR USES

(75) Inventors: Anthony Levasseur, Aubagne (FR); David Navarro, Marseilles (FR); Peter Punt, Houten (NL); Jean-Pierre Belaïch, Marseilles (FR); Marcel Asther, La Ciotat (FR); Frédéric Monot, Nanterre (FR); Eric Record, Marseilles (FR)

(73) Assignees: Institut National de la Recherche Agronomique, Paris (FR); Institut Francais du Petrole, Rueil-Malmaison (FR)

( * ) Notice: Subject to any disclaimer, the term of this patent is extended or adjusted under 35 U.S.C. 154(b) by 0 days.

(21) Appl. No.: 11/990,339

(22) PCT Filed: Jul. 26, 2006

(86) PCT No.: PCT/EP2006/007370
§ 371 (c)(1),
(2), (4) Date: Jun. 5, 2008

(87) PCT Pub. No.: WO2007/019949
PCT Pub. Date: Feb. 22, 2007

(65) Prior Publication Data
US 2009/0181431 A1 Jul. 16, 2009

(30) Foreign Application Priority Data
Aug. 12, 2005 (EP) .................................... 05291721

(51) Int. Cl.
*C12N 9/00* (2006.01)
*C12N 9/14* (2006.01)
(52) U.S. Cl. ........ 435/183; 435/195; 435/197; 435/200; 435/203
(58) Field of Classification Search .................. None
See application file for complete search history.

(56) References Cited

FOREIGN PATENT DOCUMENTS

| WO | 01/66711 A1 | 9/2001 |
|---|---|---|
| WO | 2004/009804 A2 | 1/2004 |
| WO | 2004/111216 A2 | 12/2004 |
| WO | 2005/003319 A2 | 1/2005 |

OTHER PUBLICATIONS

Gielkens et al. "Two cellobiohydrolase-encoding genes from *Aspergillus niger* require . . . " Appl. Environm. Microbiol 1999, 65, 10, 4340-4345.*
An et al., "Evaluation of a novel bifunctional xylanase-cellulase constructed by gene fusion," Enzyme & Microbio. Tech., vol. 36. No. 7, pp. 989-995 (May 16, 2005).
Devries et al., "The *Aspergillus niger* faeB gene encodes a second feruloyl esterase involved in pectin and xylan degradation and is specifically induced in the presence of aromatic compounds," Biochem. J., vol. 363, No. 2, pp. 377-386 (Apr. 15, 2002).
Yu et al., "Release of Ferulic Acid from Oat Hulls by Aspergillus Ferulic Acid Esterase and Trichoderma Xylanase," J. of Agric. & Food Chem., vol. 50, No. 6, pp. 1625-1630 (Mar. 13, 2002).
Faulds et al., "Release of Ferulic Acid from Wheat Bran by a ferulic acid esterase (FAE-III) from *Aspergillus niger*," Appl. Microbio. Biotech., vol. 43, No. 6, pp. 1082-1087 (1995).
Bartolome et al., "An *Aspergillus niger* esterase (Ferulic Acid Esterase III) and a Recombinant Pseudomonas fluorescens subsp. Cellulosa Esterase (XylD) Release a 5-5' Ferulic Dehydrodimer (Diferulic Acid) from Barley and Wheat Cell Walls," App. & Env. Microbio., vol. 63, No. 1, pp. 208-212 (1997).
Levasseur et al., "Design and Production in *Aspergillus niger* of a Chimeric Protein Associating a Fungal Feruloyl Esterase and a Clostridial Dockerin Domain," App. & Env. Microbio., vol. 70, No. 12, pp. 6984-6991 (Dec. 12, 2004).
Nixon et al., "Hybrid enzymes: manipulating enzyme design," Trends in Biotech., vol. 16, No. 6, pp. 258-264 (Jun. 6, 1998).
Bhat et al., "Cellulose Degrading Enzymes and their potential Industrial Applications," Biotech. Adv., vol. 15, No. 3-4, pp. 583-620 (1997).
Levasseur et al., "Construction of Engineered Bifunctional Enzymes and their Overproduction in *Aspergillus niger* for Improved Enzymatic Tools to Degrade Agricultural By-Products," App. & Env. Microbio., vol. 71, No. 12, pp. 8132-8140 (Dec. 2005).

* cited by examiner

*Primary Examiner* — Nashaat Nashed
(74) *Attorney, Agent, or Firm* — Young & Thompson

(57) ABSTRACT

The invention relates to the use of fusion proteins between at least two plant cell-wall degrading enzymes, the enzymes being such that they do not contain a C-terminal carbohydrate-binding-molecule (CBM), and optionally a CBM, the enzymes and CBM being recombinant proteins corresponding to native proteins in fungi, or mutated forms thereof, for carrying out processes of plant cell-wall degradation in the frame of the preparation, from plants or vegetal by-products, of compounds of interest located in plant cell-wall, or in the frame of the bleaching of pulp and paper.

6 Claims, 5 Drawing Sheets

FUSION PROTEINS BETWEEN PLANT CELL-WALL DEGRADING ENZYMES, AND THEIR USES

Figure 1:
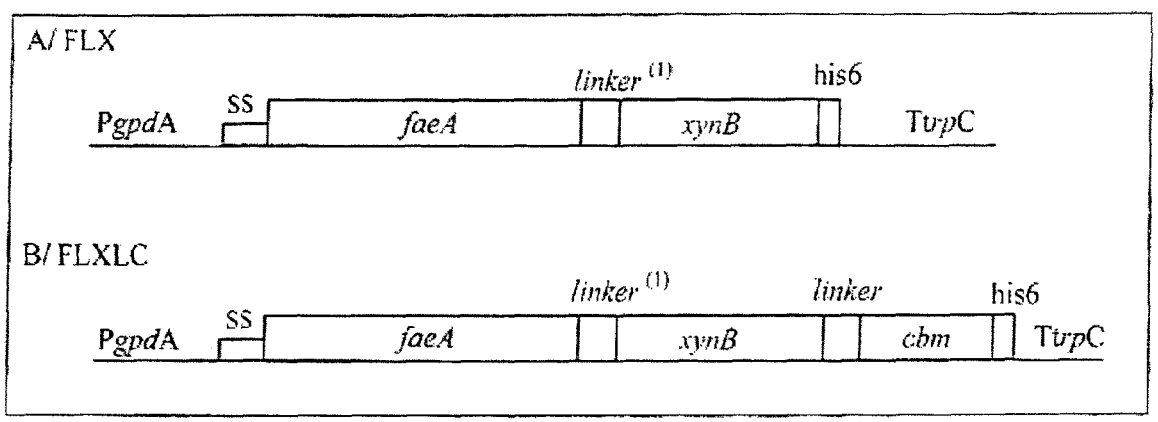

The invention relates to the construction and overproduction of engineered multifunctional plant cell-wall degrading enzymes, and to their uses as improved enzymatic tools for valorization of agricultural by-products.

Agricultural residues represent large renewable resources for lignocelluloses bioconversion. Daily, outputs of the food industry generate a lot of these by-products considered as polluting wastes to eliminate. A great deal of research has been expended on the valorization of these by-products in the biotechnology sector. Among valorizable components, ferulic acid (4-hydroxy-3-methoxy-cinnamic acid) is a very attractive phenolic compound found as the most abundant hydroxycinnamic acid in the plant world. For instance, ferulic acid can be used as an antioxidant (23) or be transformed by microbial conversion into "natural" vanillin as an expensive flavour in the food, cosmetic and pharmaceutical industries (4, 26). Among agricultural by-products, maize and wheat brans are potential substrates according to their high amounts of ferulic acid in the cell wall, i.e. 3% and 1% (w\w), respectively (43). In the plant physiology, ferulic acid is a key structural component with important physical and chemical properties of plant cell walls. Indeed, it may act as a cross-linking agent between lignin and carbohydrates or between carbohydrates themselves (16) influencing the cell wall integrity, and thus reducing biodegradability extent resulting from microbial enzymes (6).

Microorganisms evolved enzymes, such as feruloyl esterases (EC 3.1.1.73), able to hydrolyse ester bonds linking ferulic acid to plant cell wall polysaccharides. These enzymes allow a facilitated accessibility for other lignocellulolytic enzymes. to the polysaccharide backbone (for a review, see 12). Previous studies demonstrate that feruloyl esterases act in synergy with the main-chain-degrading enzymes such as β-(1,4)-endoxylanases to increase the release of ferulic acid from plant cell wall and for production of sufficient amount needed for applications (2,15,50). Filamentous fungi, such as *Aspergillus niger*, are a well-known producers of plant cell wall-degrading enzymes. Two different genes encoding feruloyl esterases from *A. niger* were already cloned (10,11) and their corresponding recombinant proteins overproduced in *Pichia pastoris* and *A. niger* (24,30,41). Several fungal feruloyl esterases were purified and characterized (18,47) but no gene was further cloned. Previous work reported the isolation from *Penicillium funiculosum* of the first fungal cinnamoyl esterase (type B) with a C-term domain closely similar to the family 1 Carbohydrate-Binding-Module (CBM) (27). Many glycosyl hydrolases from anaerobic and aerobic microorganisms have a modular structure. In addition to a catalytic domain, one or more non-catalytic CBM can be located either at the N- or the C-terminal, or both. CBM have been classified into families with similar amino acid sequences and 3D-structures. CBM have a major role on insoluble substrate degradation (45). For instance, they are responsible for the maintain of the catalytic core domain close to the substrate increasing longevity and intimacy of contact. Moreover, in some cases, CBM can also alter the cellulose microfibril structure by weakening the hydrogen bonds of the gathered cellulose chains (13,14,33).

The present invention involves considerations about the synergistic effect between free and fused plant cell wall-degrading enzymes of fungi, such as *A. niger*. In a recent study based on engineered bacterial cellulosome, physical proximity of two catalytic components allowed to observe enhanced synergy on recalcitrant substrates (17). On this basis, the inventors designed a chimeric protein associating a fungal feruloyl esterase and a clostridial dockerin domain to be grafted with a second enzyme onto a bacterial CBM-containing-scaffolding protein (31). However, production yield of the recombinant protein were not enough large for test applications at industrial scale and a new strategy was envisaged. In the present work, the inventors fused two fungal enzymes: the feruloyl esterase A (FAEA) and the xylanase B (XYNB) from *A. niger* separated by a hyperglycosylated linker peptide to obtain a bifunctional enzyme (FLX) with increased efficiency for the ferulic acid release. Moreover, the inventors also added in a second construction, a fungal CBM from *A. niger* cellobiohydrolase B (CBHB) at the C-term end of this bifunctional enzyme (FLXLC). Both hybrid enzymes were successfully produced in *A. niger* and fully characterized considering biochemical and kinetics aspects and finally used to release ferulic acid from natural substrates: maize and wheat brans. The objective of this work was to compare the ferulic acid release efficiency by using free or fused enzymes in order to study enzymatic synergy generated by the physical proximity of fungal enzymes. Moreover, effect of the CBM addition at the C-terminus of the bifunctional enzyme was investigated in the FLXLC construction.

The present invention relies on the demonstration of the synergistic effect of the fusion in a single chimeric protein of plant cell-wall degrading enzymes, said enzymes being such that they do not contain a CBM, when compared to the use of the free plant cell-wall degrading enzymes.

Thus the main goal of the present invention is to provide new fusion proteins between plant CBM-free cell-wall degrading enzymes.

Another goal of the present invention is to provide a new process for the preparation of compounds of interest linked to the walls of plant cells, by applying said fusion proteins to plants, and advantageously to agricultural by-products, as substrates.

The present invention relates to the use of fusion proteins between at least two plant cell-wall degrading enzymes, said enzymes being such that they do not contain a C-terminal carbohydrate-binding-molecule (CBM), and optionally a CBM, said enzymes and CBM being recombinant proteins corresponding to native proteins in fungi, or mutated forms thereof, for carrying out processes of plant cell-wall degradation in the frame of the preparation, from plants or vegetal by-products, of compounds of interest located in plant cell-wall, or in the frame of the bleaching of pulp and paper.

The expression "plant cell-wall degrading enzymes" refers to enzymes that are able to perform the digestion of the cell-wall components, such as cellulose, hemicellulose and lignin. The plant cell-wall degrading enzymes in said fusion proteins are identical, or different from each other.

The expression "C-terminal carbohydrate-binding-molecule" refers to a molecule with affinity to cellulose that targets its associated enzyme to the cellulose.

The invention more particularly relates to the use as defined above, wherein the plant cell-wall degrading enzymes which do not contain a CBM are hydrolases chosen among:
- cellulases, such as cellobiohydrolases, endoglucanases, and exoglucanases, or β-glucosidases,
- hemicellulases, such as xylanases,
-ligninases able to degrade lignins, such as laccases, manganese peroxidase, lignin peroxidase, versatile peroxidase, or accessory enzymes such as cellobiose deshydrogenases, and aryl alcohol oxidases, cinnamoyl ester hydrolases able to release cinnamic acids such as ferulic acid and to hydrolyse diferulic acid cross-links between hemicellulose chains, such as feruloyl esterases, cinnamoyl esterases, and chlorogenic acid hydrolases.

The invention more particularly concerns the use as defined above, wherein the plant cell-wall degrading enzymes which do not contain a CBM are chosen among feruloyl esterases and xylanases.

The invention more particularly relates to the use as defined above, wherein the plant cell-wall degrading enzymes which do not contain a CBM correspond to native enzymes, or mutated forms thereof, from fungi chosen among:
- ascomycetes, such as *Aspergillus* strains, and more particularly *Aspergillus niger*,
- basidiomycetes, such as *Pycnoporus* or *Halociphina* strains, and more particularly *Pycnoporus cinnabarinus, Pycnoporus sanguineus*, or *Halocyphina villosa*.

The invention more particularly concerns the use as defined above, wherein the plant cell-wall degrading enzymes which do not contain a CBM correspond to native enzymes, or mutated forms thereof, from *Aspergillus* strains, such as *Aspergillus niger*.

The invention more particularly relates to the use as defined above, wherein at least one of the plant cell-wall degrading enzymes is a feruloyl esterase chosen among:
- the feruloyl esterase A of *A. niger* represented by SEQ ID NO : 2, encoded by the nucleic acid represented by SEQ ID NO : 1,
- or the feruloyl esterase B of *A. niger* represented by SEQ ID NO : 4, encoded by the nucleic acid represented by SEQ ID NO : 3.

The invention more particularly concerns the use as defined above, wherein at least one of the plant cell-wall degrading enzymes is a xylanase as defined above such as the xylanase B of *A. niger* represented by SEQ ID NO : 6, encoded by the nucleic acid represented by SEQ ID No : 5.

The invention more particularly relates to the use as defined above, wherein the protein being a CBM is chosen among CBM present in native enzymes, or mutated forms thereof, from fungi chosen among ascomycetes, such as *Aspergillus* strains, and more particularly *Aspergillus niger*.

CBM which may be used according to the present invention are those of the family 1.

The invention more particularly relates to the use as defined above, wherein the CBM is the CBM present in the cellobiohydrolase B of *A. niger*, and represented by SEQ ID NO : 8, encoded by the nucleic acid represented by SEQ ID NO : 7.

The invention also concerns the use as defined above, of fusion proteins comprising linkers between at least two of the proteins comprised in said fusion proteins, said linkers being polypeptides from 10 to 100 aminoacids, advantageously of about 50 aminoacids.

The invention more particularly concerns the use as defined above, of fusion proteins wherein a linker is included between each protein comprised in said fusion proteins.

The invention more particularly relates to the use as defined above, wherein the linker is a hyperglycosylated polypeptide such as the sequence represented by SEQ ID NO : 10, present in the cellobiohydrolase B of *A. niger*, and encoded by the nucleic acid represented by SEQ ID NO : 9.

The invention also more particularly relates to the use as defined above, of fusion proteins between a feruloyl esterase and a xylanase, and optionally a CBM.

The invention more particularly concerns the use as defined above, of fusion proteins between the feruloyl esterase A of *A. niger* represented by SEQ ID NO : 2, or the feruloyl esterase B of *A. niger* represented by SEQ ID NO : 4, and the xylanase B of *A. niger* represented by SEQ ID NO : 6.

The invention more particularly relates to the use as defined above, of the fusion protein between the feruloyl esterase A of *A. niger* represented by SEQ ID NO : 2, and the xylanase B of *A. niger* represented by SEQ ID NO : 6, said fusion protein comprising the sequence represented by SEQ ID NO : 10 as a hyperglycosylated linker between the two preceding proteins, and being represented by SEQ ID NO : 12.

The invention also relates to the use as defined above, of fusion proteins between the feruloyl esterase A of *A. niger* represented by SEQ ID NO : 2, the xylanase B of *A. niger* represented by SEQ ID NO : 6, and the CBM represented by SEQ ID NO : 8 present in the cellobiohydrolase B of *A. niger*.

The invention more particularly concerns the use as defined above, of the fusion protein between the feruloyl esterase A of *A. niger* represented by SEQ ID NO : 2, the xylanase B of *A. niger* represented by SEQ ID NO : 6, and the CBM represented by SEQ ID NO : 8, said fusion protein comprising the sequence represented by SEQ ID NO : 10 as a hyperglycosylated linker between each of the three preceding proteins, and being represented by SEQ ID NO : 14.

The invention more particularly relates to the use as defined above, of the fusion protein between the feruloyl esterase B of *A. niger* represented by SEQ ID NO : 4, and the xylanase B of *A. niger* represented by SEQ ID NO : 6, said fusion protein comprising the sequence represented by SEQ ID NO : 10 as a hyperglycosylated linker between the two preceding proteins, and being represented by SEQ ID NO : 16.

The invention more particularly concerns the use as defined above, of fusion proteins between the feruloyl esterase B of *A. niger* represented by SEQ ID NO : 4, the xylanase B of *A. niger* represented by SEQ ID NO : 6, and the CBM represented by SEQ ID NO : 8 present in the cellobiohydrolase B of *A. niger*.

The invention more particularly relates to the use as defined above, of the fusion protein between the feruloyl esterase B of *A. niger* represented by SEQ ID NO : 4, the xylanase B of *A. niger* represented by SEQ ID NO : 6, and the CBM represented by SEQ ID NO : 8, said fusion protein comprising the sequence represented by SEQ ID NO : 10 as a hyperglycosylated linker between each of the three preceding proteins, and being represented by SEQ ID NO : 18.

The invention also relates to the use as defined above, for carrying out processes of plant cell-wall degradation in the frame of the preparation of the following compounds of interest:
- bioethanol,
- anti-oxidants, such as ferulic acid or caffeic acid that are cinnamic acids and, hydroxytyrosol, or gallic acid,
- flavours, such as vanillin or p-hydroxybenzaldehyde obtained from the biotransformation of the ferulic acid or the p-coumaric acid, respectively, or in the frame of the bleaching of pulp and paper.

The invention also relates to the use as defined above, wherein said fusion proteins are directly added to the plants or vegetal by-products as substrates, or are secreted by fungi cells transformed with nucleic acids encoding said fusion proteins, such as the fungi mentioned above, and more particularly *A. niger* and *Pycnoporus cinnabarinus*, said fungi being contacted with said plants or vegetal by-products as substrates.

The invention also concerns a process of plant cell-wall degradation for the preparation, from plants or vegetal by-products, of compounds of interest located in plant cell-wall, characterized in that it comprises the following steps:
- the enzymatic treatment of plants or vegetal by-products or industrial waste, with fusion proteins as defined above, or with transformed fungi cells as defined above,
- optionally, the physical treatment of plants or vegetal by-products using steam explosion in combination with the action of fusion proteins,
- optionally, the biotransformation with appropriate microorganisms or enzymes of the compounds released from the cell walls during the above enzymatic treatment,
- the recovery, and if necessary, the purification, of the compound of interest released from the cell walls during the above enzymatic treatment or obtained during the above biotransformation step.

Preferably, plants treated with fusion proteins in the process according to the invention are chosen among sugar beet, wheat, maize, rice, or all the trees used for paper industries.

Preferably, vegetal by-products or industrial waste treated with fusion proteins in the process according to the invention are chosen among wheat straw, maize bran, wheat bran, rice bran, apple marc, coffee marc, coffee by-products, olive mill wastewater The invention more particularly concerns a process as defined above for the preparation of anti-oxidants as compounds of interest, said process comprising:
- the treatment of plants or vegetal by-products with fusion proteins comprising at least two of the following cell-wall degrading enzymes which do not contain a CBM: feruloyl esterase A, feruloyl esterase B, chlorogenic acid hydrolase, xylanase, wherein the fusion protein is preferably chosen among feruloyl esterase A-xylanase, feruloyl esterase B-xylanase, feruloyl esterase A-feruloyl esterase A-xylanase, feruloyl esterase A-feruloyl esterase B-xylanase, chlorogenic acid hydrolase-xylanase.
- the recovery, and if necessary, the purification, of the anti-oxidants released from the cell walls of said plants or vegetal by-products.

The invention more particularly relates to a process as defined above for the preparation of cinnamic acids such as ferulic acid as anti-oxidant of interest, wherein the fusion protein used contains a feruloyl-esterase and a xylanase, and optionally a CBM, as defined above, and is more particularly chosen among SEQ ID NO : 12, SEQ ID NO : 14, SEQ ID NO : 16 and SEQ ID NO : 18.

Advantageously, in the frame of the preparation of anti-oxidants, such as ferulic acid, plants treated with fusion proteins defined above are chosen among the following: sugar beet, wheat, maize, rice, or vegetal by-products or industrial waste treated with fusion proteins defined above are chosen among the following: wheat straw, maize bran, wheat bran, rice bran, apple marc, coffee marc, coffee by-products, olive mill wastewater The invention also relates to a process as defined above for the preparation of flavours as compounds of interest, said process comprising:
- the treatment of plants or vegetal by-products with the fusion proteins used in the frame of the preparation of anti-oxidants as defined above,
- the biotransformation of the compounds released from the cell walls during the preceding step by contacting said compounds with non defined enzymes produced by microorganisms chosen among ascomycetes or basidiomycetes such as *A. niger* or *P. cinnabarinus*, respectively.
- the recovery, and if necessary, the purification, of the flavours obtained at the preceding step of biotransformation.

The invention more particularly relates to a process as defined above, for the preparation of vanillin as a flavour of interest, wherein the fusion protein used is chosen among those used for the preparation of ferulic acid as defined above, and the biotransformation step is carried out by contacting the ferulic acid released from the cell walls with non defined enzymes produced by ascomycetes or basidiomycetes such as *A. niger* or *P. cinnabarinus*, respectively, Advantageously, plants and vegetal by-products or industrial waste used in the frame of the preparation of flavours, such as vanillin, are chosen among those mentioned above for the preparation of anti-oxidants.

The invention also relates to a process as defined above, for the preparation of bioethanol as a compound of interest, said process comprising:
- the treatment of plants or vegetal by-products with fusion proteins comprising at least two of the following plant cell-wall degrading enzymes which do not contain CBM: cellulases, hemicellulases, esterases, laccases, peroxidases, aryl alcool oxidase, wherein the fusion protein is preferably chosen among the endoglucanase-exoglucanase, laccase-xylanase, xylanase-cellulase (endo or exo glucanase) said treatment being advantageously combined with a physical treatment of said plants or vegetal by-products,
- the biotransformation of the treated plants or vegetal by-products obtained from the preceding step to fermentescible sugars, by using fusion proteins described above or with a transformed fungus secreting the fusion proteins, in combination with enzymes chosen among cellulases, hemicellulases or esterases, or microorganisms chosen among ascomycetes such as *A. niger* or *Trichoderma reesei,*
- the biotranformation of the fermentescible sugars to bioethanol by yeast.

The invention more particularly relates to a process as defined above for the preparation of fermentescible sugars for subsequent bioethanol production, wherein the fusion protein is chosen among endoglucanase-exoglucanase, laccase-xylanase, xylanase-cellulase (endo or exo glucanase), Advantageously, plants and vegetal by-products or industrial waste used in the frame of the preparation of bioethanol are chosen among the following: wood, annual plants, or agricultural by-products.

The invention also relates to a process for the bleaching of pulp and paper, said process comprising:
- the chemical and physical treatment of plants or vegetal by-products in combination with fusion proteins comprising at least two of the following plant cell-wall degrading enzymes which do not contain a CBM: feruloyl esterase A, feruloyl esterase B, xylanase, laccase, aryl alcool oxidase, manganese peroxidase, lignine peroxidase, versatile peroxidase or cellobiose dehydrogenase.
- optionally, the biopulping of the treated plants or vegetal by-products obtained at the preceding step, with a transformed fungus secreting fusion proteins comprising at least two of the following plant cell-wall degrading enzymes which do not contain a CBM: feruloyl esterase A, feruloyl esterase B, xylanase, laccase, aryl alcool oxidase, manganese peroxidase, lignine peroxidase, versatile peroxidase or cellobiose dehydrogenase.

the biobleaching of the treated plants or vegetal by-products obtained at the preceding step with fusion proteins comprising at least two of the following plant cell-wall degrading enzymes which do not contain a CBM: feruloyl esterase A, feruloyl esterase B, xylanase, laccase, aryl alcool oxidase, manganese peroxidase, lignine peroxidase, versatile peroxidase or cellobiose dehydrogenase.

The invention more particularly relates to a process as defined above for the bleaching of pulp and paper, wherein the fusion protein used in the first step of treatment of plants and vegetal by-products is chosen among among feruloyl esterase A-xylanase, feruloyl esterase B-xylanase, feruloyl esterase A-feruloyl esterase A-xylanase, feruloyl esterase A-feruloyl esterase B-xylanase, laccase-xylanase, aryl alcool oxidase-manganese peroxidase, the fusion protein secreted by the transformed fungus used in the biopulping step is chosen among feruloyl esterase A-xylanase, feruloyl esterase B-xylanase, feruloyl esterase A-feruloyl esterase A-xylanase, feruloyl esterase A-feruloyl esterase B-xylanase, laccase-xylanase, aryl alcool oxidase-manganese peroxidase, overproduced by *P. cinnabarinus* or *A. niger*, and the fusion protein used in the biobleaching step is chosen among feruloyl esterase A-xylanase, feruloyl esterase B-xylanase, feruloyl esterase A-feruloyl esterase A-xylanase, feruloyl esterase A-feruloyl esterase B-xylanase, laccase-xylanase, aryl alcool oxidase-manganese peroxidase.

The invention also concerns the fusion proteins between at least two plant cell-wall degrading enzyme which do not contain a C-terminal carbohydrate-binding-molecule (CBM), and optionally a CBM, said enzymes and CBM being recombinant proteins corresponding to native proteins in fungi, or mutated forms thereof, as defined above.

The invention more particularly concerns fusion proteins as defined above, comprising linkers between at least two of the proteins comprised in said fusion proteins, said linkers being as defined above.

The invention more particularly relates to fusion proteins as defined above, between a feruloyl esterase and a xylanase, and optionally a CBM.

The invention more particularly concerns fusion proteins as defined above, between the feruloyl esterase A of *A. niger* represented by SEQ ID NO : 2, or the feruloyl esterase B of *A. niger* represented by SEQ ID NO : 4, and the xylanase B of *A. niger* represented by SEQ ID NO : 6.

The invention more particularly relates to the fusion protein as defined above, between the feruloyl esterase A of *A. niger* represented by SEQ ID NO : 2, and the xylanase B of *A. niger* represented by SEQ ID NO : 6, said fusion protein comprising the sequence represented by SEQ ID NO : 10 as a hyperglycosylated linker between the two preceding proteins, and being represented by SEQ ID NO : 12.

The invention also relates to fusion proteins as defined above, between the feruloyl esterase A of *A. niger* represented by SEQ ID NO : 2, the xylanase B of *A. niger* represented by SEQ ID NO : 6, and the CBM represented by SEQ ID NO : 8 present in the cellobiohydrolase B of *A. niger*.

The invention more particularly relates to the fusion protein as defined above, between the feruloyl esterase A of *A. niger* represented by SEQ ID NO : 2, the xylanase B of *A. niger* represented by SEQ ID NO : 6, and the CBM represented by SEQ ID NO : 8, said fusion protein comprising the sequence represented by SEQ ID NO : 10 as a hyperglycosylated linker between each of the three preceding proteins, and being represented by SEQ ID NO : 14.

The invention more particularly concerns the fusion protein as defined above, between the feruloyl esterase B of *A. niger* represented by SEQ ID NO : 4, and the xylanase B of *A. niger* represented by SEQ ID NO : 6, said fusion protein comprising the sequence represented by SEQ ID NO : 10 as a hyperglycosylated linker between the two preceding proteins, and being represented by SEQ ID NO : 16.

The invention also relates to fusion proteins as defined above, between the feruloyl esterase B of *A. niger* represented by SEQ ID NO : 4, the xylanase B of *A. niger* represented by SEQ ID NO : 6, and the CBM represented by SEQ ID NO : 8 present in the cellobiohydrolase B of *A. niger*.

The invention more particularly relates to the fusion protein as defined above, between the feruloyl esterase B of *A. niger* represented by SEQ ID NO : 4, the xylanase B of *A. niger* represented by SEQ ID NO : 4, and the CBM represented by SEQ ID NO : 6, said fusion protein comprising the sequence represented by SEQ ID NO : 10 as a hyperglycosylated linker between each of the three preceding proteins, and being represented by SEQ ID NO : 18.

The invention also relates to the nucleic acids encoding a fusion protein as defined above.

The invention more particularly relates to the nucleic acids represented by SEQ ID NO : 11, 13, 15 and 17 encoding the fusion proteins represented by SEQ ID NO : 12, 14, 16 and 18 respectively.

The invention also relates to the nucleic acids represented by SEQ ID NO : 19 and 21 corresponding to SEQ ID NO : 11 and 13 wherein the sequence SEQ ID NO : 1 is replaced by the sequence SEQ ID NO : 23 encoding the pre-feruloyl esterase A corresponding to SEQ ID NO : 24, said nucleic acids SEQ ID NO : 19 and 21 encoding the pre-proteins of fusion corresponding to sequences SEQ ID NO : 20 and 22.

The invention also concerns the nucleic acids represented by SEQ ID NO : 25 and 27 corresponding to SEQ ID NO : 15 and 17 wherein the sequence SEQ ID NO : 3 is replaced by the sequence SEQ ID NO : 29 encoding the pre-feruloyl esterase B corresponding to SEQ ID NO : 30, said nucleic acids SEQ ID NO : 25 and 27 encoding the pre-proteins of fusion corresponding to sequences SEQ ID NO : 20 and 22.

The invention also relates to the vectors such as pAN 52.3, transformed with a nucleic acid as defined above.

The invention also concerns host cells such as ascomycetes or basidiomycetes, and more particularly *A. niger* or *P. cinnabarinus*, transformed with a nucleic acid as defined above, by using vectors as mentioned above.

The invention also relates to a process for the preparation of fusion proteins as defined above, comprising the culture in vitro of host cells as defined above, the recovery, and if necessary, the purification of the fusion proteins produced by said host cells in culture.

The invention is further illustrated with the detailed description which follows of the preparation and properties of the chimerical enzymes FLX (SEQ ID NO : 12) and FLXLC (SEQ ID NO : 14).

Two chimerical enzymes FLX and FLXLC were designed and successfully overproduced in *Aspergillus niger*. FLX construction is composed of the sequences encoding the feruloyl esterase A (FAEA) fused to the endoxylanase B (XYNB) of *A. niger*. A C-terminal Carbohydrate-Binding-Module (CBM family 1) was grafted to FLX generating the second hybrid enzyme: FLXLC. Between each partner, a hyperglycosylated linker was included to stabilize the constructions. Hybrid proteins were purified to homogeneity and molecular masses were estimated to be 72 kDa and 97 kDa for FLX and FLXLC, respectively. Integrity of hybrid enzymes was checked by immunodetection that showed a single form by using antibodies raised against FAEA and polyhistidine tag. Physico-chemical properties of each catalytic module of the bifunctional enzymes corresponded to those of the free enzymes. In addition, we checked that FLXLC exhibited a strong affinity for microcrystalline cellulose (Avicel) with binding parameters corresponding to a $K_d$ 9.9 $10^{-8}$ M for the dissociation constant and 0.98 μmol/g Avicel for the binding capacity. Both bifunctional enzymes were investigated for their capacity to release ferulic acid from natural substrates: maize and wheat brans. As compared to free enzymes FAEA and XYNB, a higher synergistic effect was obtained by using FLX and FLXLC for both substrates. Moreover, the synergy was increased for FLXLC as compared to FLX for the ferulic acid release using maize bran as the substrate confirming a positive role of the CBM. In conclusion, these results demonstrated that the fusion onto bifunctional enzymes of naturally free cell-wall hydrolases and a CBM from *A. niger*, allows to increase the synergistic effect on the degradation of complex substrates.

Materials and Methods

Strains and Culture Media

*Escherichia coli* JM109 (Promega) was used for construction and propagation of vectors and *A. niger* strain D15#26 (pyrg-) (22) for production of the recombinant proteins. After co-transformation with vectors containing respectively the pyrG gene and the expression cassette FLX or FLXLC (FIG. 1), *A. niger* was grown for selection on solid minimal medium (without uridine) containing 70 mM NaNO$_3$, 7 mM KCl, 11 mM KH$_2$PO$_4$, 2 mM MgSO$_4$, glucose 1% (w/v), and trace elements [1000× stock: 76 mM ZnSO$_4$, 25 mM MnCl$_2$, 18 mM FeSO$_4$, 7.1 mM CoCl$_2$, 6.4 mM CuSO$_4$, 6.2 mM Na$_2$MoO$_4$, 174 mM ethylenediaminetetraacetic acid (EDTA)]. In order to screen the transformants for the recombinant proteins production in liquid medium, 100 ml of culture medium containing 70 mM NaNO$_3$, 7 mM KCl, 200 mM Na$_2$HPO$_4$, 2 mM MgSO$_4$, glucose 6% (w/v) and trace elements were inoculated by 1×10$^6$ spores. ml$^{-1}$ in a 500 mL baffled flask. *A. niger* BRFM131 (Banque de Ressources Fongiques de Marseille) was used for genomic DNA extraction and the resulting DNA was used as template for PCR amplification strategy of the linker-cbm sequence;

Expression Vectors Construction and Fungal Transformation

The fusion of the sequences coding for FAEA (SEQ ID NO : 19; Y09330), XYNB (SEQ ID NO : 5; AY126481), and CBM (SEQ ID NO : 7; AF156269) from *A. niger* were performed by the overlap extension PCR method (25). The *A. niger* FAEA-encoding region was amplified from cDNA (41) using the forward primer 5'-GGAC TCATGAAGCAATTCTCTGCAAAATAC-3' (BspHI) and the reverse primer 5'-ACTGGAGTAAGTCGAGC-CCCAAGTACAAGCTCCGCT-3'. Genomic DNA coding for the linker region of CBHB (SEQ ID NO : 9; AF156269), was amplified from *A. niger* BRFM131 using the forward primer 5'-AGCGGAGCTTGTACTTGGGGCTCGACT-TACTCCAGT-3' and the reverse primer 5'-GGTC-GAGCTCGGGGTCGACGCCGCCGATGTCGAACT-3'. Finally, the xynB gene was amplified from cDNA (29) with a forward primer 5'-AGTTCGACATCGGCGGCGTCGAC-CCCGAGCTCGACC-3' and a reverse primer 5'-GGCT AAGCTTTTA GTGGTGGTGGTGGTGGTGCTGAACAGT-GATGGACGAAG-3' (HindIII) (His-tag is dot lined in all sequences). Resulting overlapping fragments were mixed and a fused sequence was synthesized in a one-step reaction by using both external primers. Construction was cloned in pGEM-T vector (Promega) and the cloned PCR product was checked by sequencing. The fused fragment was cloned into NcoI-HinIII linearized and dephosphorylated pAN52.3 to obtain pFLX plasmid (FIG. 1,A). FLXLC plasmid was constructed using pFLX as template for amplification of the fragment coding for the recombinant FAEA-linker-XYNB sequence with the forward primer 5'-GGAC TCATGAAGCAATTCTCTGCAAAATAC-3' (BspHI) and the reverse primer 5'-ACTGGAGTAAGTCGAGCCCT-GAACAGTGATGGACGA-3'. Genomic DNA from *A. niger* BRFM131 was used as template for PCR amplification of the linker-CBM sequence with two specific primers designed from the available cbhB sequence (AF156269): a forward primer 5'-TCGTCCATCACTGTTCAGGGCTCGACT-TACTCCAGT-3' and a reverse primer 5'-ATGC AAGCTTTTA GTGGTGGTGGTGGTGGTGCAAACACT-GCGAGTAGTAC-3' (HindIII). Fused fragment was synthesized by overlap extension PCR method by using both external primers, controlled by sequencing, and cloned into pAN52.3 to obtain the pFLXLC vector (FIG. 1,B). In both expression vectors, the *A. nidulans* glyceraldehyde-3-phosphate dehydrogenase gene (gpdA) promoter, the 5' untranslated region of the gpdA mRNA, and the *A. nidulans* trpC terminator were used to drive the expression of recombinant sequences. In addition, the signal peptide (21 amino acids) of the FAEA was used to target the secretion of both recombinant proteins.

Both fungal cotransformations were carried out as described by Punt and van den Hondel (39) by using the pFLX or the pFLXLC expression vectors, respectively, and pAB4-1 (48) containing the pyrG selection marker, in a 10:1 ratio. In addition, *A. niger* D15#26 was transformed with the pyrG gene without the expression vector for control experiment. Co-transformants were selected for uridine prototrophy on a selective minimal medium plates (without uridine) and incubated for 8 days at 30° C. In order to screen transformants, forty individual clones for each construction were cultivated and checked daily.

Screening of Feruloyl Esterase and Xylanase Activities

Cultures were monitored for 14 days at 30° C. in a shaker incubator (130 r.p.m). pH was adjusted to 5.5 daily with a 1 M citric acid solution. Each culture condition was performed in duplicate. From liquid culture medium, aliquots (1 ml) were collected daily and mycelium was removed by filtration. Esterase activity was assayed as previously described using methyl ferulate (MFA) as the substrate (40) and xylanase activity was calculated by measuring the amount of xylose released from 1% (w/v) birchwood xylan based on the method of Bailey et al. (1). The enzymes were incubated with a xylan solution [1% (w/v) xylan from birchwood, 50 mM sodium citrate buffer pH 5.5)] at 45° C. for 5 min. The reducing sugars released were determined by the DNS method with xylose as standard (35). All assays were performed by using blanks to correct any backgrounds in enzyme and substrate samples.

Activities were expressed in nkatal (nkat), 1 nkat being defined as the amount of enzyme that catalyses the release of 1 nmol of ferulic acids or of 1 nmol of reducing sugars per sec under established conditions. Each experiment was done in duplicate and measurements in triplicate, and standard deviation was less than 2% of the mean for esterase activity and less than 5% for xylanase activity.

Purification of Recombinant Proteins

The best isolate for each construction was inoculated in the same conditions as the screening procedure. Culture was harvested after 8 days of growth, filtered (0.7 μm) and concentrated by ultrafiltration through a polyethersulfone membrane (molecular mass cut-off of 30 kDa) (Millipore). Concentrated fractions were dialyzed against a 30 mM Tris-HCl, pH 7.0, binding buffer and the purification of His-tagged proteins was performed on a Chelating Sepharose Fast Flow column (13×15 cm) (Amersham Biosciences) (38). Concerning free proteins, recombinant xylanase B, that contains a his-tag sequence, was also purified on Chelating Sepharose Fast Flow column as already described (29). Finally, the recombinant FAEA was purified in a one-step procedure using a phenyl-sepharose column as already described (41).

Characterization of Recombinant Proteins

Protein analysis and N-Terminal amino-acid sequence determination. Protein concentration was determined according to Lowry et al. (34) with bovine serum albumin as the standard. Protein production and purification were checked using Coomassie blue stained SDS-PAGE (11% polyacrylamide) slab gels. The N-terminal sequences were determined according to Edman degradation from an electroblotted FLX and FLXLC samples (100 µg) onto a polyvinylidine difluoride membrane (Millipore). Analyses were carried out on an Applied Biosystem 470A.

Western blot analysis. Total and purified proteins were electrophoresed in 11% SDS/polyacrylamide gel according to Laemmli (28) and electroblotted onto BA85 nitrocellulose membranes (Schleicher and Schuell) at room temperature for 45 min. Membranes were incubated in blocking solution (50 mM Tris, 150 mM NaCl and 2% (v/v) milk pH 7.5) overnight at 4° C. Then, membranes were washed with TBS-0.2% Tween and treated with blocking solution containing anti-FAEA serum at a dilution of 1/8000 or containing anti-polyhistidine-peroxydase serum (Sigma). For anti-FAEA antibodies, membranes were subsequently incubated with goat anti-rabbit immunoglobin G conjugated with horseradish peroxidase (Promega). Signals were detected with chemiluminescence Western blotting kit (Roche) according to the manufacturer's procedure.

Temperature and pH stability of recombinant proteins. Thermostability of the purified recombinant proteins was tested in the range of 30 to 70° C. Aliquots were preincubated at the designated temperature and after cooling at 0° C., esterase and xylanase activities were then assayed as previously indicated in standard conditions. Samples were analysed by SDS-PAGE after incubation in order to verify integrity of the bifunctional proteins. Effect of the pH on protein stability was studied by incubating the purified recombinant proteins in citrate-phosphate buffer (pH 2.5-7.0) and sodium phosphate (pH 7.0-8.0). All incubations were performed for 90 min, and then aliquots were transferred in standard reactional mixture to determine the amount of remaining activity. The activity determined prior to the preincubations was taken as 100%.

Effect of temperature and pH on esterase and xylanase activities. To determine optimal temperature under the conditions used, aliquots of purified recombinant proteins were incubated at various temperatures (30 to 70° C.) and esterase and xylanase activities were assayed. Optimal pH was determined by using citrate-phosphate buffer (pH 2.5-7.0) and sodium phosphate buffer (pH 7.0-8.0) using standard conditions.

Determination of cellulose-binding capacity and dissociation constants. Samples of purified FLX and FLXLC were added to 2 ml microcentrifuge tubes containing cellulose in 25 mM potassium phosphate buffer (pH 7) in a final volume of 1 ml. The capacity of FLX (control) and FLXLC to bind to the Avicel PH101 cellulose (Fluka) was determined by using various amounts of recombinant proteins (between 30 and 170 µg) and a constant amount of cellulose (2 mg). Both recombinant proteins were incubated with cellulose for 1 h at 4° C. with gentle agitation. After centrifugation (4000×g for 10 min), the amount of residual proteins in the supernatant fluid (free enzyme) was determined. The amount of enzyme bound to cellulose was calculated by subtracting the amount of free FLX or free FLXLC from the total amount added. Data were analysed by drawing double-reciprocal plots of 1/bound enzyme versus 1/free enzyme. The dissociation constant is defined as $1/B=(Kd/Bmax \times 1/F)+1/Bmax$, where B is the bound enzyme concentration and F is the free enzyme concentration (21, 37).

Application Tests

Enzymic hydrolysis. Wheat bran (WB) and maize bran (MB) were destarched. These substrates were submitted to heat treatment at 130° C. for 10 min. Enzymic hydrolyses were performed in 0.1 M 3-(N-morpholino)propanesulfonic acid (MOPS) buffer containing 0.01% sodium azide at pH 6.0, in a thermostatically controlled shaking incubator at 40° C. WB or MB (200 mg) were incubated with the purified, FAEA (SEQ ID NO : 2), XYNB (SEQ ID NO : 6), FAEA+XYNB, FLX and FLXLC, independently, in a final volume of 5 ml. The purified enzyme concentrations for free and bifunctional enzymes were: 11 nkatal of esterase activity and 6496 nkatal of xylanase activity per 200 mg of dry bran for each assay. This ratio corresponds to the molar to molar condition found in the purified bifunctional enzyme. Each assay was done in duplicate and the standard deviation was less than 5% from the mean of the value for WB and MB.

Preparation of the alkali-extractable hydroxycinnamic acid. Total alkali-extractable hydroxycinnamic acid content was determined by adding 20 mg of WB or MB in 2 N NaOH and incubated for 30 min at 35° C. in the darkness. The pH was adjusted to 2 with 2N HCl. Phenolic acids were extracted three times with 3 ml of ether. The organic phase was transferred to a test tube and dried at 40° C. One milliliter of methanol/$H_2O$ (50:50) (v/v) was added to dry extract and samples were injected on an HPLC system as described in the next section. The total alkali-extractable ferulic acid content was considered as 100% for the enzymic hydrolysis.

Ferulic acid determination. Enzymatic hydrolysates were diluted to ½ with methanol 100%, centrifuged at 12,000×g for 5 min and supernatants were filtered through a 0.2 µm nylon filter (Gelman Sciences, Acrodisc 13, Ann Arbor, Mich.). Filtrates were analyzed by HPLC (25 µL injected). HPLC analyses were performed at 280 nm and 30° C. on a HP1100 model (Hewlett-Packard Rockville, Md.) equipped with a variable UV/VIS detector, a 100-position autosampler-autoinjector. Separations were achieved on a Merck RP-18 reversed-phase column (Chromolith 3.5 µm, 4.6×100 mm, Merck). The flow rate was 1.4 ml/min. The mobile phase used was 1% acetic acid and 10% acetonitrile in water (A) versus acetonitrile 100% (B) for a total running time of 20 min, and the gradient changed as follows: solvent B started at 0% for 2 min, then increased to 50% in 10 min, to 100% in 3 min until the end of running. Data were processed by a HP 3365 ChemStation and quantification was performed by external standard calibration.

Results

Design and Study of the Bifunctional Enzymes Production

Figure 2:
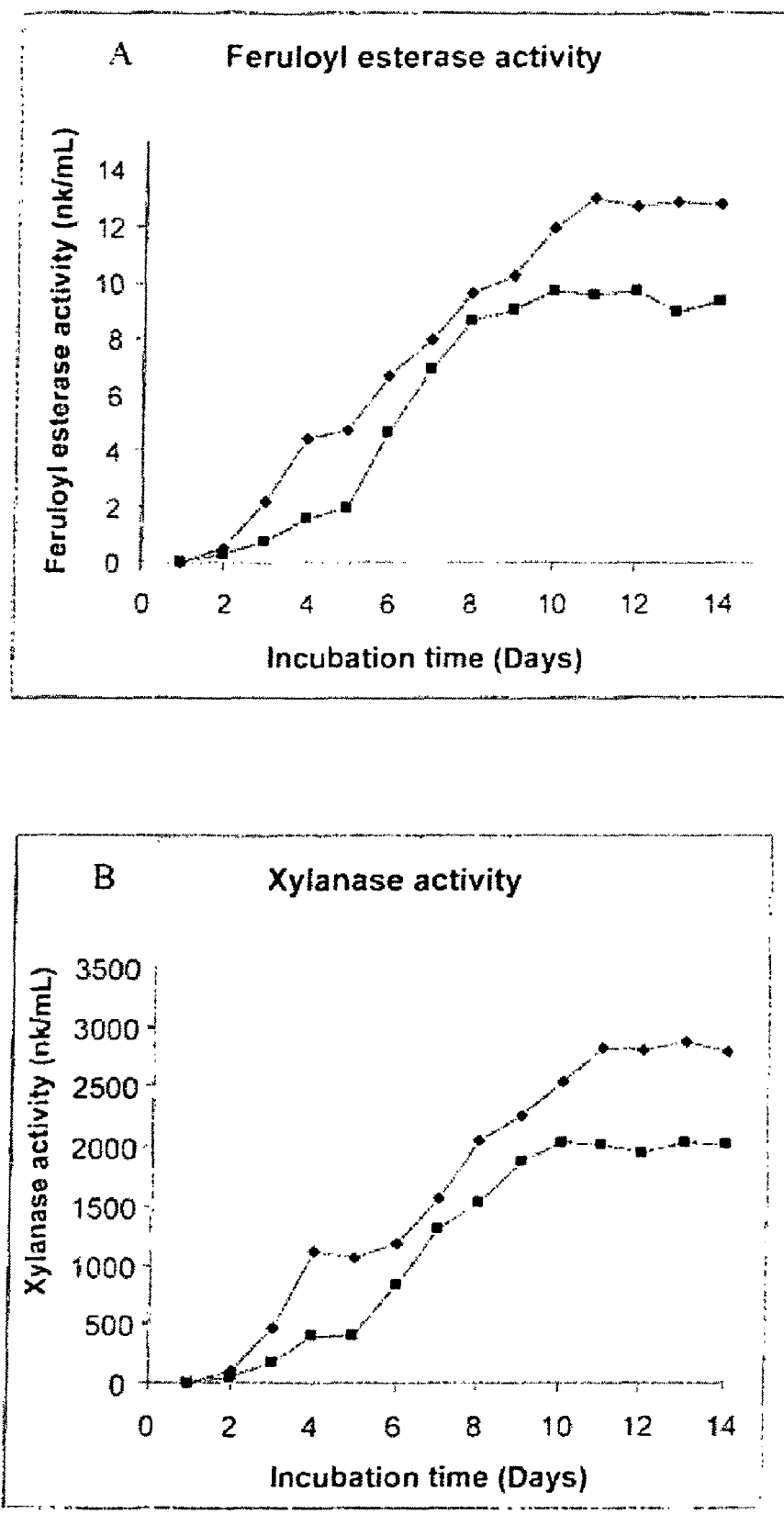

The *A. niger* sequences encoding the feruloyl esterase A (FAEA) and the xylanase B (XYNB) were genetically fused by adding, between both partners, a sequence from the cellobiohydrolase B gene (cbhB) coding for a hyperglycosylated linker (FIG. 1.A). For the second construction FLXLC, the corresponding fusion FLX was fused to a partial sequence of *A. niger* cbhB gene coding for the linker-CBM (FIG. 1.B). Both translational fusions were placed under the control of the strong and constitutive gpdA promoter and the trpC terminator with the endogeneous faeA signal sequence to target the secretion. *A. niger* D15#26 protoplasts were co-transformed with a mixture of expression vector pFLX or pFLXLC and plasmid pAB4-1 containing the pyrG gene. Transformants were selected for their abilities to grow on a minimum medium plate without uridine. Forty transformants for each construction were inoculated into a glucose-minimal medium repressing the endogenous faeA and xynB gene expression. For the control host transformed with pAB4-1, no esterase or xylanase activity was detected. For both constructions, esterase and xylanase activities were detected in the extracellular media of transformants after 2 days of growth (FIG. 2). Feruloyl esterase and xylanase activities were detected as a synchronic way during the culture. Activities increase until day 10 and day 11 for the best FLXLC and FLX transformant, respectively, to reach a level that is more or less stable until day 14. Maximal esterase activity reached 13.0 nkat/ml for FLX and 9.8 nkat/ml for FLXLC transformant. Concerning xylanase activity, a maximal of 2870 nkat/ml for FLX and 2038 nkat/ml for FLXLC transformant were obtained. Considering specific activity of FAEA partner into bifunctional enzymes, production yields were estimated at 1.4 g/L and 1.5 g/L for FLX and FLXLC transformants, respectively.

Biochemical and Kinetic Characterization of Bifunctional Enzymes

Figure 3:
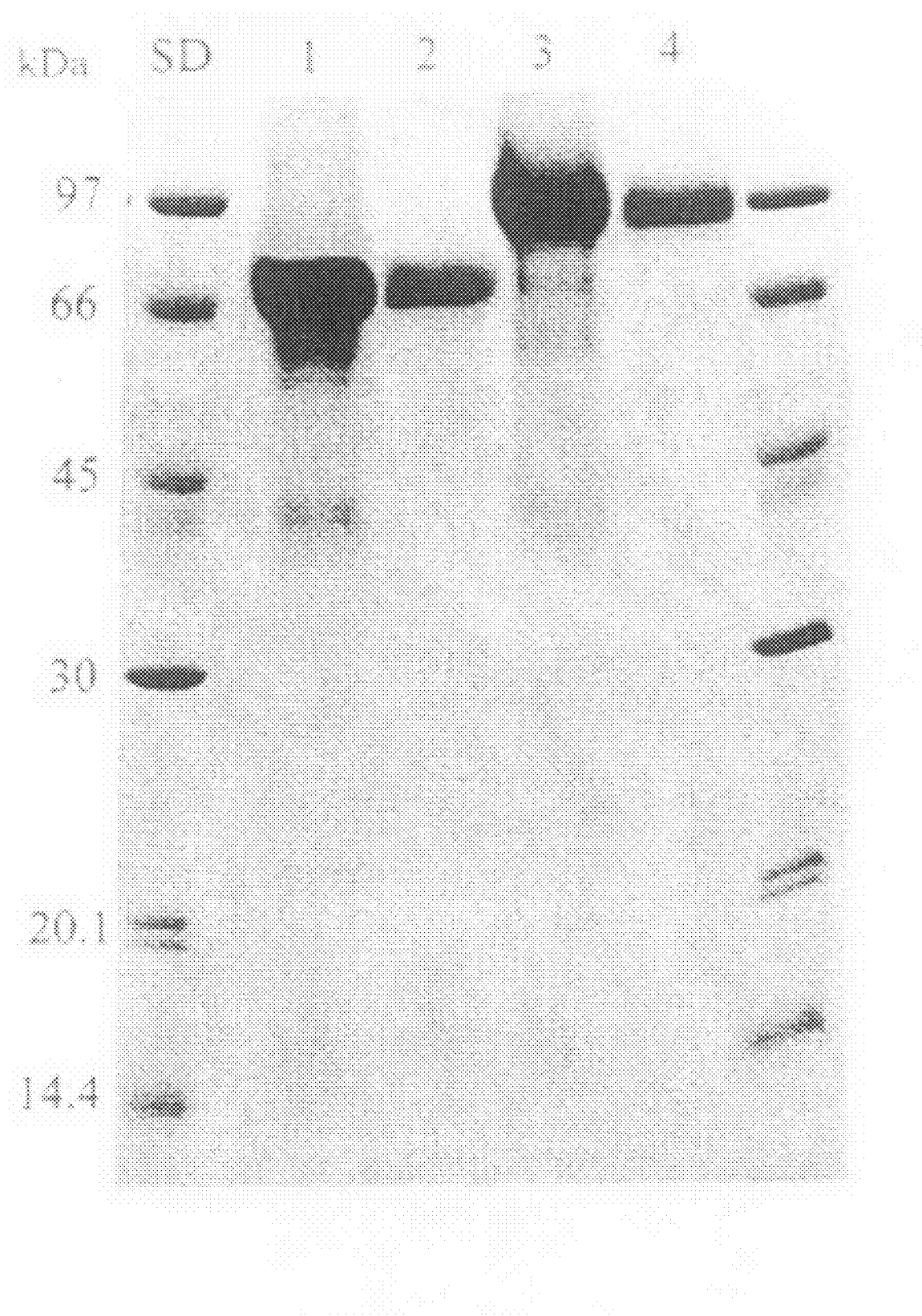

SDS-PAGE and Western blot analysis. In both cases, the produced proteins were checked by electrophoresis on a SDS/polyacrylamide gel (FIG. 3, lanes 1 and 3). Predominant bands around 72 kDa and 97 kDa were observed in the total extracellular proteins from FLX and FLXLC transformants, respectively. Difference between observed and theorical molecular masses for FLX and FLXLC suggested a glycosylation around 12% (w/w) and 26% (w/w), respectively. Recombinant enzymes were purified on a Chelating Sepharose Fast Flow column and the homogeneity of fractions was controlled by SDS-PAGE (lanes 2 and 4).

Figure 4:
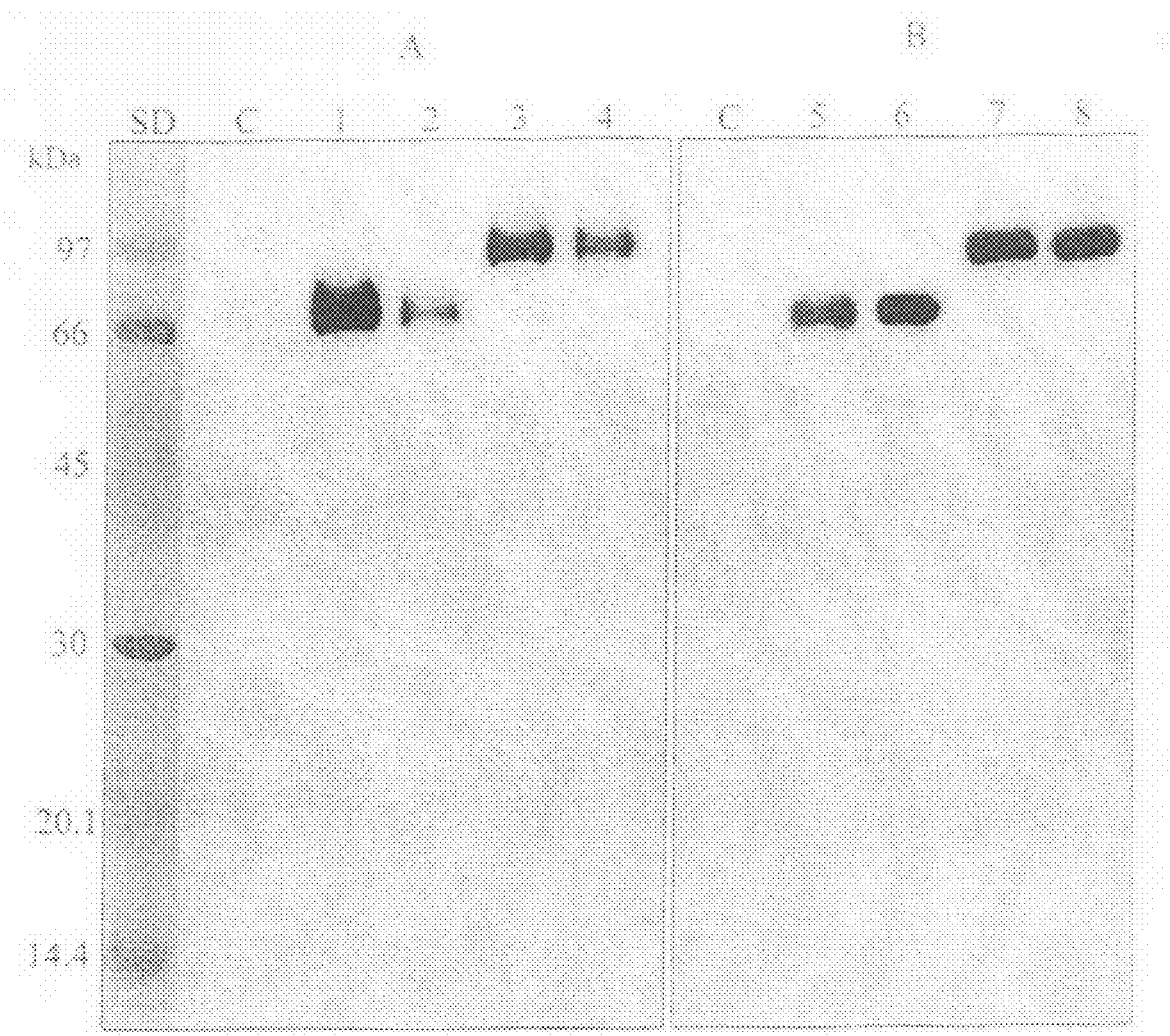

Both chimeric enzymes from total proteins supernatants and purified fractions were immunodetected by using antibodies raised against FAEA (FIG. 4.A). One single band was revealed from the total protein extracts (lanes 1,3) and from the purified samples (lanes 2,4) for FLX and FLXLC transformants, respectively. Antibodies raised against the C-terminal histidine-tag were also used for immunodetection in order to control the integrity of recombinant proteins, as antibodies raised against xylanase or CBM were not available (FIG. 4.B). One single band was detected for FLX and FLXLC confirming that the bifunctional enzymes were produced as intact proteins without any degradation form (lanes 5 to 8). Negative control (C) confirmed that both antibodies were epitope-specific and that the endogenous FAEA was not produced in these culture conditions.

N-terminal sequencing. The first five amino acids of FLX and FLXLC were sequenced (ASTQG) and aligned with the native FAEA. Alignments reveal 100% identity between recombinant proteins and native FAEA. These results confirmed that FLX and FLXLC were correctly processed.

Analysis of the bifunctional enzymes-cellulose affinity and binding capacity. Contrary to FLX, FLXLC contains at the C-terminus end, the CBM from *A. niger* cellobiohydrolase B. Interaction assays of FLXLC with cellulose were carried out in order to determine the binding parameters of CBM. Cellulose binding affinity and binding capacity of FLXLC were determined towards the microcrystalline cellulose, Avicel PH101. Measured values were of $9.9 \cdot 10^{-8}$ M and 0.98 µmol/g Avicel for the dissociation constant ($K_d$) and the binding capacity, respectively. As expected, no interaction was found for the chimeric enzyme FLX (without CBM).

Biochemical and kinetic parameters. In order to control whether the fusion of both enzymatic partners with or without CBM have modified characteristics of each enzyme, biochemical and kinetic parameters of FLX and FLXLC were compared to the free recombinant FAEA and XYNB according to the esterase and xylanase activities (Table. 1). Concerning pH optimum and stability, no significant difference was found between both bifunctional enzymes and free FAEA or XYNB. For the temperature optimum and stability, the only distinction concerns a slight shift measured for the xylanase activities. In addition, integrity of FLX and FLXLC was controlled by SDS-PAGE after incubation at different temperatures and both bifunctional enzymes were fully stable up to 45° C. and were partly cleaved at 50° C. The first amnino-acids of the cleaved form was sequenced and identified as GSGSS. Alignment of this sequence with FLX and FLXLC reveals 100% identity with a sequence found in the linker. These results showed that the hyperglycosylated linker is stable up to 45° C. and a cleavage appears at 50° C. before the GSGSS sequence. The chimeric FLXLC protein, containing two linker sequences, was cleaved only at the C-terminal linker (between XYNB and CBM). Potential cleavage site for proteases were checked on the aminoacids sequences of both hybrid proteins by using peptide cutter tool (19) and no cleavage site was found in the neighbourhood of GSGSS.

Concerning kinetic properties, the Michaelis constants for FLX and FLXLC were measured from a Lineweaver-Burk plot by using MFA and birchwood xylan as substrates. The values found for FLX and FLXLC were in agreement with those found for the free recombinant FAEA and XYNB (Table. 1). Specific activities of bifunctional enzymes were determined based on feruloyl esterase and xylanase activities and compared to the free FAEA and XYNB (Table. 1). Values found for bifunctional enzymes were close to those found for the free FAE and XYNB.

In conclusion, these results confirmed that biochemical and kinetic parameters for the fused enzymatic modules (FAEA and XYNB) were mainly conserved into the bifunctional complexes FLX and FLXLC.

Enzymatic release of ferulic acid from wheat and maize brans.

Figure 5:
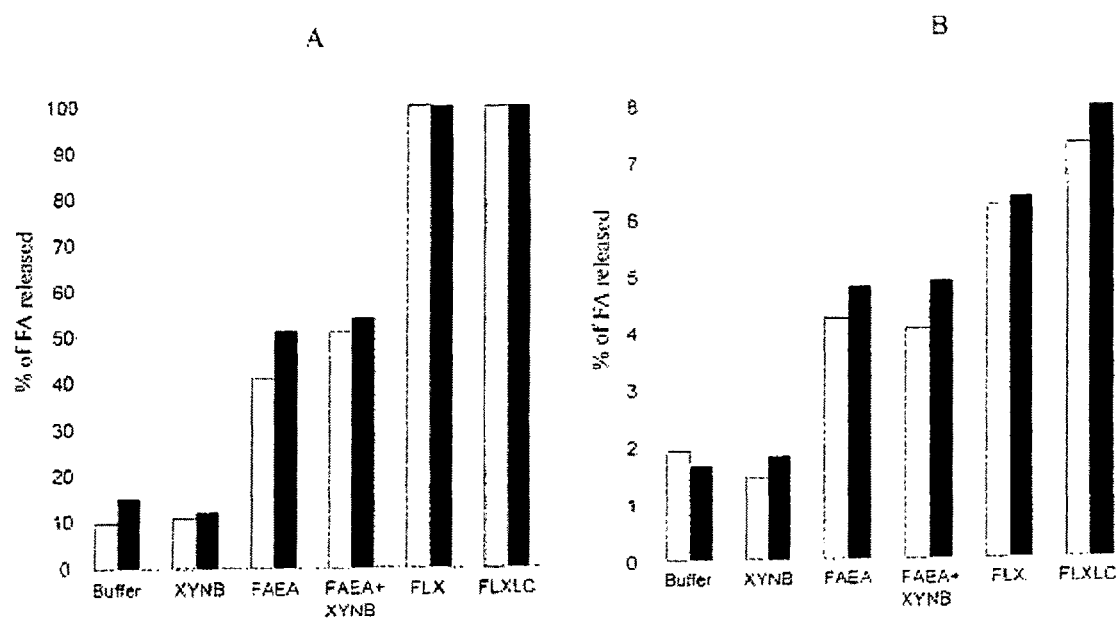

In order to study the synergistic effect generated by the physical proximity of two enzymes into the bifunctional proteins and the influence of the CBM addition, FLX and FLXLC were compared to the free enzymes FAEA and XYNB for the FA release efficiency. All enzymes were purified to homogeneity and incubated with WB and MB because of their naturally high amount of FA contained in the cell wall. By using free FAEA, 41% and 51% of the total alkali-extractable FA from WB was released after 4 and 16 h, respectively (FIG. 5,A). These percentages were slightly increased to 51% (4 h) and 54% (16 h) with the addition of free XYNB. Considering the effect of FLX or FLXLC, we observed a total release of FA after only 4 h of incubation. With the MB as the substrate (FIG. 5,B), free FAEA released 4.2%, 4.8% of FA after 4 h and 16 h, respectively, and the addition of XYNB didn't increase this percentage. However, FLX and FLXLC were able to release 6.2% and 7.2% after 4 h of hydrolysis, respectively. If enzymatic treatment was overnight for 16 h, releases were increased to 6.3% and 7.9% for, respectively, FLX and FLXLC. The synergy factors were determined and compared between free (FAEA+XYNB) and fused enzymes (FLX and FLXLC). As calculated in the table 2, the calculated ratio was higher than 1, demonstrating for both substrates, that the synergistic effect is better for the bifunctional enzymes than the corresponding free enzymes. Concerning the FA release of MB, the synergy is higher for FLXLC (1.80 and 1.62) than for FLX (1.53 and 1.30) after 4 h and 16 h, respectively. As a conclusion, these results showed that, for both substrates, bifunctional enzymes FLX and FLXLC were more efficient for the FA release as compared to the corresponding free enzymes (FAEA+XYNB). Moreover, these results seems to show that FLXLC is more adapted for the FA release using MB as the substrate, suggesting a positive effect generated by the CBM.

CONCLUSION

A wide range of enzymes is required for biodegradation of the plant cell wall due to its heterogeneity in composition and structure. Some combinations between different main-chain and accessory hydrolytic enzymes demonstrated important synergistic effect leading to an efficient degradation of the cell wall (9, 12). In this study, two plant cell wall-degrading enzymes and a carbohydrate-binding-module of *A. niger* were fused to study the synergistic effect on degradation of natural substrates. The construction of such hybrid proteins is an original aspect of protein engineering opening a wide range of potential applications. Here, the concept lies in the recruiting of two functional units to create improved bifunctional proteins (3, 36). Such multimodular organisations are commonly found in the Nature, leading to enzyme production with more than one enzymatic activity or protein function. In the biotechnology area, some bifunctional proteins were already investigated, including, for instance, a hybrid of α-amylase and glucoamylase (44). Results of this study demonstrated an increase of enzyme efficiency as compared to the free enzymes for the digestion of raw starch. In another work, a chimeric xylanase/endoglucanase (XynCenA) with an internal CBM was constructed but results showed that hybrid enzyme did not significantly affected the hydrolysis on homogeneous xylans or cellulosic substrates as compared to free enzyme, however, no application test was investigated on natural substrate (46).

In order to evaluate the effect generating by the physical proximity of two cell-wall hydrolases, FAEA was fused to XYNB (construction FLX). A fungal CBM from the *A. niger* CBHB was fused at the C-terminus extremity in the second construction (FLXLC) to target the bifunctional enzyme on cellulose. For both constructions, a hyperglycosylated linker peptide was fused between each module (FAEA, XYNB or CBM) for three main reasons. Firstly, the linker is known to retain the capacity of modules to fold independently and to conserve a conformational freedom relative to one another (36). In the present case, both feruloyl esterase and xylanase were able to adopt this conformation and the engineered bifunctional proteins were active with biochemical and kinetic properties corresponding to free enzymes. Secondly, high degree of glycosylation of the linker allows to increase the stability of proteins sequence by protecting the linker from protease activities and finally, by avoiding the frequent problem of cleavage between fused modules (8, 36). This effect was observed because both bifunctional enzymes were stable as shown by SDS-PAGE and Western blot analysis. However, stability of hybrid enzymes was shown to have some limits with thermal treatment. Indeed, the influence of the heat treatment on the FLX and FLXLC integrity showed that they were stable up to 45° C. and then cleaved in the linker sequence at 50° C. Lastly, the hyperglycosylated linker could have a positive role in secretion increasing the production yield as demonstrated for the hyperglycosylated linker from the *A. niger* glucoamylase (32). Indeed, glycosylation sites due to the presence of one or two linkers for FLX and FLXLC, respectively, could extend retention of recombinant proteins in the endoplasmic reticulum, thereby providing additional time for correct folding and resulting in an increase of production (42). This latter hypothesis could explain why the production yields for both bifunctional enzymes were higher than those obtained for the corresponding free recombinant enzymes (29, 41).

In order to study the synergistic effect generated by the proximity of both enzymatic modules, and not a gain due to modification of the enzyme properties as a result of change of protein conformation during folding, the biochemical and kinetic characteristics of each module were carefully controlled. All the main biochemical and kinetic properties of both bifunctional proteins FLX and FLXLC, i.e. temperature and pH stabilities, optimal temperature and pH, $K_m$ and specific activities, were in the same range as compared to free enzymes. Concerning the CBM originating from the *A. niger* CBHB, binding assays were performed on cellulose, as this latter was not characterized in the past (20). Avicel cellulose has an important degree of polymerisation of 100-250 glucopyranose units and 50-60% of crystalline form with a crystalline phase essentially composed of type $I_\beta$ characteristic of higher plants (49). Results showed that FLXLC possess affinity for Avicel confirming that the structure of CBM is not perturbed and that CBM conserved its function into the hybrid enzyme.

Both bifunctional proteins FLX and FLXLC were finally tested to study the effect of the physical proximity of two complementary fungal enzymes on the enzymatic synergy and the influence of the CBM addition. The application test was based on the FA release from two natural and model substrates, WB and MB, known for their high amount of FA in the plant cell wall of approximately 1% and 3% (w/w), respectively (43). Both substrates are generated from agriculture and could be valorizated in agro-food, cosmetic and pharmaceutical sectors (4, 26). Free enzymes were able to release 54% and 4.8% of the FA content from WB and MB, respectively. In contrast, bifunctional enzymes efficiently released the totality of FA from WB and up to 6.3% or 7.9% from MB, depending on the presence or not of the CBM. So far, previous results found for the FA release from WB were obtained with a *Trichoderma viride* xylanase and the FAEA from *A. niger*, in which a maximum of 95% (w/w) total ferulic acid was released (15). Concerning MB, important amount of FA was released (up to 13.6%), by using commercial preparation Novozym 342 from *Humicola insolens* (5). However, we should considered that this commercial preparation contained different kind of enzymatic activities. In present assay, the totality of FA from WB was released by the bifunctional enzymes treatment, whereas less than 8% was obtained with MB. Although ferulic acid content in maize bran is higher than that found in the wheat bran, maize bran xylan is more substituted with xylose, arabinose and galactose residues (7, 15). Thus, this difference could be explained by the number of substitutions on the heteroxylan backbone on maize, the presence of highly branched xylose in the side-chain, and the presence of a linkage between arabinose and xylose at the proximity of FA group, which seriously restrict enzyme accessibility. Finally, if we considered the hydrolysis of MB by FLXLC, CBM showed a positive effect on the FA release, probably (i) because of the cellulose targeting that increases the enzyme concentration close to the substrate and/or (ii) the destabilization of the cellulose structure making the substrate more accessible. As a conclusion of application tests, by using FLX or FLXLC, a better synergistic effect on both substrates was obtained for the FA release as compared to the free enzymes FAEA and XYNB. The general enhanced synergy was suggested to be due to the physical proximity of each enzymatic partner into the bifunctional enzymes as all main biochemical and kinetic properties were not changed for each partner in hybrid proteins. In the case of FLXLC, synergy was positively influenced by the C-terminal CBM addition. Furthermore, it also could be proposed that spatial orientation of active sites is not perturbed between fused modules.

As a general conclusion, construction of new enzymatic tools for plant cell wall degradation associating complementary cell-wall hydrolases such as an accessory enzyme (FAEA) and a main-chain cleaving enzyme (XYNB), was shown to be a strategy of interest to increase the synergistic effect of enzymatic partners. For biotechnological applications, utilization of such hybrid proteins is an alternative to expensive and polluting chemical treatments or to improve already existing enzymatic processes for valorization of vegetal by-products in the pulp and paper, agro-industries and biofuel production sectors.

REFERENCES

1. Bailey, M. J., P. Biely, and K. Poutanen. 1992. Interlaboratory testing of methods for assay of xylanase activity. J. Biotechnol. 23:257-270.

2. Bartolome, B., C. B. Faulds, P. A. Kroon, K. Waldron, H. J. Gilbert, G. Hazlewood, and G. Williamson. 1997. An *Aspergillus niger* esterase (ferulic acid esterase III) and a recombinant *Pseudomonas fluorescens* subsp. cellulosa esterase (XylD) release a 5-5' ferulic dehydrodimer (diferulic acid) from barley and wheat cell walls. Appl. Environ. Microbiol. 63: 208-12.

3. Beguin, P. 1999. Hybrid enzymes. Curr. Opin. Biotechnol. 10:336-340.

4. Bonnin, E., L. Lesage-Meesen, C. Stentelaire, M. Asther, and J. F. Thibault. 1999. Method for obtaining *A. niger* cultures and their uses for producing ferulic acid and vanillic acid. Patent No. 99/04644.

5. Bonnin, E., L. Saulnier, M. Brunel, C. Marot, L. Lesage-Meessen, M. Asther and J. F. Thibault. 2002. Release of ferulic acid from agroindustrial by-products by the cell wall-degrading enzymes produced by *Aspergillus niger* I-1472. Enzyme Microb. Technol. 31:1000-1005.

6. Bunzel, M., J. Ralph, J. M. Marita, R. D. Hatfield, and H. Steinhart. 2001. Diferulates as structural components in soluble and insoluble cereal dietary fibre. J. Sci. Food Agric. 81: 653-660.

7. Chanliaud E., L. Saulnier, and J. F. Thibault. 1995. Alkaline extraction and characterisation of heteroxylans from maize bran. J. Cereal Sci., 21:195-203.

8. Conesa, A., P. J. Punt, N. van Luijk and C. A. M. J. J. van den Hondel. 2001. The Secretion Pathway in Filamentous Fungi: A Biotechnological View. Fungal Genet. Biol. 33:155-171.

9. de Vries, R., H. C. M. Kester, C. H. Poulsen, J. A. E. Benen, and J. Visser. 2000. Synergy between enzymes from *Aspergillus* involved in the degradation of plant cell wall polysaccharides. Carbohydr. Res. 327: 401-410.

10. de Vries R. P., B. Michelsen, C. H. Poulsen., P. A. Kroon, R. H. H. van den Heuvel, C. B. Faulds, G. Williamson, J. P. T. W. van den Hombergh, and J. Visser. 1997. The faeA genes from *Aspergillus niger* and *Aspergillus tubingensis* encode ferulic acid esterases involved in degradation of complex cell wall polysaccharides. Appl. Environ. Microbiol. 63:4638-4644.

11. de Vries R. P., P. A. van Kuyk, H. C. Kester, and J. Visser. 2002. The *Aspergillus niger* faeB gene encodes a second feruloyl esterase involved in pectin and xylan degradation and is specifically induced in the presence of aromatic compounds. Biochem J. 363:377-86.

12. de Vries, R. P., and J. Visser. 2001. *Aspergillus* enzymes involved in degradation of plant cell wall polysaccharides. Microbiol. Mol. Biol. Rev. 65: 497-522.

13. Din, N., Damude, H. G., N. R. Gilkes, R. C. Jr. Miller, R. A. Warren, and D. G. Kilburn. 1994. C1-Cx revisited: intramolecular synergism in a cellulase. Proc. Natl. Acad. Sci. U.S.A. 91:11383-11387.

14. Din, N., N. R. Gilkes, B. Tekant, R. C. Jr. Miller, R. A. J. Warren, and D. G. Kilburn. 1991. Non-hydrolytic disruption of cellulose fibres by the binding domain of a bacterial cellulose. Biotechnology (N.Y.) 9:1096-1099.

15. Faulds, C. B., and G. Williamson. 1995. Release of ferulic acid from wheat bran by a ferulic acid esterase (FAE-III from *Aspergillus niger*. Appl. Microbiol. Biotechnol. 463: 1082-1087.

16. Faulds, C. B., and G. Williamson. 1999. Effect of hydroxycinnamates and benzoates on the production of feruloyl esterases by *Aspergillus niger*. J. Sci. Food Agric. 79: 450-452.

17. Fierobe, H. P., F. Mingardon, A. Mechaly, A. Belaich, M. T. Rincon, S. Pages, R. Lamed, C. Tardif, J. P. Belaich, and E. A. Bayer. 2005. Action of designer cellulosomes on homogeneous versus complex substrates: controlled incorporation of three distinct enzymes into a defined trifunctional scaffoldin. J Biol Chem 280:16325-34.

18. Garcia-Conesa, M. T., V. F. Crepin, A. J. Goldson, G. Williamson, N. J. Cummings, I. F. Connerton, C. B. Faulds, and P. A. Kroon. 2004. The feruloyl esterase system of *Talaromyces stipitatus:* production of three discrete feruloyl esterases, including a novel enzyme, TsFaeC, with a broad substrate specificity. J Biotechnol. 108:227-241.

19. Gasteiger, E., C. Hoogland, A. Gattiker, S. Duvaud, M. R. Wilkins, R. D. Appel, and A. Bairoch. 2005. Protein Identification and Analysis Tools on the ExPASy Server. John M. Walker (ed): The Proteomics Protocols Handbook, Humana Press.

20. Gielkens, M. M., E. Dekkers, J. Visser, and L. H. de Graaff. 1999. Two cellobiohydrolase-encoding genes from *Aspergillus niger* require D-xylose and the xylanolytic transcriptional activator XlnR for their expression. Appl. Environ. Microbiol. 65:4340-5.

21. Goldstein, M. A., M. Takagi, S. Hashida, O. Shoseyov, R. H. Doi, and I. H. Segel. 1993. Characterization of the cellulose-binding domain of the *Clostridium cellulovorans* cellulose-binding protein A. J. Bacteriol. 175:5762-5768.

22. Gordon, C. L., D. B. Archer, D. J. Jeenes, J. H. Doonan, B. Wells, A. P. J. Trinci, and G. D. Robson. 2000. A glucoamylase:: GFP gene fusion to study protein secretion by individual hyphae of *Aspergillus niger*. J. Microbiol. Methods. 42:39-48.

23. Graf, E. 1992. Antioxidant potential of ferulic acid. Free Radic. Biol. Med. 13:435-448.

24. Juge, N., G. Williamson, A. Puigserver, N. J. Cummings, I. F. Connerton, and C. B. Faulds. 2001. High-level production of recombinant *Aspergillus niger* cinnamoyl esterase (FAEA) in the methylotrophic yeast *Pichia pastoris*. FEMS Yeast Res. 1:127-132.

25. Ho, S. N., H. D. Hunt, R. M. Horton, J. K. Pullen, L. R. Pease. 1989. Site-directed mutagenesis by overlap extension using the polymerase chain reaction. Gene. 77:51-59.

26. Kikuzaki, H., M. Hisamoto, K. Hirose, K. Akiyama, and H. Taniguchi. 2002. Antioxidant Properties of Ferulic Acid and Its Related Compounds. J. Agric. Food Chem. 50:2161-2168.

27. Kroon, P. A., G. Williamson, N. M. Fish, D. B. Archer, and N. J. Belshaw. 2000. A modular esterase from *Penicillium funiculosum* which releases ferulic acid from plant cell walls and binds crystalline cellulose contains a carbohydrate binding module. Eur. J. Biochem. 267:6740-6752.

28. Laemmli, U. K. 1970. Cleavage of structural proteins during the assembly of the head of bacteriophage T4. Nature. 227:680-685.

29. Levasseur, A., M. Asther, and E. Record. 2005. Overproduction and characterization of xylanase B from *Aspergillus niger*. Can. J. Microbiol. 51:177-183.

30. Levasseur, A., I. Benoit, M. Asther, M. Asther, and E. Record. 2004. Homologous expression of the feruloyl esterase B gene from *Aspergillus niger* and characterization of the recombinant enzyme. Protein Expr. Purif. 37:126-133.

31. Levasseur, A., S. Pagès, H. P. Fierobe, D. Navarro, P. J. Punt, J. P. Belaïch, M. Asther and E. Record. 2004. Design and production in *Aspergillus niger* of a chimeric protein associating a fungal feruloyl esterase and a clostridial dockerin domain. Appl. Environ. Microbiol. 70:6984-6991.

32. Libby, C. B., C. A. Cornett, P. J. Reilly, and C. Ford. 1994. Effect of amino acid deletions in the O-glycosylated region of *Aspergillus awamori* glucoamylase. Protein Eng. 7:1109-1114.

33. Linder, M., and T. T. Teeri. 1997. The roles and function of cellulose-binding domains. J. Biotechnol. 57:15-28.

34. Lowry, O. H., N. J. Rosebrough, A. L. Farr, and R. J. Randall. 1951. Protein measurement with the Folin phenol reagent. J. Biol. Chem. 193:265-275.

35. Miller, G. L. 1959. Use of dinitrosalicylic acid reagent for determination of reducing sugar. Anal. Chem. 31:426-428.

36. Nixon, A. E., M. Ostermeier, and S. J. Benkovic. 1998. Hybrid enzymes: manipulating enzyme design. Trends Microbiol. 16: 258-264.

37. Pagès, S., L. Gal, A. Belaich, C. Gaudin, C. Tardif, and J. P. Belaich. 1997. Role of scaffolding protein CipC of *Clostridium cellulolyticum* in cellulose degradation. J. Bacteriol. 179:2810-2816.

38. Porath, J., J. Carlsson, I. Olsson, G. Belfrage. 1975. Metal chelate affinity chromatography, a new approach to protein fractionation. Nature. 258:598-599.

39. Punt, P. J., and C. A. van den Hondel. 1992. Transformation of filamentous fungi based on hygromycin B and phleomycine resistance markers. Meth Enzymol 216:447-457.

40. Ralet, M. C., C. B. Faulds, G. Williamson, and J. F. Thibault. 1994. Degradation of feruloylated oligosaccharides from sugar-beet pulp and wheat bran by ferulic acid esterases from *Aspergillus niger*. Carbohydr. Res. 263:257-269.

41. Record, E., M. Asther, C. Sigoillot, S. Pagès, P. J. Punt, M. Delattre, M. Haon, C. A. van den Hondel, J. C. Sigoillot, L. Lesage-Meessen, and M. Asther. 2003. Overproduction of the *Aspergillus niger* feruloyl esterase for pulp bleaching application. Appl. Microbiol. Biotechnol. 62:349-355.

42. Sagt, C. M., B. Kleizen, R. Verwaal, M. D. deJong, W. H. Muller, A. Smits, C. Visser, J. Boonstra, A. J. Verkleij, and C. T. Verrips. 2000. Introduction of N-glycosylation site increases secretion of heterologous proteins in yeasts. Appl. Environ. Microbiol. 66:4940-4944.

43. Saulnier, L. and J. F. Thibault. 1999. Ferulic acid and diferulic acids as components of sugar-beet pectins and maize bran heteroxylans. J. Sci. Food Agric. 79: 396-402.

44. Shibuya, I., G. Tamura, H. Shima, T. Ishikawa, and S. Hara. 1992. Construction of an α-amylase/glucoamylase fusion gene and its expression in *Saccharomyces cerevisiae*. Biosci. Biotech. Biochem. 56:884-889.

45. Srisodsuk, M., J. Lehtio, M. Linder, E. Margolles-Clark, and T. Reinikainen, T. T. Teeri. 1997. *Trichoderma reesei* cellobiohydrolase I with an endoglucanase cellulose-binding domain: action on bacterial microcrystalline cellulose. J. Biotechnol. 57:49-57.

46. Tomme, P. N., R. Gilkes, C. M. Jr. Miller, A. J. Warren and D. G. Kilburn. 1994. An internal cellulose-binding domain mediates adsorption of an engineered bifunctional xylanase/cellulase. Protein Eng. 7:117-123.

47. Topakas, E., H. Stamatis, P. Biely, and P. Christakopoulos. 2004. Purification and characterization of a type B feruloyl esterase (StFAE-A) from the thermophilic fungus *Sporotrichum thermophile*. Appl. Microbiol. Biotechnol. 63:686-690.

48. van Hartingsveldt, W., I. E. Mattern, C. M. van Zeijl, P. H. Pouwells, and C. A. van den Hondel. 1987. Development of a homologous transformation system for *Aspergillus niger* based on the pyrG gene. Mol. Gen. Genet. 206:71-75.

49. Wood, T. M. 1988. Preparation of crystalline, amorphous, and dyed cellulase substrates Meth. Enzymol. 160:19-25.

50. Yu, P., D. D. Maenz, J. J. McKinnon, V. J. Racz, and D. A. Christensen. 2002. Release of Ferulic Acid from Oat Hulls by *Aspergillus* Ferulic Acid Esterase and *Trichoderma* xylanase, J Agric Food Chem 50:1625-1630.

FIGURES

FIG. 1. Expression cassettes used in this study. In order to design the FLX insert (A), the *A. niger* sequences coding for FAEA, a linker region from CBHB and XYNB, were fused together. In the second construction (B), the FLX template was fused to the cbhb sequence encoding the linker sequence and CBM generating the FLXLC insert. Expression cassettes are under the control of the gpdA promoter and trpC terminator. Both constructions contained a six histidines-encoding sequence at the 3' end.

(1) Linker-encoding sequence:

```
GSTYSSGSSSGSGSSSSSSSTTTKATSTTLKTTSTTSSGSSSTSAA.
```

FIG. 2. Time course activities of extracellular feruloyl esterase and xylanase in *A. niger*. Feruloyl esterase (A) and xylanase (B) activities were measured for the best FLX (♦) and FLXLC (■) transformant. Activities were determined by using MFA and birchwood xylan as substrates for esterase and xylanase activities, respectively.

FIG. 3. SDS-PAGE of extracellular proteins produced by FLX and FLXLC transformants.

Total and purified proteins from FLX (lanes 1 and 2, respectively) and FLXLC (lanes 3 and 4, respectively) were loaded onto a SDS-PAGE (11% polyacrylamide). Gel was stained with Coomassie blue. SD: molecular mass standards.

FIG. 4. Western blot analysis of total and purified proteins produced by FLX and FLXLC transformants. Antibodies raised against FAEA (A) or His-Tag (B) were used for immunodetection of the total extracellular and purified proteins from FLX and FLXLC transformants. Lanes 1,5: total extracellular proteins from FLX transformant. Lanes 2,6: purified FLX. Lanes 3,7: total extracellular proteins from FLXLC transformant. Lanes 4,8: purified FLXLC. C: control strain D15#26 transformed with pAB4-1. Detection was performed by chemiluminescence.

FIG. 5. Comparison of the ferulic acid release efficiency by action of free or bifunctional enzymes. Wheat bran (A) and maize bran (B) were used for the FA hydrolysis by free or bifunctional enzymes. FA release was determined by HPLC after 4 h (white bars) and 16 h (black bars). Activities were expressed as the percentage of the total amount of FA present in the substrate. The standard deviation was less than 5% from the mean of the value for WB and MB.

TABLE 1

Physico-chemical and kinetic parameters for the feruloyl esterase and xylanase partners.

| | Feruloyl esterase activity | | | Xylanase acitivity | | |
|---|---|---|---|---|---|---|
| | FAEA[1] | FLX | FLXLC | XYNB[2] | FLX | FLXFC |
| Tp optimum | 60° C. | 55-60° C. | 55-60° C. | 50° C. | 45° C. | 45° C. |
| Tp stability | — | 45° C. | 45° C. | 50° C. | 45° C. | 45° C. |
| pH optimum | 5 | 5 | 5 | 5.5 | 6 | 6 |
| pH stability | 5-6 | 5-6 | 5-6 | 4-7 | 4-7 | 4-7 |
| $K_m$[3] | 0.75 | 0.80 | 0.78 | 6.6 | 7.5 | 7.5 |
| Specific activity[4] | 0.72 | 0.66 | 0.63 | 386 | 394 | 368 |

[1],[2](References 41 and 29, respectively).
[3]$K_m$ were expressed in molar for the feruloyl esterase activity and in milligram per millilitre for the xylanase activity.
[4]Specific activities were expressed in nkatal per nmole of protein, in order to facilitate comparison between free and bifunctional proteins.
For the pH and temperature stabilities, incubation were performed for 90 minutes.

TABLE 2

Comparison of the synergistic effect on the ferulic acid release between free and fused enzymes.

| | WB | | MB | |
|---|---|---|---|---|
| | 4 h | 16 h | 4 h | 16 h |
| FLX | 1.95 | 1.85 | 1.53 | 1.30 |
| FLXLC | 1.95 | 1.85 | 1.80 | 1.62 |

The synergy factor is defined as: (released FA by the bifunctional enzymes FLX or FLXLC)/(released FA by the free enzymes FAEA + XYNB).

The invention claimed is:

1. A fusion protein comprising a feruloyl esterase, a xylanase, a hyperglycosylated linker, and optionally a C-terminal carbohydrate-binding-module (CBM), the fusion protein selected from the group consisting of:
- a fusion protein comprising the feruloyl esterase as set forth in SEQ ID NO: 2, the xylanase as set forth in SEQ ID NO: 6, and the hyperglycosylated linker between the feruloyl esterase and the xylanase,
- a fusion protein comprising the feruloyl esterase as set forth in SEQ ID NO: 2, the xylanase as set forth in SEQ ID NO: 6, the CBM as set forth in SEQ ID NO: 8, and the hyperglycosylated linker between each of the feruloyl esterase, the xylanase, and the CBM,
- a fusion protein comprising the feruloyl esterase as set forth in SEQ ID NO: 4, the xylanase as set forth in SEQ ID NO: 6, and the hyperglycosylated linker between the feruloyl esterase and the xylanase,
- a fusion protein comprising the feruloyl esterase as set forth in SEQ ID NO: 4, the xylanase as set forth in SEQ ID NO: 6, the CBM as set forth in SEQ ID NO: 8, and the hyperglycosylated linker between each of the feruloyl esterase, the xylanase, and the CBM.

2. The fusion protein according to claim 1, wherein the hyperglycosylated linker comprises SEQ ID NO: 10.

3. The fusion protein according to claim 1, comprising SEQ ID NO: 12.

4. The fusion protein according to claim 1, comprising SEQ ID NO: 14.

5. The fusion protein according to claim 1, comprising SEQ ID NO: 16.

6. The fusion protein according to claim 1, comprising SEQ ID NO: 18.

* * * * *

SEQUENCE LISTING

<160> NUMBER OF SEQ ID NOS: 30

<210> SEQ ID NO 1
<211> LENGTH: 780
<212> TYPE: DNA
<213> ORGANISM: Aspergillus niger
<220> FEATURE:
<221> NAME/KEY: CDS
<222> LOCATION: (1)..(780)
<223> OTHER INFORMATION:

<400> SEQUENCE: 1

```
gcc tcc acg caa ggc atc tcc gaa gac ctc tac aat cgc ttg gta gag     48
Ala Ser Thr Gln Gly Ile Ser Glu Asp Leu Tyr Asn Arg Leu Val Glu
1               5                   10                  15 atg gcc act atc tcc caa gcc gcc tac gcc gac cta tgc aat att cca     96
Met Ala Thr Ile Ser Gln Ala Ala Tyr Ala Asp Leu Cys Asn Ile Pro
            20                  25                  30 tcg act att atc aaa gga gag aaa att tac aac gct caa act gat atc    144
Ser Thr Ile Ile Lys Gly Glu Lys Ile Tyr Asn Ala Gln Thr Asp Ile
        35                  40                  45 aac gga tgg atc ctc cgc gac gac acc agc aaa gaa att atc acc gtc    192
Asn Gly Trp Ile Leu Arg Asp Asp Thr Ser Lys Glu Ile Ile Thr Val
    50                  55                  60 ttc cgt ggc act ggc agt gac aca aac cta cag ctc gat act aac tac    240
Phe Arg Gly Thr Gly Ser Asp Thr Asn Leu Gln Leu Asp Thr Asn Tyr
65                  70                  75                  80 acg ctc acg cca ttc gac act cta cct caa tgc aac gat tgc gag gta    288
Thr Leu Thr Pro Phe Asp Thr Leu Pro Gln Cys Asn Asp Cys Glu Val
                85                  90                  95 cac ggt gga tac tat att gga tgg atc tca gtc caa gac caa gtc gag    336
```

```
His Gly Gly Tyr Tyr Ile Gly Trp Ile Ser Val Gln Asp Gln Val Glu
            100                 105                 110 tcg ctt gtc aaa caa cag gct agc cag tat ccg gac tat gcg ctt acc      384
Ser Leu Val Lys Gln Gln Ala Ser Gln Tyr Pro Asp Tyr Ala Leu Thr
            115                 120                 125 gtg aca ggc cat agt ctg gga gcg tcg atg gca gca ctc act gcc gcc      432
Val Thr Gly His Ser Leu Gly Ala Ser Met Ala Ala Leu Thr Ala Ala
            130                 135                 140 cag ctg tcc gcg aca tac gac aac gtc cgt ctg tac aca ttc ggc gaa      480
Gln Leu Ser Ala Thr Tyr Asp Asn Val Arg Leu Tyr Thr Phe Gly Glu
145                 150                 155                 160 ccg cgc agc ggc aac cag gcc ttc gcg tcg tac atg aac gat gcg ttc      528
Pro Arg Ser Gly Asn Gln Ala Phe Ala Ser Tyr Met Asn Asp Ala Phe
                165                 170                 175 cag gtc tcg agc ccg gag acg acc cag tac ttc cgg gtc act cat tcc      576
Gln Val Ser Ser Pro Glu Thr Thr Gln Tyr Phe Arg Val Thr His Ser
                180                 185                 190 aac gac ggc atc cca aac ttg ccc ccg gcg gac gag ggt tac gcc cat      624
Asn Asp Gly Ile Pro Asn Leu Pro Pro Ala Asp Glu Gly Tyr Ala His
                195                 200                 205 ggt ggt gta gag tac tgg agc gtt gat cct tac agc gcc cag aac acg      672
Gly Gly Val Glu Tyr Trp Ser Val Asp Pro Tyr Ser Ala Gln Asn Thr
210                 215                 220 ttt gtc tgt act ggg gat gaa gta cag tgc tgt gag gca cag ggc gga      720
Phe Val Cys Thr Gly Asp Glu Val Gln Cys Cys Glu Ala Gln Gly Gly
225                 230                 235                 240 cag ggg gtg aat gat gcg cat act act tat ttt ggg atg acg agc gga      768
Gln Gly Val Asn Asp Ala His Thr Thr Tyr Phe Gly Met Thr Ser Gly
                245                 250                 255 gct tgt act tgg                                                      780
Ala Cys Thr Trp
            260

<210> SEQ ID NO 2
<211> LENGTH: 260
<212> TYPE: PRT
<213> ORGANISM: Aspergillus niger

<400> SEQUENCE: 2

Ala Ser Thr Gln Gly Ile Ser Glu Asp Leu Tyr Asn Arg Leu Val Glu
1               5                   10                  15

Met Ala Thr Ile Ser Gln Ala Ala Tyr Ala Asp Leu Cys Asn Ile Pro
            20                  25                  30

Ser Thr Ile Lys Gly Glu Lys Ile Tyr Asn Ala Gln Thr Asp Ile
            35                  40                  45

Asn Gly Trp Ile Leu Arg Asp Asp Thr Ser Lys Glu Ile Ile Thr Val
    50                  55                  60

Phe Arg Gly Thr Gly Ser Asp Thr Asn Leu Gln Leu Asp Thr Asn Tyr
65                  70                  75                  80

Thr Leu Thr Pro Phe Asp Thr Leu Pro Gln Cys Asn Asp Cys Glu Val
                85                  90                  95

His Gly Gly Tyr Tyr Ile Gly Trp Ile Ser Val Gln Asp Gln Val Glu
            100                 105                 110

Ser Leu Val Lys Gln Gln Ala Ser Gln Tyr Pro Asp Tyr Ala Leu Thr
            115                 120                 125

Val Thr Gly His Ser Leu Gly Ala Ser Met Ala Ala Leu Thr Ala Ala
            130                 135                 140

Gln Leu Ser Ala Thr Tyr Asp Asn Val Arg Leu Tyr Thr Phe Gly Glu
145                 150                 155                 160
```

```
Pro Arg Ser Gly Asn Gln Ala Phe Ala Ser Tyr Met Asn Asp Ala Phe
            165                 170                 175

Gln Val Ser Ser Pro Glu Thr Thr Gln Tyr Phe Arg Val Thr His Ser
        180                 185                 190

Asn Asp Gly Ile Pro Asn Leu Pro Pro Ala Asp Glu Gly Tyr Ala His
            195                 200                 205

Gly Gly Val Glu Tyr Trp Ser Val Asp Pro Tyr Ser Ala Gln Asn Thr
        210                 215                 220

Phe Val Cys Thr Gly Asp Glu Val Gln Cys Cys Glu Ala Gln Gly Gly
225                 230                 235                 240

Gln Gly Val Asn Asp Ala His Thr Thr Tyr Phe Gly Met Thr Ser Gly
            245                 250                 255

Ala Cys Thr Trp
            260

<210> SEQ ID NO 3
<211> LENGTH: 1512
<212> TYPE: DNA
<213> ORGANISM: Aspergillus niger
<220> FEATURE:
<221> NAME/KEY: CDS
<222> LOCATION: (1)..(1512)
<223> OTHER INFORMATION:

<400> SEQUENCE: 3 gcg acc gac ccc ttc cag tcg cgg tgc aat gaa ttc cag aac aag atc      48
Ala Thr Asp Pro Phe Gln Ser Arg Cys Asn Glu Phe Gln Asn Lys Ile
1               5                  10                  15 gac atc gcc aat gtc acc gtc aga tcg gtc gca tac gtt gct gct gga      96
Asp Ile Ala Asn Val Thr Val Arg Ser Val Ala Tyr Val Ala Ala Gly
            20                  25                  30 cag aac atc tcc caa gcg gag gtc gcc tcc gtg tgt aaa gca tcg gtt     144
Gln Asn Ile Ser Gln Ala Glu Val Ala Ser Val Cys Lys Ala Ser Val
        35                  40                  45 caa gcc agt gtc gac ctg tgc cgg gta acc atg aac atc tcg acg tcg     192
Gln Ala Ser Val Asp Leu Cys Arg Val Thr Met Asn Ile Ser Thr Ser
    50                  55                  60 gat cgc agc cat ctg tgg gct gag gcc tgg ctc cca aga aat tat acc     240
Asp Arg Ser His Leu Trp Ala Glu Ala Trp Leu Pro Arg Asn Tyr Thr
65                  70                  75                  80 ggt cgc ttc gtg agc acg ggg aat gga ggt cta gcc ggc tgt gtc caa     288
Gly Arg Phe Val Ser Thr Gly Asn Gly Gly Leu Ala Gly Cys Val Gln
                85                  90                  95 gaa acg gac ctc aac ttt gca gcc aac ttt ggt ttc gct acc gtg ggc     336
Glu Thr Asp Leu Asn Phe Ala Ala Asn Phe Gly Phe Ala Thr Val Gly
            100                 105                 110 acc aac ggt gga cat gac ggg gac acg gcc aaa tac ttc ctc aac aac     384
Thr Asn Gly Gly His Asp Gly Asp Thr Ala Lys Tyr Phe Leu Asn Asn
        115                 120                 125 tcg gag gtt ctg gcc gat ttt gcc tat cgc tca gtg cac gaa ggg acc     432
Ser Glu Val Leu Ala Asp Phe Ala Tyr Arg Ser Val His Glu Gly Thr
    130                 135                 140 gtg gtg ggt aag caa cta act caa ttg ttt tat gac gag gga tac aac     480
Val Val Gly Lys Gln Leu Thr Gln Leu Phe Tyr Asp Glu Gly Tyr Asn
145                 150                 155                 160 tac tcc tac tat ttg ggt tgc tcc acc gga ggc cgc caa ggc tac cag     528
Tyr Ser Tyr Tyr Leu Gly Cys Ser Thr Gly Gly Arg Gln Gly Tyr Gln
                165                 170                 175 caa gtc caa cgg ttt ccc gac gac tat gac gga gtg att gcg ggc tcc     576
Gln Val Gln Arg Phe Pro Asp Asp Tyr Asp Gly Val Ile Ala Gly Ser
```

```
                    180                 185                 190
gca gcg atg aac ttt atc aac ctg atc tcc tgg ggg gcc ttc ttg tgg    624
Ala Ala Met Asn Phe Ile Asn Leu Ile Ser Trp Gly Ala Phe Leu Trp
        195                 200                 205 aag gcg acg ggg tta gcg gat gat cca gac ttt atc tct gca aac ctg    672
Lys Ala Thr Gly Leu Ala Asp Asp Pro Asp Phe Ile Ser Ala Asn Leu
210                 215                 220 tgg tcc gta atc cac cag gag att gtt cgt cag tgc gac ctg gtc gat    720
Trp Ser Val Ile His Gln Glu Ile Val Arg Gln Cys Asp Leu Val Asp
225                 230                 235                 240 ggg gct ctg gat gga atc atc gaa gac cct gat ttc tgt gct cca gtc    768
Gly Ala Leu Asp Gly Ile Ile Glu Asp Pro Asp Phe Cys Ala Pro Val
                245                 250                 255 atc gag cgc ttg atc tgc gac ggg act acc aac ggc acc tct tgt atc    816
Ile Glu Arg Leu Ile Cys Asp Gly Thr Thr Asn Gly Thr Ser Cys Ile
            260                 265                 270 acg gga gcc cag gca gca aag gtc aac cgg gcc ttg agt gac ttc tat    864
Thr Gly Ala Gln Ala Ala Lys Val Asn Arg Ala Leu Ser Asp Phe Tyr
        275                 280                 285 ggc ccc gac ggg aca gtg tac tac ccg cgc ctg aac tat ggg ggt gag    912
Gly Pro Asp Gly Thr Val Tyr Tyr Pro Arg Leu Asn Tyr Gly Gly Glu
290                 295                 300 gcc gac tcg gct tcc ctg tac ttc acg ggg tcg atg tac agc cgt acg    960
Ala Asp Ser Ala Ser Leu Tyr Phe Thr Gly Ser Met Tyr Ser Arg Thr
305                 310                 315                 320 gag gaa tgg tac aaa tat gtg gtc tat aac gac acc aac tgg aac tcc   1008
Glu Glu Trp Tyr Lys Tyr Val Val Tyr Asn Asp Thr Asn Trp Asn Ser
                325                 330                 335 agc cag tgg acg ctg gag agt gcc aag ctg gcc ctg gag cag aat ccg   1056
Ser Gln Trp Thr Leu Glu Ser Ala Lys Leu Ala Leu Glu Gln Asn Pro
            340                 345                 350 ttc aat atc cag gcg ttt gat ccc aac atc acg gcc ttc cgg gac cgg   1104
Phe Asn Ile Gln Ala Phe Asp Pro Asn Ile Thr Ala Phe Arg Asp Arg
        355                 360                 365 ggt ggc aag ctg ctg tcc tac cac ggc acg cag gat ccc att atc agc   1152
Gly Gly Lys Leu Leu Ser Tyr His Gly Thr Gln Asp Pro Ile Ile Ser
370                 375                 380 tcc acg gat agc aag ctc tac tac cga cgg gta gcc aat gcc ctg aat   1200
Ser Thr Asp Ser Lys Leu Tyr Tyr Arg Arg Val Ala Asn Ala Leu Asn
385                 390                 395                 400 gcc gcg ccg tcc gag cta gat gag ttc tat cgg ttc ttc cag atc tcc   1248
Ala Ala Pro Ser Glu Leu Asp Glu Phe Tyr Arg Phe Phe Gln Ile Ser
                405                 410                 415 ggc atg ggc cac tgt ggc gat ggc acg gga gca tcg tac atc ggc cag   1296
Gly Met Gly His Cys Gly Asp Gly Thr Gly Ala Ser Tyr Ile Gly Gln
            420                 425                 430 gga tat ggc acg tac acc tcc aag gcg ccc caa gtc aac ctg ctg cgc   1344
Gly Tyr Gly Thr Tyr Thr Ser Lys Ala Pro Gln Val Asn Leu Leu Arg
        435                 440                 445 acg atg gtg gac tgg gtg gaa aac gga aag gcg ccc gag tat atg ccg   1392
Thr Met Val Asp Trp Val Glu Asn Gly Lys Ala Pro Glu Tyr Met Pro
450                 455                 460 ggc aac aag ctc aac gcg aac ggg tca att gag tac atg cgc aag cac   1440
Gly Asn Lys Leu Asn Ala Asn Gly Ser Ile Glu Tyr Met Arg Lys His
465                 470                 475                 480 tgc cgg tat ccg aag cat aac att cac acg ggg ccg ggt aac tac acc   1488
Cys Arg Tyr Pro Lys His Asn Ile His Thr Gly Pro Gly Asn Tyr Thr
                485                 490                 495 gat cct aac tcc tgg act tgc gta                                   1512
Asp Pro Asn Ser Trp Thr Cys Val
```

<210> SEQ ID NO 4
<211> LENGTH: 504
<212> TYPE: PRT
<213> ORGANISM: Aspergillus niger

<400> SEQUENCE: 4

```
Ala Thr Asp Pro Phe Gln Ser Arg Cys Asn Glu Phe Gln Asn Lys Ile
1               5                   10                  15

Asp Ile Ala Asn Val Thr Val Arg Ser Val Ala Tyr Val Ala Ala Gly
            20                  25                  30

Gln Asn Ile Ser Gln Ala Glu Val Ala Ser Val Cys Lys Ala Ser Val
        35                  40                  45

Gln Ala Ser Val Asp Leu Cys Arg Val Thr Met Asn Ile Ser Thr Ser
    50                  55                  60

Asp Arg Ser His Leu Trp Ala Glu Ala Trp Leu Pro Arg Asn Tyr Thr
65                  70                  75                  80

Gly Arg Phe Val Ser Thr Gly Asn Gly Gly Leu Ala Gly Cys Val Gln
                85                  90                  95

Glu Thr Asp Leu Asn Phe Ala Ala Asn Phe Gly Phe Ala Thr Val Gly
            100                 105                 110

Thr Asn Gly Gly His Asp Gly Asp Thr Ala Lys Tyr Phe Leu Asn Asn
        115                 120                 125

Ser Glu Val Leu Ala Asp Phe Ala Tyr Arg Ser Val His Glu Gly Thr
    130                 135                 140

Val Val Gly Lys Gln Leu Thr Gln Leu Phe Tyr Asp Glu Gly Tyr Asn
145                 150                 155                 160

Tyr Ser Tyr Tyr Leu Gly Cys Ser Thr Gly Gly Arg Gln Gly Tyr Gln
                165                 170                 175

Gln Val Gln Arg Phe Pro Asp Asp Tyr Asp Gly Val Ile Ala Gly Ser
            180                 185                 190

Ala Ala Met Asn Phe Ile Asn Leu Ile Ser Trp Gly Ala Phe Leu Trp
        195                 200                 205

Lys Ala Thr Gly Leu Ala Asp Asp Pro Asp Phe Ile Ser Ala Asn Leu
    210                 215                 220

Trp Ser Val Ile His Gln Glu Ile Val Arg Gln Cys Asp Leu Val Asp
225                 230                 235                 240

Gly Ala Leu Asp Gly Ile Ile Glu Asp Pro Asp Phe Cys Ala Pro Val
                245                 250                 255

Ile Glu Arg Leu Ile Cys Asp Gly Thr Thr Asn Gly Thr Ser Cys Ile
            260                 265                 270

Thr Gly Ala Gln Ala Ala Lys Val Asn Arg Ala Leu Ser Asp Phe Tyr
        275                 280                 285

Gly Pro Asp Gly Thr Val Tyr Tyr Pro Arg Leu Asn Tyr Gly Gly Glu
    290                 295                 300

Ala Asp Ser Ala Ser Leu Tyr Phe Thr Gly Ser Met Tyr Ser Arg Thr
305                 310                 315                 320

Glu Glu Trp Tyr Lys Tyr Val Val Tyr Asn Asp Thr Asn Trp Asn Ser
                325                 330                 335

Ser Gln Trp Thr Leu Glu Ser Ala Lys Leu Ala Leu Glu Gln Asn Pro
            340                 345                 350

Phe Asn Ile Gln Ala Phe Asp Pro Asn Ile Thr Ala Phe Arg Asp Arg
        355                 360                 365

Gly Gly Lys Leu Leu Ser Tyr His Gly Thr Gln Asp Pro Ile Ile Ser
```

-continued

```
                    370                 375                 380
Ser Thr Asp Ser Lys Leu Tyr Tyr Arg Val Ala Asn Ala Leu Asn
385                 390                 395                 400

Ala Ala Pro Ser Glu Leu Asp Glu Phe Tyr Arg Phe Gln Ile Ser
                405                 410                 415

Gly Met Gly His Cys Gly Asp Gly Thr Gly Ala Ser Tyr Ile Gly Gln
                420                 425                 430

Gly Tyr Gly Thr Tyr Thr Ser Lys Ala Pro Gln Val Asn Leu Leu Arg
                435                 440                 445

Thr Met Val Asp Trp Val Glu Asn Gly Lys Ala Pro Glu Tyr Met Pro
450                 455                 460

Gly Asn Lys Leu Asn Ala Asn Gly Ser Ile Glu Tyr Met Arg Lys His
465                 470                 475                 480

Cys Arg Tyr Pro Lys His Asn Ile His Thr Gly Pro Gly Asn Tyr Thr
                485                 490                 495

Asp Pro Asn Ser Trp Thr Cys Val
                500

<210> SEQ ID NO 5
<211> LENGTH: 564
<212> TYPE: DNA
<213> ORGANISM: Aspergillus niger
<220> FEATURE:
<221> NAME/KEY: CDS
<222> LOCATION: (1)..(564)
<223> OTHER INFORMATION:

<400> SEQUENCE: 5 tcg acc ccg agc tcg acc ggc gag aac aac ggc ttc tac tac tcc ttc      48
Ser Thr Pro Ser Ser Thr Gly Glu Asn Asn Gly Phe Tyr Tyr Ser Phe
1               5                   10                  15 tgg acc gac ggc ggt gga gac gtg acc tac acc aac gga gat gct ggt      96
Trp Thr Asp Gly Gly Gly Asp Val Thr Tyr Thr Asn Gly Asp Ala Gly
            20                  25                  30 gcc tac act gtt gag tgg tcc aac gtg ggc aac ttt gtc ggt gga aag     144
Ala Tyr Thr Val Glu Trp Ser Asn Val Gly Asn Phe Val Gly Gly Lys
        35                  40                  45 ggc tgg aac ccc gga agt gcg cag gac atc acc tac agc ggc acc ttc     192
Gly Trp Asn Pro Gly Ser Ala Gln Asp Ile Thr Tyr Ser Gly Thr Phe
    50                  55                  60 acc cct agc ggc aac ggc tac ctc tcc gtc tat ggc tgg acc act gac     240
Thr Pro Ser Gly Asn Gly Tyr Leu Ser Val Tyr Gly Trp Thr Thr Asp
65                  70                  75                  80 cct ctg atc gag tac tac atc gtc gag tct tac ggc gac tac aac ccc     288
Pro Leu Ile Glu Tyr Tyr Ile Val Glu Ser Tyr Gly Asp Tyr Asn Pro
                85                  90                  95 ggc agt gga ggc acg tac aag ggc acc gtc acc tcg gac gga tcc gtt     336
Gly Ser Gly Gly Thr Tyr Lys Gly Thr Val Thr Ser Asp Gly Ser Val
            100                 105                 110 tac gat atc tac acg gct acc cgt acc aat gct gct tcc att cag gga     384
Tyr Asp Ile Tyr Thr Ala Thr Arg Thr Asn Ala Ala Ser Ile Gln Gly
        115                 120                 125 acc gct acc ttc act cag tac tgg tcc gtt cgc cag aac aag aga gtt     432
Thr Ala Thr Phe Thr Gln Tyr Trp Ser Val Arg Gln Asn Lys Arg Val
    130                 135                 140 ggc gga acc gtt acc acc tcc aac cac ttc aat gct tgg gct aag ctg     480
Gly Gly Thr Val Thr Thr Ser Asn His Phe Asn Ala Trp Ala Lys Leu
145                 150                 155                 160 gga atg aac ctg ggt act cac aac tac cag atc gtg gct acc gag ggt     528
Gly Met Asn Leu Gly Thr His Asn Tyr Gln Ile Val Ala Thr Glu Gly
```

```
                                  165                 170                 175
tac cag agc agt gga tct tcg tcc atc act gtt cag                                564
Tyr Gln Ser Ser Gly Ser Ser Ser Ile Thr Val Gln
            180                 185

<210> SEQ ID NO 6
<211> LENGTH: 188
<212> TYPE: PRT
<213> ORGANISM: Aspergillus niger

<400> SEQUENCE: 6

Ser Thr Pro Ser Ser Thr Gly Glu Asn Asn Gly Phe Tyr Tyr Ser Phe
1               5                   10                  15

Trp Thr Asp Gly Gly Gly Asp Val Thr Tyr Thr Asn Gly Asp Ala Gly
            20                  25                  30

Ala Tyr Thr Val Glu Trp Ser Asn Val Gly Asn Phe Val Gly Gly Lys
        35                  40                  45

Gly Trp Asn Pro Gly Ser Ala Gln Asp Ile Thr Tyr Ser Gly Thr Phe
    50                  55                  60

Thr Pro Ser Gly Asn Gly Tyr Leu Ser Val Tyr Gly Trp Thr Thr Asp
65                  70                  75                  80

Pro Leu Ile Glu Tyr Tyr Ile Val Glu Ser Tyr Gly Asp Tyr Asn Pro
                85                  90                  95

Gly Ser Gly Gly Thr Tyr Lys Gly Thr Val Thr Ser Asp Gly Ser Val
            100                 105                 110

Tyr Asp Ile Tyr Thr Ala Thr Arg Thr Asn Ala Ala Ser Ile Gln Gly
        115                 120                 125

Thr Ala Thr Phe Thr Gln Tyr Trp Ser Val Arg Gln Asn Lys Arg Val
    130                 135                 140

Gly Gly Thr Val Thr Thr Ser Asn His Phe Asn Ala Trp Ala Lys Leu
145                 150                 155                 160

Gly Met Asn Leu Gly Thr His Asn Tyr Gln Ile Val Ala Thr Glu Gly
                165                 170                 175

Tyr Gln Ser Ser Gly Ser Ser Ser Ile Thr Val Gln
            180                 185

<210> SEQ ID NO 7
<211> LENGTH: 102
<212> TYPE: DNA
<213> ORGANISM: Aspergillus niger
<220> FEATURE:
<221> NAME/KEY: CDS
<222> LOCATION: (1)..(102)
<223> OTHER INFORMATION:

<400> SEQUENCE: 7 cag gcg tat gga cag tgt ggt gga cag ggc tgg act ggt ccg acc act       48
Gln Ala Tyr Gly Gln Cys Gly Gly Gln Gly Trp Thr Gly Pro Thr Thr
1               5                   10                  15 tgt gtg agt ggg tac act tgc acg tat gag aat gcg tac tac tcg cag       96
Cys Val Ser Gly Tyr Thr Cys Thr Tyr Glu Asn Ala Tyr Tyr Ser Gln
            20                  25                  30 tgt ttg                                                              102
Cys Leu <210> SEQ ID NO 8
<211> LENGTH: 34
<212> TYPE: PRT
<213> ORGANISM: Aspergillus niger

<400> SEQUENCE: 8
```

```
Gln Ala Tyr Gly Gln Cys Gly Gln Gly Trp Thr Gly Pro Thr Thr
1               5                   10                  15

Cys Val Ser Gly Tyr Thr Cys Thr Tyr Glu Asn Ala Tyr Tyr Ser Gln
                20                  25                  30

Cys Leu
```

<210> SEQ ID NO 9
<211> LENGTH: 138
<212> TYPE: DNA
<213> ORGANISM: Aspergillus niger
<220> FEATURE:
<221> NAME/KEY: CDS
<222> LOCATION: (1)..(138)
<223> OTHER INFORMATION:

<400> SEQUENCE: 9

```
ggc tcg act tac tcc agt gga tct tct tcg ggg tcg ggg tct agc tcc     48
Gly Ser Thr Tyr Ser Ser Gly Ser Ser Ser Gly Ser Gly Ser Ser Ser
1               5                   10                  15 agc tcg agt tcg act acc act aag gcc act tcg acg acc ttg aag act     96
Ser Ser Ser Ser Thr Thr Thr Lys Ala Thr Ser Thr Thr Leu Lys Thr
                20                  25                  30 acc tcg acc acc agc agt gga agc agt tcg aca tcg gcg gcg            138
Thr Ser Thr Thr Ser Ser Gly Ser Ser Ser Thr Ser Ala Ala
            35                  40                  45
```

<210> SEQ ID NO 10
<211> LENGTH: 46
<212> TYPE: PRT
<213> ORGANISM: Aspergillus niger

<400> SEQUENCE: 10

```
Gly Ser Thr Tyr Ser Ser Gly Ser Ser Ser Gly Ser Gly Ser Ser Ser
1               5                   10                  15

Ser Ser Ser Ser Thr Thr Thr Lys Ala Thr Ser Thr Thr Leu Lys Thr
                20                  25                  30

Thr Ser Thr Thr Ser Ser Gly Ser Ser Ser Thr Ser Ala Ala
            35                  40                  45
```

<210> SEQ ID NO 11
<211> LENGTH: 1482
<212> TYPE: DNA
<213> ORGANISM: Aspergillus niger
<220> FEATURE:
<221> NAME/KEY: CDS
<222> LOCATION: (1)..(1482)
<223> OTHER INFORMATION:

<400> SEQUENCE: 11

```
gcc tcc acg caa ggc atc tcc gaa gac ctc tac aat cgc ttg gta gag     48
Ala Ser Thr Gln Gly Ile Ser Glu Asp Leu Tyr Asn Arg Leu Val Glu
1               5                   10                  15 atg gcc act atc tcc caa gcc gcc tac gcc gac cta tgc aat att cca     96
Met Ala Thr Ile Ser Gln Ala Ala Tyr Ala Asp Leu Cys Asn Ile Pro
                20                  25                  30 tcg act att atc aaa gga gag aaa att tac aac gct caa act gat atc    144
Ser Thr Ile Ile Lys Gly Glu Lys Ile Tyr Asn Ala Gln Thr Asp Ile
            35                  40                  45 aac gga tgg atc ctc cgc gac gac acc agc aaa gaa att atc acc gtc    192
Asn Gly Trp Ile Leu Arg Asp Asp Thr Ser Lys Glu Ile Ile Thr Val
        50                  55                  60 ttc cgt ggc act ggc agt gac aca aac cta cag ctc gat act aac tac    240
Phe Arg Gly Thr Gly Ser Asp Thr Asn Leu Gln Leu Asp Thr Asn Tyr
```

```
                65                  70                  75                  80
acg ctc acg cca ttc gac act cta cct caa tgc aac gat tgc gag gta           288
Thr Leu Thr Pro Phe Asp Thr Leu Pro Gln Cys Asn Asp Cys Glu Val
                    85                  90                  95 cac ggt gga tac tat att gga tgg atc tca gtc caa gac caa gtc gag           336
His Gly Gly Tyr Tyr Ile Gly Trp Ile Ser Val Gln Asp Gln Val Glu
                100                 105                 110 tcg ctt gtc aaa caa cag gct agc cag tat ccg gac tat gcg ctt acc           384
Ser Leu Val Lys Gln Gln Ala Ser Gln Tyr Pro Asp Tyr Ala Leu Thr
                115                 120                 125 gtg aca ggc cat agt ctg gga gcg tcg atg gca gca ctc act gcc gcc           432
Val Thr Gly His Ser Leu Gly Ala Ser Met Ala Ala Leu Thr Ala Ala
        130                 135                 140 cag ctg tcc gcg aca tac gac aac gtc cgt ctg tac aca ttc ggc gaa           480
Gln Leu Ser Ala Thr Tyr Asp Asn Val Arg Leu Tyr Thr Phe Gly Glu
145                 150                 155                 160 ccg cgc agc ggc aac cag gcc ttc gcg tcg tac atg aac gat gcg ttc           528
Pro Arg Ser Gly Asn Gln Ala Phe Ala Ser Tyr Met Asn Asp Ala Phe
                165                 170                 175 cag gtc tcg agc ccg gag acg acc cag tac ttc cgg gtc act cat tcc           576
Gln Val Ser Ser Pro Glu Thr Thr Gln Tyr Phe Arg Val Thr His Ser
                180                 185                 190 aac gac ggc atc cca aac ttg ccc ccg gcg gac gag ggt tac gcc cat           624
Asn Asp Gly Ile Pro Asn Leu Pro Pro Ala Asp Glu Gly Tyr Ala His
                195                 200                 205 ggt ggt gta gag tac tgg agc gtt gat cct tac agc gcc cag aac acg           672
Gly Gly Val Glu Tyr Trp Ser Val Asp Pro Tyr Ser Ala Gln Asn Thr
        210                 215                 220 ttt gtc tgt act ggg gat gaa gta cag tgc tgt gag gca cag ggc gga           720
Phe Val Cys Thr Gly Asp Glu Val Gln Cys Cys Glu Ala Gln Gly Gly
225                 230                 235                 240 cag ggg gtg aat gat gcg cat act act tat ttt ggg atg acg agc gga           768
Gln Gly Val Asn Asp Ala His Thr Thr Tyr Phe Gly Met Thr Ser Gly
                245                 250                 255 gct tgt act tgg ggc tcg act tac tcc agt gga tct tct tcg ggg tcg           816
Ala Cys Thr Trp Gly Ser Thr Tyr Ser Ser Gly Ser Ser Ser Gly Ser
                260                 265                 270 ggg tct agc tcc agc tcg agt tcg act acc act aag gcc act tcg acg           864
Gly Ser Ser Ser Ser Ser Ser Thr Thr Thr Lys Ala Thr Ser Thr
        275                 280                 285 acc ttg aag act acc tcg acc acc agc agt gga agc agt tcg aca tcg           912
Thr Leu Lys Thr Thr Ser Thr Thr Ser Ser Gly Ser Ser Ser Thr Ser
        290                 295                 300 gcg gcg tcg acc ccg agc tcg acc ggc gag aac aac ggc ttc tac tac           960
Ala Ala Ser Thr Pro Ser Ser Thr Gly Glu Asn Asn Gly Phe Tyr Tyr
305                 310                 315                 320 tcc ttc tgg acc gac ggc ggt gga gac gtg acc tac acc aac gga gat          1008
Ser Phe Trp Thr Asp Gly Gly Gly Asp Val Thr Tyr Thr Asn Gly Asp
                325                 330                 335 gct ggt gcc tac act gtt gag tgg tcc aac gtg ggc aac ttt gtc ggt          1056
Ala Gly Ala Tyr Thr Val Glu Trp Ser Asn Val Gly Asn Phe Val Gly
                340                 345                 350 gga aag ggc tgg aac ccc gga agt gcg cag gac atc acc tac agc ggc          1104
Gly Lys Gly Trp Asn Pro Gly Ser Ala Gln Asp Ile Thr Tyr Ser Gly
        355                 360                 365 acc ttc acc cct agc ggc aac ggc tac ctc tcc gtc tat ggc tgg acc          1152
Thr Phe Thr Pro Ser Gly Asn Gly Tyr Leu Ser Val Tyr Gly Trp Thr
        370                 375                 380 act gac cct ctg atc gag tac tac atc gtc gag tct tac ggc gac tac          1200
Thr Asp Pro Leu Ile Glu Tyr Tyr Ile Val Glu Ser Tyr Gly Asp Tyr
```

```
                385                 390                 395                 400
aac ccc ggc agt gga ggc acg tac aag ggc acc gtc acc tcg gac gga      1248
Asn Pro Gly Ser Gly Gly Thr Tyr Lys Gly Thr Val Thr Ser Asp Gly
            405                 410                 415 tcc gtt tac gat atc tac acg gct acc cgt acc aat gct gct tcc att      1296
Ser Val Tyr Asp Ile Tyr Thr Ala Thr Arg Thr Asn Ala Ala Ser Ile
        420                 425                 430 cag gga acc gct acc ttc act cag tac tgg tcc gtt cgc cag aac aag      1344
Gln Gly Thr Ala Thr Phe Thr Gln Tyr Trp Ser Val Arg Gln Asn Lys
    435                 440                 445 aga gtt ggc gga acc gtt acc acc tcc aac cac ttc aat gct tgg gct      1392
Arg Val Gly Gly Thr Val Thr Thr Ser Asn His Phe Asn Ala Trp Ala
450                 455                 460 aag ctg gga atg aac ctg ggt act cac aac tac cag atc gtg gct acc      1440
Lys Leu Gly Met Asn Leu Gly Thr His Asn Tyr Gln Ile Val Ala Thr
465                 470                 475                 480 gag ggt tac cag agc agt gga tct tcg tcc atc act gtt cag              1482
Glu Gly Tyr Gln Ser Ser Gly Ser Ser Ser Ile Thr Val Gln
                485                 490

<210> SEQ ID NO 12
<211> LENGTH: 494
<212> TYPE: PRT
<213> ORGANISM: Aspergillus niger

<400> SEQUENCE: 12

Ala Ser Thr Gln Gly Ile Ser Glu Asp Leu Tyr Asn Arg Leu Val Glu
1               5                   10                  15

Met Ala Thr Ile Ser Gln Ala Ala Tyr Ala Asp Leu Cys Asn Ile Pro
            20                  25                  30

Ser Thr Ile Ile Lys Gly Glu Lys Ile Tyr Asn Ala Gln Thr Asp Ile
        35                  40                  45

Asn Gly Trp Ile Leu Arg Asp Asp Thr Ser Lys Glu Ile Ile Thr Val
    50                  55                  60

Phe Arg Gly Thr Gly Ser Asp Thr Asn Leu Gln Leu Asp Thr Asn Tyr
65                  70                  75                  80

Thr Leu Thr Pro Phe Asp Thr Leu Pro Gln Cys Asn Asp Cys Glu Val
                85                  90                  95

His Gly Gly Tyr Tyr Ile Gly Trp Ile Ser Val Gln Asp Gln Val Glu
            100                 105                 110

Ser Leu Val Lys Gln Gln Ala Ser Gln Tyr Pro Asp Tyr Ala Leu Thr
        115                 120                 125

Val Thr Gly His Ser Leu Gly Ala Ser Met Ala Ala Leu Thr Ala Ala
    130                 135                 140

Gln Leu Ser Ala Thr Tyr Asp Asn Val Arg Leu Tyr Thr Phe Gly Glu
145                 150                 155                 160

Pro Arg Ser Gly Asn Gln Ala Phe Ala Ser Tyr Met Asn Asp Ala Phe
                165                 170                 175

Gln Val Ser Ser Pro Glu Thr Thr Gln Tyr Phe Arg Val Thr His Ser
            180                 185                 190

Asn Asp Gly Ile Pro Asn Leu Pro Pro Ala Asp Glu Gly Tyr Ala His
        195                 200                 205

Gly Gly Val Glu Tyr Trp Ser Val Asp Pro Tyr Ser Ala Gln Asn Thr
    210                 215                 220

Phe Val Cys Thr Gly Asp Glu Val Gln Cys Cys Glu Ala Gln Gly Gly
225                 230                 235                 240

Gln Gly Val Asn Asp Ala His Thr Thr Tyr Phe Gly Met Thr Ser Gly
```

```
                   245                 250                 255
Ala Cys Thr Trp Gly Ser Thr Tyr Ser Ser Gly Ser Ser Ser Gly Ser
            260                 265                 270

Gly Ser Ser Ser Ser Ser Ser Thr Thr Lys Ala Thr Ser Thr
        275                 280                 285

Thr Leu Lys Thr Thr Ser Thr Thr Ser Ser Gly Ser Ser Ser Thr Ser
        290                 295                 300

Ala Ala Ser Thr Pro Ser Ser Thr Gly Glu Asn Asn Gly Phe Tyr Tyr
305                 310                 315                 320

Ser Phe Trp Thr Asp Gly Gly Asp Val Thr Tyr Thr Asn Gly Asp
                325                 330                 335

Ala Gly Ala Tyr Thr Val Glu Trp Ser Asn Val Gly Asn Phe Val Gly
                340                 345                 350

Gly Lys Gly Trp Asn Pro Gly Ala Gln Asp Ile Thr Tyr Ser Gly
            355                 360                 365

Thr Phe Thr Pro Ser Gly Asn Gly Tyr Leu Ser Val Tyr Gly Trp Thr
        370                 375                 380

Thr Asp Pro Leu Ile Glu Tyr Tyr Ile Val Glu Ser Tyr Gly Asp Tyr
385                 390                 395                 400

Asn Pro Gly Ser Gly Gly Thr Tyr Lys Gly Thr Val Thr Ser Asp Gly
                405                 410                 415

Ser Val Tyr Asp Ile Tyr Thr Ala Thr Arg Thr Asn Ala Ala Ser Ile
            420                 425                 430

Gln Gly Thr Ala Thr Phe Thr Gln Tyr Trp Ser Val Arg Gln Asn Lys
        435                 440                 445

Arg Val Gly Gly Thr Val Thr Thr Ser Asn His Phe Asn Ala Trp Ala
    450                 455                 460

Lys Leu Gly Met Asn Leu Gly Thr His Asn Tyr Gln Ile Val Ala Thr
465                 470                 475                 480

Glu Gly Tyr Gln Ser Ser Gly Ser Ser Ile Thr Val Gln
                485                 490

<210> SEQ ID NO 13
<211> LENGTH: 1722
<212> TYPE: DNA
<213> ORGANISM: Aspergillus niger
<220> FEATURE:
<221> NAME/KEY: CDS
<222> LOCATION: (1)..(1722)
<223> OTHER INFORMATION:

<400> SEQUENCE: 13 gcc tcc acg caa ggc atc tcc gaa gac ctc tac aat cgc ttg gta gag      48
Ala Ser Thr Gln Gly Ile Ser Glu Asp Leu Tyr Asn Arg Leu Val Glu
1               5                   10                  15 atg gcc act atc tcc caa gcc gcc tac gcc gac cta tgc aat att cca      96
Met Ala Thr Ile Ser Gln Ala Ala Tyr Ala Asp Leu Cys Asn Ile Pro
            20                  25                  30 tcg act att atc aaa gga gag aaa att tac aac gct caa act gat atc     144
Ser Thr Ile Ile Lys Gly Glu Lys Ile Tyr Asn Ala Gln Thr Asp Ile
        35                  40                  45 aac gga tgg atc ctc cgc gac gac acc agc aaa gaa att atc acc gtc     192
Asn Gly Trp Ile Leu Arg Asp Asp Thr Ser Lys Glu Ile Ile Thr Val
    50                  55                  60 ttc cgt ggc act ggc agt gac aca aac cta cag ctc gat act aac tac     240
Phe Arg Gly Thr Gly Ser Asp Thr Asn Leu Gln Leu Asp Thr Asn Tyr
65                  70                  75                  80 acg ctc acg cca ttc gac act cta cct caa tgc aac gat tgc gag gta     288
```

|              |     |     |     |     |     |     |     |     |     |     |     |     |     |     |     |      |
|---|---|---|---|---|---|---|---|---|---|---|---|---|---|---|---|---|
| Thr | Leu | Thr | Pro | Phe | Asp | Thr | Leu | Pro | Gln | Cys | Asn | Asp | Cys | Glu | Val |      |
|     |     |     |     | 85  |     |     |     | 90  |     |     |     |     | 95  |     |     |      |

```
cac ggt gga tac tat att gga tgg atc tca gtc caa gac caa gtc gag    336
His Gly Gly Tyr Tyr Ile Gly Trp Ile Ser Val Gln Asp Gln Val Glu
            100             105             110 tcg ctt gtc aaa caa cag gct agc cag tat ccg gac tat gcg ctt acc    384
Ser Leu Val Lys Gln Gln Ala Ser Gln Tyr Pro Asp Tyr Ala Leu Thr
            115             120             125 gtg aca ggc cat agt ctg gga gcg tcg atg gca gca ctc act gcc gcc    432
Val Thr Gly His Ser Leu Gly Ala Ser Met Ala Ala Leu Thr Ala Ala
        130             135             140 cag ctg tcc gcg aca tac gac aac gtc cgt ctg tac aca ttc ggc gaa    480
Gln Leu Ser Ala Thr Tyr Asp Asn Val Arg Leu Tyr Thr Phe Gly Glu
145             150             155             160 ccg cgc agc ggc aac cag gcc ttc gcg tcg tac atg aac gat gcg ttc    528
Pro Arg Ser Gly Asn Gln Ala Phe Ala Ser Tyr Met Asn Asp Ala Phe
                165             170             175 cag gtc tcg agc ccg gag acg acc cag tac ttc cgg gtc act cat tcc    576
Gln Val Ser Ser Pro Glu Thr Thr Gln Tyr Phe Arg Val Thr His Ser
            180             185             190 aac gac ggc atc cca aac ttg ccc ccg gcg gac gag ggt tac gcc cat    624
Asn Asp Gly Ile Pro Asn Leu Pro Pro Ala Asp Glu Gly Tyr Ala His
            195             200             205 ggt ggt gta gag tac tgg agc gtt gat cct tac agc gcc cag aac acg    672
Gly Gly Val Glu Tyr Trp Ser Val Asp Pro Tyr Ser Ala Gln Asn Thr
        210             215             220 ttt gtc tgt act ggg gat gaa gta cag tgc tgt gag gca cag ggc gga    720
Phe Val Cys Thr Gly Asp Glu Val Gln Cys Cys Glu Ala Gln Gly Gly
225             230             235             240 cag ggg gtg aat gat gcg cat act act tat ttt ggg atg acg agc gga    768
Gln Gly Val Asn Asp Ala His Thr Thr Tyr Phe Gly Met Thr Ser Gly
                245             250             255 gct tgt act tgg ggc tcg act tac tcc agt gga tct tct tcg ggg tcg    816
Ala Cys Thr Trp Gly Ser Thr Tyr Ser Ser Gly Ser Ser Ser Gly Ser
            260             265             270 ggg tct agc tcc agc tcg agt tcg act acc act aag gcc act tcg acg    864
Gly Ser Ser Ser Ser Ser Ser Thr Thr Thr Lys Ala Thr Ser Thr
        275             280             285 acc ttg aag act acc tcg acc acc agc agt gga agc agt tcg aca tcg    912
Thr Leu Lys Thr Thr Ser Thr Thr Ser Ser Gly Ser Ser Ser Thr Ser
290             295             300 gcg gcg tcg acc ccg agc tcg acc ggc gag aac aac ggc ttc tac tac    960
Ala Ala Ser Thr Pro Ser Ser Thr Gly Glu Asn Asn Gly Phe Tyr Tyr
305             310             315             320 tcc ttc tgg acc gac ggc ggt gga gac gtg acc tac acc aac gga gat    1008
Ser Phe Trp Thr Asp Gly Gly Gly Asp Val Thr Tyr Thr Asn Gly Asp
                325             330             335 gct ggt gcc tac act gtt gag tgg tcc aac gtg ggc aac ttt gtc ggt    1056
Ala Gly Ala Tyr Thr Val Glu Trp Ser Asn Val Gly Asn Phe Val Gly
            340             345             350 gga aag ggc tgg aac ccc gga agt gcg cag gac atc acc tac agc ggc    1104
Gly Lys Gly Trp Asn Pro Gly Ser Ala Gln Asp Ile Thr Tyr Ser Gly
        355             360             365 acc ttc acc cct agc ggc aac ggc tac ctc tcc gtc tat ggc tgg acc    1152
Thr Phe Thr Pro Ser Gly Asn Gly Tyr Leu Ser Val Tyr Gly Trp Thr
        370             375             380 act gac cct ctg atc gag tac tac atc gtc gag tct tac ggc gac tac    1200
Thr Asp Pro Leu Ile Glu Tyr Tyr Ile Val Glu Ser Tyr Gly Asp Tyr
385             390             395             400 aac ccc ggc agt gga ggc acg tac aag ggc acc gtc acc tcg gac gga    1248
```

-continued

```
Asn Pro Gly Ser Gly Gly Thr Tyr Lys Gly Thr Val Thr Ser Asp Gly
            405                 410                 415 tcc gtt tac gat atc tac acg gct acc cgt acc aat gct gct tcc att    1296
Ser Val Tyr Asp Ile Tyr Thr Ala Thr Arg Thr Asn Ala Ala Ser Ile
        420                 425                 430 cag gga acc gct acc ttc act cag tac tgg tcc gtt cgc cag aac aag    1344
Gln Gly Thr Ala Thr Phe Thr Gln Tyr Trp Ser Val Arg Gln Asn Lys
435                 440                 445 aga gtt ggc gga acc gtt acc acc tcc aac cac ttc aat gct tgg gct    1392
Arg Val Gly Gly Thr Val Thr Thr Ser Asn His Phe Asn Ala Trp Ala
    450                 455                 460 aag ctg gga atg aac ctg ggt act cac aac tac cag atc gtg gct acc    1440
Lys Leu Gly Met Asn Leu Gly Thr His Asn Tyr Gln Ile Val Ala Thr
465                 470                 475                 480 gag ggt tac cag agc agt gga tct tcg tcc atc act gtt cag ggc tcg    1488
Glu Gly Tyr Gln Ser Ser Gly Ser Ser Ile Thr Val Gln Gly Ser
                485                 490                 495 act tac tcc agt gga tct tct tcg ggg tcg ggg tct agc tcc agc tcg    1536
Thr Tyr Ser Ser Gly Ser Ser Ser Gly Ser Gly Ser Ser Ser Ser Ser
            500                 505                 510 agt tcg act acc act aag gcc act tcg acg acc ttg aag act acc tcg    1584
Ser Ser Thr Thr Thr Lys Ala Thr Ser Thr Thr Leu Lys Thr Thr Ser
        515                 520                 525 acc acc agc agt gga agc agt tcg aca tcg gcg gcg cag gcg tat gga    1632
Thr Thr Ser Ser Gly Ser Ser Ser Thr Ser Ala Ala Gln Ala Tyr Gly
    530                 535                 540 cag tgt ggt gga cag ggc tgg act ggt ccg acc act tgt gtg agt ggg    1680
Gln Cys Gly Gly Gln Gly Trp Thr Gly Pro Thr Thr Cys Val Ser Gly
545                 550                 555                 560 tac act tgc acg tat gag aat gcg tac tac tcg cag tgt ttg            1722
Tyr Thr Cys Thr Tyr Glu Asn Ala Tyr Tyr Ser Gln Cys Leu
                565                 570

<210> SEQ ID NO 14
<211> LENGTH: 574
<212> TYPE: PRT
<213> ORGANISM: Aspergillus niger

<400> SEQUENCE: 14

Ala Ser Thr Gln Gly Ile Ser Glu Asp Leu Tyr Asn Arg Leu Val Glu
1               5                   10                  15

Met Ala Thr Ile Ser Gln Ala Ala Tyr Ala Asp Leu Cys Asn Ile Pro
            20                  25                  30

Ser Thr Ile Ile Lys Gly Glu Lys Ile Tyr Asn Ala Gln Thr Asp Ile
        35                  40                  45

Asn Gly Trp Ile Leu Arg Asp Asp Thr Ser Lys Glu Ile Ile Thr Val
    50                  55                  60

Phe Arg Gly Thr Gly Ser Asp Thr Asn Leu Gln Leu Asp Thr Asn Tyr
65                  70                  75                  80

Thr Leu Thr Pro Phe Asp Thr Leu Pro Gln Cys Asn Asp Cys Glu Val
                85                  90                  95

His Gly Gly Tyr Tyr Ile Gly Trp Ile Ser Val Gln Asp Gln Val Glu
            100                 105                 110

Ser Leu Val Lys Gln Gln Ala Ser Gln Tyr Pro Asp Tyr Ala Leu Thr
        115                 120                 125

Val Thr Gly His Ser Leu Gly Ala Ser Met Ala Ala Leu Thr Ala Ala
    130                 135                 140

Gln Leu Ser Ala Thr Tyr Asp Asn Val Arg Leu Tyr Thr Phe Gly Glu
145                 150                 155                 160
```

```
Pro Arg Ser Gly Asn Gln Ala Phe Ala Ser Tyr Met Asn Asp Ala Phe
            165                 170                 175

Gln Val Ser Ser Pro Glu Thr Thr Gln Tyr Phe Arg Val Thr His Ser
            180                 185                 190

Asn Asp Gly Ile Pro Asn Leu Pro Pro Ala Asp Glu Gly Tyr Ala His
            195                 200                 205

Gly Gly Val Glu Tyr Trp Ser Val Asp Pro Tyr Ser Ala Gln Asn Thr
        210                 215                 220

Phe Val Cys Thr Gly Asp Glu Val Gln Cys Glu Ala Gln Gly Gly
225                 230                 235                 240

Gln Gly Val Asn Asp Ala His Thr Thr Tyr Phe Gly Met Thr Ser Gly
            245                 250                 255

Ala Cys Thr Trp Gly Ser Thr Tyr Ser Ser Gly Ser Ser Ser Gly Ser
            260                 265                 270

Gly Ser Ser Ser Ser Ser Ser Thr Thr Lys Ala Thr Ser Thr
        275                 280                 285

Thr Leu Lys Thr Thr Ser Thr Thr Ser Ser Gly Ser Ser Ser Thr Ser
        290                 295                 300

Ala Ala Ser Thr Pro Ser Ser Thr Gly Glu Asn Asn Gly Phe Tyr Tyr
305                 310                 315                 320

Ser Phe Trp Thr Asp Gly Gly Asp Val Thr Tyr Thr Asn Gly Asp
            325                 330                 335

Ala Gly Ala Tyr Thr Val Glu Trp Ser Asn Val Gly Asn Phe Val Gly
            340                 345                 350

Gly Lys Gly Trp Asn Pro Gly Ser Ala Gln Asp Ile Thr Tyr Ser Gly
            355                 360                 365

Thr Phe Thr Pro Ser Gly Asn Gly Tyr Leu Ser Val Tyr Gly Trp Thr
        370                 375                 380

Thr Asp Pro Leu Ile Glu Tyr Tyr Ile Val Glu Ser Tyr Gly Asp Tyr
385                 390                 395                 400

Asn Pro Gly Ser Gly Gly Thr Tyr Lys Gly Thr Val Thr Ser Asp Gly
            405                 410                 415

Ser Val Tyr Asp Ile Tyr Thr Ala Thr Arg Thr Asn Ala Ala Ser Ile
            420                 425                 430

Gln Gly Thr Ala Thr Phe Thr Gln Tyr Trp Ser Val Arg Gln Asn Lys
            435                 440                 445

Arg Val Gly Gly Thr Val Thr Thr Ser Asn His Phe Asn Ala Trp Ala
450                 455                 460

Lys Leu Gly Met Asn Leu Gly Thr His Asn Tyr Gln Ile Val Ala Thr
465                 470                 475                 480

Glu Gly Tyr Gln Ser Ser Gly Ser Ser Ser Ile Thr Val Gln Gly Ser
            485                 490                 495

Thr Tyr Ser Ser Gly Ser Ser Ser Gly Ser Gly Ser Ser Ser Ser
            500                 505                 510

Ser Ser Thr Thr Thr Lys Ala Thr Ser Thr Thr Leu Lys Thr Thr Ser
        515                 520                 525

Thr Thr Ser Ser Gly Ser Ser Ser Thr Ser Ala Ala Gln Ala Tyr Gly
        530                 535                 540

Gln Cys Gly Gly Gln Gly Trp Thr Gly Pro Thr Thr Cys Val Ser Gly
545                 550                 555                 560

Tyr Thr Cys Thr Tyr Glu Asn Ala Tyr Tyr Ser Gln Cys Leu
            565                 570
```

<210> SEQ ID NO 15
<211> LENGTH: 2214
<212> TYPE: DNA
<213> ORGANISM: Aspergillus niger
<220> FEATURE:
<221> NAME/KEY: CDS
<222> LOCATION: (1)..(2214)
<223> OTHER INFORMATION:

<400> SEQUENCE: 15

```
gcg acc gac ccc ttc cag tcg cgg tgc aat gaa ttc cag aac aag atc      48
Ala Thr Asp Pro Phe Gln Ser Arg Cys Asn Glu Phe Gln Asn Lys Ile
  1               5                  10                  15 gac atc gcc aat gtc acc gtc aga tcg gtc gca tac gtt gct gct gga      96
Asp Ile Ala Asn Val Thr Val Arg Ser Val Ala Tyr Val Ala Ala Gly
             20                  25                  30 cag aac atc tcc caa gcg gag gtc gcc tcc gtg tgt aaa gca tcg gtt     144
Gln Asn Ile Ser Gln Ala Glu Val Ala Ser Val Cys Lys Ala Ser Val
         35                  40                  45 caa gcc agt gtc gac ctg tgc cgg gta acc atg aac atc tcg acg tcg     192
Gln Ala Ser Val Asp Leu Cys Arg Val Thr Met Asn Ile Ser Thr Ser
     50                  55                  60 gat cgc agc cat ctg tgg gct gag gcc tgg ctc cca aga aat tat acc     240
Asp Arg Ser His Leu Trp Ala Glu Ala Trp Leu Pro Arg Asn Tyr Thr
 65                  70                  75                  80 ggt cgc ttc gtg agc acg ggg aat gga ggt cta gcc ggc tgt gtc caa     288
Gly Arg Phe Val Ser Thr Gly Asn Gly Gly Leu Ala Gly Cys Val Gln
                 85                  90                  95 gaa acg gac ctc aac ttt gca gcc aac ttt ggt ttc gct acc gtg ggc     336
Glu Thr Asp Leu Asn Phe Ala Ala Asn Phe Gly Phe Ala Thr Val Gly
            100                 105                 110 acc aac ggt gga cat gac ggg gac acg gcc aaa tac ttc ctc aac aac     384
Thr Asn Gly Gly His Asp Gly Asp Thr Ala Lys Tyr Phe Leu Asn Asn
        115                 120                 125 tcg gag gtt ctg gcc gat ttt gcc tat cgc tca gtg cac gaa ggg acc     432
Ser Glu Val Leu Ala Asp Phe Ala Tyr Arg Ser Val His Glu Gly Thr
    130                 135                 140 gtg gtg ggt aag caa cta act caa ttg ttt tat gac gag gga tac aac     480
Val Val Gly Lys Gln Leu Thr Gln Leu Phe Tyr Asp Glu Gly Tyr Asn
145                 150                 155                 160 tac tcc tac tat ttg ggt tgc tcc acc gga ggc cgc caa ggc tac cag     528
Tyr Ser Tyr Tyr Leu Gly Cys Ser Thr Gly Gly Arg Gln Gly Tyr Gln
                165                 170                 175 caa gtc caa cgg ttt ccc gac gac tat gac gga gtg att gcg ggc tcc     576
Gln Val Gln Arg Phe Pro Asp Asp Tyr Asp Gly Val Ile Ala Gly Ser
            180                 185                 190 gca gcg atg aac ttt atc aac ctg atc tcc tgg ggg gcc ttc ttg tgg     624
Ala Ala Met Asn Phe Ile Asn Leu Ile Ser Trp Gly Ala Phe Leu Trp
        195                 200                 205 aag gcg acg ggg tta gcg gat gat cca gac ttt atc tct gca aac ctg     672
Lys Ala Thr Gly Leu Ala Asp Asp Pro Asp Phe Ile Ser Ala Asn Leu
    210                 215                 220 tgg tcc gta atc cac cag gag att gtt cgt cag tgc gac ctg gtc gat     720
Trp Ser Val Ile His Gln Glu Ile Val Arg Gln Cys Asp Leu Val Asp
225                 230                 235                 240 ggg gct ctg gat gga atc atc gaa gac cct gat ttc tgt gct cca gtc     768
Gly Ala Leu Asp Gly Ile Ile Glu Asp Pro Asp Phe Cys Ala Pro Val
                245                 250                 255 atc gag cgc ttg atc tgc gac ggg act acc aac ggc acc tct tgt atc     816
Ile Glu Arg Leu Ile Cys Asp Gly Thr Thr Asn Gly Thr Ser Cys Ile
            260                 265                 270 acg gga gcc cag gca gca aag gtc aac cgg gcc ttg agt gac ttc tat     864
```

```
      Thr Gly Ala Gln Ala Ala Lys Val Asn Arg Ala Leu Ser Asp Phe Tyr
              275                 280                 285 ggc ccc gac ggg aca gtg tac tac ccg cgc ctg aac tat ggg ggt gag        912
Gly Pro Asp Gly Thr Val Tyr Tyr Pro Arg Leu Asn Tyr Gly Gly Glu
        290                 295                 300 gcc gac tcg gct tcc ctg tac ttc acg ggg tcg atg tac agc cgt acg        960
Ala Asp Ser Ala Ser Leu Tyr Phe Thr Gly Ser Met Tyr Ser Arg Thr
305                 310                 315                 320 gag gaa tgg tac aaa tat gtg gtc tat aac gac acc aac tgg aac tcc       1008
Glu Glu Trp Tyr Lys Tyr Val Val Tyr Asn Asp Thr Asn Trp Asn Ser
                325                 330                 335 agc cag tgg acg ctg gag agt gcc aag ctg gcc ctg gag cag aat ccg       1056
Ser Gln Trp Thr Leu Glu Ser Ala Lys Leu Ala Leu Glu Gln Asn Pro
            340                 345                 350 ttc aat atc cag gcg ttt gat ccc aac atc acg gcc ttc cgg gac cgg       1104
Phe Asn Ile Gln Ala Phe Asp Pro Asn Ile Thr Ala Phe Arg Asp Arg
        355                 360                 365 ggt ggc aag ctg ctg tcc tac cac ggc acg cag gat ccc att atc agc       1152
Gly Gly Lys Leu Leu Ser Tyr His Gly Thr Gln Asp Pro Ile Ile Ser
    370                 375                 380 tcc acg gat agc aag ctc tac tac cga cgg gta gcg aat gcc ctg aat       1200
Ser Thr Asp Ser Lys Leu Tyr Tyr Arg Arg Val Ala Asn Ala Leu Asn
385                 390                 395                 400 gcc gcg ccg tcc gag cta gat gag ttc tat cgg ttc ttc cag atc tcc       1248
Ala Ala Pro Ser Glu Leu Asp Glu Phe Tyr Arg Phe Phe Gln Ile Ser
                405                 410                 415 ggc atg ggc cac tgt ggc gat ggc acg gga gca tcg tac atc ggc cag       1296
Gly Met Gly His Cys Gly Asp Gly Thr Gly Ala Ser Tyr Ile Gly Gln
            420                 425                 430 gga tat ggc acg tac acc tcc aag gcg ccc caa gtc aac ctg ctg cgc       1344
Gly Tyr Gly Thr Tyr Thr Ser Lys Ala Pro Gln Val Asn Leu Leu Arg
        435                 440                 445 acg atg gtg gac tgg gtg gaa aac gga aag gcg ccc gag tat atg ccg       1392
Thr Met Val Asp Trp Val Glu Asn Gly Lys Ala Pro Glu Tyr Met Pro
    450                 455                 460 ggc aac aag ctc aac gcg aac ggg tca att gag tac atg cgc aag cac       1440
Gly Asn Lys Leu Asn Ala Asn Gly Ser Ile Glu Tyr Met Arg Lys His
465                 470                 475                 480 tgc cgg tat ccg aag cat aac att cac acg ggg ccg ggt aac tac acc       1488
Cys Arg Tyr Pro Lys His Asn Ile His Thr Gly Pro Gly Asn Tyr Thr
                485                 490                 495 gat cct aac tcc tgg act tgc gta ggc tcg act tac tcc agt gga tct       1536
Asp Pro Asn Ser Trp Thr Cys Val Gly Ser Thr Tyr Ser Ser Gly Ser
            500                 505                 510 tct tcg ggg tcg ggg tct agc tcc agc tcg agt tcg act acc act aag       1584
Ser Ser Gly Ser Gly Ser Ser Ser Ser Ser Ser Thr Thr Thr Lys
        515                 520                 525 gcc act tcg acg acc ttg aag act acc tcg acc acc agc agt gga agc       1632
Ala Thr Ser Thr Thr Leu Lys Thr Thr Ser Thr Thr Ser Ser Gly Ser
    530                 535                 540 agt tcg aca tcg gcg gcg tcg acc ccg agc tcg acc ggc gag aac aac       1680
Ser Ser Thr Ser Ala Ala Ser Thr Pro Ser Ser Thr Gly Glu Asn Asn
545                 550                 555                 560 ggc ttc tac tac tcc ttc tgg acc gac ggc ggt gga gac gtg acc tac       1728
Gly Phe Tyr Tyr Ser Phe Trp Thr Asp Gly Gly Gly Asp Val Thr Tyr
                565                 570                 575 acc aac gga gat gct ggt gcc tac act gtt gag tgg tcc aac gtg ggc       1776
Thr Asn Gly Asp Ala Gly Ala Tyr Thr Val Glu Trp Ser Asn Val Gly
            580                 585                 590 aac ttt gtc ggt gga aag ggc tgg aac ccc gga agt gcg cag gac atc       1824
```

```
                                                   -continued

Asn Phe Val Gly Gly Lys Gly Trp Asn Pro Gly Ser Ala Gln Asp Ile
        595                 600                 605 acc tac agc ggc acc ttc acc cct agc ggc aac ggc tac ctc tcc gtc      1872
Thr Tyr Ser Gly Thr Phe Thr Pro Ser Gly Asn Gly Tyr Leu Ser Val
    610                 615                 620 tat ggc tgg acc act gac cct ctg atc gag tac tac atc gtc gag tct      1920
Tyr Gly Trp Thr Thr Asp Pro Leu Ile Glu Tyr Tyr Ile Val Glu Ser
625                 630                 635                 640 tac ggc gac tac aac ccc ggc agt gga ggc acg tac aag ggc acc gtc      1968
Tyr Gly Asp Tyr Asn Pro Gly Ser Gly Gly Thr Tyr Lys Gly Thr Val
                645                 650                 655 acc tcg gac gga tcc gtt tac gat atc tac acg gct acc cgt acc aat      2016
Thr Ser Asp Gly Ser Val Tyr Asp Ile Tyr Thr Ala Thr Arg Thr Asn
        660                 665                 670 gct gct tcc att cag gga acc gct acc ttc act cag tac tgg tcc gtt      2064
Ala Ala Ser Ile Gln Gly Thr Ala Thr Phe Thr Gln Tyr Trp Ser Val
    675                 680                 685 cgc cag aac aag aga gtt ggc gga acc gtt acc acc tcc aac cac ttc      2112
Arg Gln Asn Lys Arg Val Gly Gly Thr Val Thr Thr Ser Asn His Phe
690                 695                 700 aat gct tgg gct aag ctg gga atg aac ctg ggt act cac aac tac cag      2160
Asn Ala Trp Ala Lys Leu Gly Met Asn Leu Gly Thr His Asn Tyr Gln
705                 710                 715                 720 atc gtg gct acc gag ggt tac cag agc agt gga tct tcg tcc atc act      2208
Ile Val Ala Thr Glu Gly Tyr Gln Ser Ser Gly Ser Ser Ser Ile Thr
                725                 730                 735 gtt cag                                                              2214
Val Gln <210> SEQ ID NO 16
<211> LENGTH: 738
<212> TYPE: PRT
<213> ORGANISM: Aspergillus niger

<400> SEQUENCE: 16

Ala Thr Asp Pro Phe Gln Ser Arg Cys Asn Glu Phe Gln Asn Lys Ile
1               5                   10                  15

Asp Ile Ala Asn Val Thr Val Arg Ser Val Ala Tyr Val Ala Ala Gly
            20                  25                  30

Gln Asn Ile Ser Gln Ala Glu Val Ala Ser Val Cys Lys Ala Ser Val
        35                  40                  45

Gln Ala Ser Val Asp Leu Cys Arg Val Thr Met Asn Ile Ser Thr Ser
    50                  55                  60

Asp Arg Ser His Leu Trp Ala Glu Ala Trp Leu Pro Arg Asn Tyr Thr
65                  70                  75                  80

Gly Arg Phe Val Ser Thr Gly Asn Gly Gly Leu Ala Gly Cys Val Gln
                85                  90                  95

Glu Thr Asp Leu Asn Phe Ala Ala Asn Phe Gly Phe Ala Thr Val Gly
            100                 105                 110

Thr Asn Gly Gly His Asp Gly Asp Thr Ala Lys Tyr Phe Leu Asn Asn
        115                 120                 125

Ser Glu Val Leu Ala Asp Phe Ala Tyr Arg Ser Val His Glu Gly Thr
    130                 135                 140

Val Val Gly Lys Gln Leu Thr Gln Leu Phe Tyr Asp Glu Gly Tyr Asn
145                 150                 155                 160

Tyr Ser Tyr Tyr Leu Gly Cys Ser Thr Gly Arg Gln Gly Tyr Gln
                165                 170                 175

Gln Val Gln Arg Phe Pro Asp Asp Tyr Asp Gly Val Ile Ala Gly Ser
```

-continued

```
                180             185             190
Ala Ala Met Asn Phe Ile Asn Leu Ile Ser Trp Gly Ala Phe Leu Trp
            195                 200                 205
Lys Ala Thr Gly Leu Ala Asp Asp Pro Asp Phe Ile Ser Ala Asn Leu
            210                 215                 220
Trp Ser Val Ile His Gln Glu Ile Val Arg Gln Cys Asp Leu Val Asp
225                 230                 235                 240
Gly Ala Leu Asp Gly Ile Ile Glu Asp Pro Asp Phe Cys Ala Pro Val
                245                 250                 255
Ile Glu Arg Leu Ile Cys Asp Gly Thr Thr Asn Gly Thr Ser Cys Ile
                260                 265                 270
Thr Gly Ala Gln Ala Ala Lys Val Asn Arg Ala Leu Ser Asp Phe Tyr
            275                 280                 285
Gly Pro Asp Gly Thr Val Tyr Tyr Pro Arg Leu Asn Tyr Gly Gly Glu
            290                 295                 300
Ala Asp Ser Ala Ser Leu Tyr Phe Thr Gly Ser Met Tyr Ser Arg Thr
305                 310                 315                 320
Glu Glu Trp Tyr Lys Tyr Val Val Tyr Asn Asp Thr Asn Trp Asn Ser
                325                 330                 335
Ser Gln Trp Thr Leu Glu Ser Ala Lys Leu Ala Leu Glu Gln Asn Pro
            340                 345                 350
Phe Asn Ile Gln Ala Phe Asp Pro Asn Ile Thr Ala Phe Arg Asp Arg
            355                 360                 365
Gly Gly Lys Leu Leu Ser Tyr His Gly Thr Gln Asp Pro Ile Ile Ser
            370                 375                 380
Ser Thr Asp Ser Lys Leu Tyr Tyr Arg Arg Val Ala Asn Ala Leu Asn
385                 390                 395                 400
Ala Ala Pro Ser Glu Leu Asp Glu Phe Tyr Arg Phe Phe Gln Ile Ser
                405                 410                 415
Gly Met Gly His Cys Gly Asp Gly Thr Gly Ala Ser Tyr Ile Gly Gln
                420                 425                 430
Gly Tyr Gly Thr Tyr Thr Ser Lys Ala Pro Gln Val Asn Leu Leu Arg
            435                 440                 445
Thr Met Val Asp Trp Val Glu Asn Gly Lys Ala Pro Glu Tyr Met Pro
450                 455                 460
Gly Asn Lys Leu Asn Ala Asn Gly Ser Ile Glu Tyr Met Arg Lys His
465                 470                 475                 480
Cys Arg Tyr Pro Lys His Asn Ile His Thr Gly Pro Gly Asn Tyr Thr
                485                 490                 495
Asp Pro Asn Ser Trp Thr Cys Val Gly Ser Thr Tyr Ser Ser Gly Ser
                500                 505                 510
Ser Ser Gly Ser Gly Ser Ser Ser Ser Ser Thr Thr Thr Lys
            515                 520                 525
Ala Thr Ser Thr Thr Leu Lys Thr Thr Ser Thr Thr Ser Ser Gly Ser
            530                 535                 540
Ser Ser Thr Ser Ala Ala Ser Thr Pro Ser Ser Thr Gly Glu Asn Asn
545                 550                 555                 560
Gly Phe Tyr Tyr Ser Phe Trp Thr Asp Gly Gly Asp Val Thr Tyr
                565                 570                 575
Thr Asn Gly Asp Ala Gly Ala Tyr Thr Val Glu Trp Ser Asn Val Gly
            580                 585                 590
Asn Phe Val Gly Gly Lys Gly Trp Asn Pro Gly Ser Ala Gln Asp Ile
            595                 600                 605
```

-continued

```
Thr Tyr Ser Gly Thr Phe Thr Pro Ser Gly Asn Gly Tyr Leu Ser Val
    610                 615                 620
Tyr Gly Trp Thr Thr Asp Pro Leu Ile Glu Tyr Ile Val Glu Ser
625                 630                 635                 640
Tyr Gly Asp Tyr Asn Pro Gly Ser Gly Gly Thr Tyr Lys Gly Thr Val
                    645                 650                 655
Thr Ser Asp Gly Ser Val Tyr Asp Ile Tyr Thr Ala Thr Arg Thr Asn
                660                 665                 670
Ala Ala Ser Ile Gln Gly Thr Ala Thr Phe Thr Gln Tyr Trp Ser Val
            675                 680                 685
Arg Gln Asn Lys Arg Val Gly Gly Thr Val Thr Ser Asn His Phe
690                 695                 700
Asn Ala Trp Ala Lys Leu Gly Met Asn Leu Gly Thr His Asn Tyr Gln
705                 710                 715                 720
Ile Val Ala Thr Glu Gly Tyr Gln Ser Ser Gly Ser Ser Ile Thr
                    725                 730                 735
Val Gln

<210> SEQ ID NO 17
<211> LENGTH: 2454
<212> TYPE: DNA
<213> ORGANISM: Aspergillus niger
<220> FEATURE:
<221> NAME/KEY: CDS
<222> LOCATION: (1)..(2454)
<223> OTHER INFORMATION:

<400> SEQUENCE: 17 gcg acc gac ccc ttc cag tcg cgg tgc aat gaa ttc cag aac aag atc      48
Ala Thr Asp Pro Phe Gln Ser Arg Cys Asn Glu Phe Gln Asn Lys Ile
1               5                   10                  15 gac atc gcc aat gtc acc gtc aga tcg gtc gca tac gtt gct gct gga      96
Asp Ile Ala Asn Val Thr Val Arg Ser Val Ala Tyr Val Ala Ala Gly
            20                  25                  30 cag aac atc tcc caa gcg gag gtc gcc tcc gtg tgt aaa gca tcg gtt     144
Gln Asn Ile Ser Gln Ala Glu Val Ala Ser Val Cys Lys Ala Ser Val
        35                  40                  45 caa gcc agt gtc gac ctg tgc cgg gta acc atg aac atc tcg acg tcg     192
Gln Ala Ser Val Asp Leu Cys Arg Val Thr Met Asn Ile Ser Thr Ser
    50                  55                  60 gat cgc agc cat ctg tgg gct gag gcc tgg ctc cca aga aat tat acc     240
Asp Arg Ser His Leu Trp Ala Glu Ala Trp Leu Pro Arg Asn Tyr Thr
65                  70                  75                  80 ggt cgc ttc gtg agc acg ggg aat gga ggt cta gcc ggc tgt gtc caa     288
Gly Arg Phe Val Ser Thr Gly Asn Gly Gly Leu Ala Gly Cys Val Gln
                85                  90                  95 gaa acg gac ctc aac ttt gca gcc aac ttt ggt ttc gct acc gtg ggc     336
Glu Thr Asp Leu Asn Phe Ala Ala Asn Phe Gly Phe Ala Thr Val Gly
            100                 105                 110 acc aac ggt gga cat gac ggg gac acg gcc aaa tac ttc ctc aac aac     384
Thr Asn Gly Gly His Asp Gly Asp Thr Ala Lys Tyr Phe Leu Asn Asn
        115                 120                 125 tcg gag gtt ctg gcc gat ttt gcc tat cgc tca gtg cac gaa ggg acc     432
Ser Glu Val Leu Ala Asp Phe Ala Tyr Arg Ser Val His Glu Gly Thr
    130                 135                 140 gtg gtg ggt aag caa cta act caa ttg ttt tat gac gag gga tac aac     480
Val Val Gly Lys Gln Leu Thr Gln Leu Phe Tyr Asp Glu Gly Tyr Asn
145                 150                 155                 160 tac tcc tac tat ttg ggt tgc tcc acc gga ggc cgc caa ggc tac cag     528
Tyr Ser Tyr Tyr Leu Gly Cys Ser Thr Gly Gly Arg Gln Gly Tyr Gln
```

```
                    165                 170                 175
caa gtc caa cgg ttt ccc gac gac tat gac gga gtg att gcg ggc tcc      576
Gln Val Gln Arg Phe Pro Asp Asp Tyr Asp Gly Val Ile Ala Gly Ser
            180                 185                 190 gca gcg atg aac ttt atc aac ctg atc tcc tgg ggg gcc ttc ttg tgg      624
Ala Ala Met Asn Phe Ile Asn Leu Ile Ser Trp Gly Ala Phe Leu Trp
        195                 200                 205 aag gcg acg ggg tta gcg gat gat cca gac ttt atc tct gca aac ctg      672
Lys Ala Thr Gly Leu Ala Asp Asp Pro Asp Phe Ile Ser Ala Asn Leu
    210                 215                 220 tgg tcc gta atc cac cag gag att gtt cgt cag tgc gac ctg gtc gat      720
Trp Ser Val Ile His Gln Glu Ile Val Arg Gln Cys Asp Leu Val Asp
225                 230                 235                 240 ggg gct ctg gat gga atc atc gaa gac cct gat ttc tgt gct cca gtc      768
Gly Ala Leu Asp Gly Ile Ile Glu Asp Pro Asp Phe Cys Ala Pro Val
                245                 250                 255 atc gag cgc ttg atc tgc gac ggg act acc aac ggc acc tct tgt atc      816
Ile Glu Arg Leu Ile Cys Asp Gly Thr Thr Asn Gly Thr Ser Cys Ile
            260                 265                 270 acg gga gcc cag gca gca aag gtc aac cgg gcc ttg agt gac ttc tat      864
Thr Gly Ala Gln Ala Ala Lys Val Asn Arg Ala Leu Ser Asp Phe Tyr
        275                 280                 285 ggc ccc gac ggg aca gtg tac tac ccg cgc ctg aac tat ggg ggt gag      912
Gly Pro Asp Gly Thr Val Tyr Tyr Pro Arg Leu Asn Tyr Gly Gly Glu
    290                 295                 300 gcc gac tcg gct tcc ctg tac ttc acg ggg tcg atg tac agc cgt acg      960
Ala Asp Ser Ala Ser Leu Tyr Phe Thr Gly Ser Met Tyr Ser Arg Thr
305                 310                 315                 320 gag gaa tgg tac aaa tat gtg gtc tat aac gac acc aac tgg aac tcc     1008
Glu Glu Trp Tyr Lys Tyr Val Val Tyr Asn Asp Thr Asn Trp Asn Ser
                325                 330                 335 agc cag tgg acg ctg gag agt gcc aag ctg gcc ctg gag cag aat ccg     1056
Ser Gln Trp Thr Leu Glu Ser Ala Lys Leu Ala Leu Glu Gln Asn Pro
            340                 345                 350 ttc aat atc cag gcg ttt gat ccc aac atc acg gcc ttc cgg gac cgg     1104
Phe Asn Ile Gln Ala Phe Asp Pro Asn Ile Thr Ala Phe Arg Asp Arg
        355                 360                 365 ggt ggc aag ctg ctg tcc tac cac ggc acg cag gat ccc att atc agc     1152
Gly Gly Lys Leu Leu Ser Tyr His Gly Thr Gln Asp Pro Ile Ile Ser
    370                 375                 380 tcc acg gat agc aag ctc tac tac cga cgg gta gcg aat gcc ctg aat     1200
Ser Thr Asp Ser Lys Leu Tyr Tyr Arg Arg Val Ala Asn Ala Leu Asn
385                 390                 395                 400 gcc gcg ccg tcc gag cta gat gag ttc tat cgg ttc ttc cag atc tcc     1248
Ala Ala Pro Ser Glu Leu Asp Glu Phe Tyr Arg Phe Phe Gln Ile Ser
                405                 410                 415 ggc atg ggc cac tgt ggc gat ggc acg gga gca tcg tac atc ggc cag     1296
Gly Met Gly His Cys Gly Asp Gly Thr Gly Ala Ser Tyr Ile Gly Gln
            420                 425                 430 gga tat ggc acg tac acc tcc aag gcg ccc caa gtc aac ctg ctg cgc     1344
Gly Tyr Gly Thr Tyr Thr Ser Lys Ala Pro Gln Val Asn Leu Leu Arg
        435                 440                 445 acg atg gtg gac tgg gtg gaa aac gga aag gcg ccc gag tat atg ccg     1392
Thr Met Val Asp Trp Val Glu Asn Gly Lys Ala Pro Glu Tyr Met Pro
    450                 455                 460 ggc aac aag ctc aac gcg aac ggg tca att gag tac atg cgc aag cac     1440
Gly Asn Lys Leu Asn Ala Asn Gly Ser Ile Glu Tyr Met Arg Lys His
465                 470                 475                 480 tgc cgg tat ccg aag cat aac att cac acg ggg ccg ggt aac tac acc     1488
Cys Arg Tyr Pro Lys His Asn Ile His Thr Gly Pro Gly Asn Tyr Thr
```

-continued

```
                485                      490                      495
gat cct aac tcc tgg act tgc gta ggc tcg act tac tcc agt gga tct      1536
Asp Pro Asn Ser Trp Thr Cys Val Gly Ser Thr Tyr Ser Ser Gly Ser
        500                      505                      510 tct tcg ggg tcg ggg tct agc tcc agc tcg agt tcg act acc act aag      1584
Ser Ser Gly Ser Gly Ser Ser Ser Ser Ser Ser Thr Thr Thr Lys
    515                      520                      525 gcc act tcg acg acc ttg aag act acc tcg acc acc agc agt gga agc      1632
Ala Thr Ser Thr Thr Leu Lys Thr Thr Ser Thr Thr Ser Ser Gly Ser
530                      535                      540 agt tcg aca tcg gcg gcg tcg acc ccg agc tcg acc ggc gag aac aac      1680
Ser Ser Thr Ser Ala Ala Ser Thr Pro Ser Ser Thr Gly Glu Asn Asn
545                      550                      555                  560 ggc ttc tac tac tcc ttc tgg acc gac ggc ggt gga gac gtg acc tac      1728
Gly Phe Tyr Tyr Ser Phe Trp Thr Asp Gly Gly Gly Asp Val Thr Tyr
            565                      570                      575 acc aac gga gat gct ggt gcc tac act gtt gag tgg tcc aac gtg ggc      1776
Thr Asn Gly Asp Ala Gly Ala Tyr Thr Val Glu Trp Ser Asn Val Gly
                580                      585                      590 aac ttt gtc ggt gga aag ggc tgg aac ccc gga agt gcg cag gac atc      1824
Asn Phe Val Gly Gly Lys Gly Trp Asn Pro Gly Ser Ala Gln Asp Ile
                    595                      600                      605 acc tac agc ggc acc ttc acc cct agc ggc aac ggc tac ctc tcc gtc      1872
Thr Tyr Ser Gly Thr Phe Thr Pro Ser Gly Asn Gly Tyr Leu Ser Val
            610                      615                      620 tat ggc tgg acc act gac cct ctg atc gag tac tac atc gtc gag tct      1920
Tyr Gly Trp Thr Thr Asp Pro Leu Ile Glu Tyr Tyr Ile Val Glu Ser
625                      630                      635                  640 tac ggc gac tac aac ccc ggc agt gga ggc acg tac aag ggc acc gtc      1968
Tyr Gly Asp Tyr Asn Pro Gly Ser Gly Gly Thr Tyr Lys Gly Thr Val
                645                      650                      655 acc tcg gac gga tcc gtt tac gat atc tac acg gct acc cgt acc aat      2016
Thr Ser Asp Gly Ser Val Tyr Asp Ile Tyr Thr Ala Thr Arg Thr Asn
                    660                      665                      670 gct gct tcc att cag gga acc gct acc ttc act cag tac tgg tcc gtt      2064
Ala Ala Ser Ile Gln Gly Thr Ala Thr Phe Thr Gln Tyr Trp Ser Val
            675                      680                      685 cgc cag aac aag aga gtt ggc gga acc gtt acc acc tcc aac cac ttc      2112
Arg Gln Asn Lys Arg Val Gly Gly Thr Val Thr Thr Ser Asn His Phe
    690                      695                      700 aat gct tgg gct aag ctg gga atg aac ctg ggt act cac aac tac cag      2160
Asn Ala Trp Ala Lys Leu Gly Met Asn Leu Gly Thr His Asn Tyr Gln
705                      710                      715                  720 atc gtg gct acc gag ggt tac cag agc agt gga tct tcg tcc atc act      2208
Ile Val Ala Thr Glu Gly Tyr Gln Ser Ser Gly Ser Ser Ser Ile Thr
                725                      730                      735 gtt cag ggc tcg act tac tcc agt gga tct tct tcg ggg tcg ggg tct      2256
Val Gln Gly Ser Thr Tyr Ser Ser Gly Ser Ser Ser Gly Ser Gly Ser
            740                      745                      750 agc tcc agc tcg agt tcg act acc act aag gcc act tcg acg acc ttg      2304
Ser Ser Ser Ser Ser Ser Thr Thr Thr Lys Ala Thr Ser Thr Thr Leu
                    755                      760                      765 aag act acc tcg acc acc agc agt gga agc agt tcg aca tcg gcg gcg      2352
Lys Thr Thr Ser Thr Thr Ser Ser Gly Ser Ser Ser Thr Ser Ala Ala
            770                      775                      780 cag gcg tat gga cag tgt ggt gga cag ggc tgg act ggt ccg acc act      2400
Gln Ala Tyr Gly Gln Cys Gly Gly Gln Gly Trp Thr Gly Pro Thr Thr
785                      790                      795                  800 tgt gtg agt ggg tac act tgc acg tat gag aat gcg tac tac tcg cag      2448
Cys Val Ser Gly Tyr Thr Cys Thr Tyr Glu Asn Ala Tyr Tyr Ser Gln
```

```
                        805             810             815
tgt ttg                                                           2454
Cys Leu <210> SEQ ID NO 18
<211> LENGTH: 818
<212> TYPE: PRT
<213> ORGANISM: Aspergillus niger

<400> SEQUENCE: 18

Ala Thr Asp Pro Phe Gln Ser Arg Cys Asn Glu Phe Gln Asn Lys Ile
 1               5                  10                  15

Asp Ile Ala Asn Val Thr Val Arg Ser Val Ala Tyr Val Ala Ala Gly
            20                  25                  30

Gln Asn Ile Ser Gln Ala Glu Val Ala Ser Val Cys Lys Ala Ser Val
        35                  40                  45

Gln Ala Ser Val Asp Leu Cys Arg Val Thr Met Asn Ile Ser Thr Ser
    50                  55                  60

Asp Arg Ser His Leu Trp Ala Glu Ala Trp Leu Pro Arg Asn Tyr Thr
65                  70                  75                  80

Gly Arg Phe Val Ser Thr Gly Asn Gly Gly Leu Ala Gly Cys Val Gln
                85                  90                  95

Glu Thr Asp Leu Asn Phe Ala Ala Asn Phe Gly Phe Ala Thr Val Gly
            100                 105                 110

Thr Asn Gly Gly His Asp Gly Asp Thr Ala Lys Tyr Phe Leu Asn Asn
        115                 120                 125

Ser Glu Val Leu Ala Asp Phe Ala Tyr Arg Ser Val His Glu Gly Thr
    130                 135                 140

Val Val Gly Lys Gln Leu Thr Gln Leu Phe Tyr Asp Glu Gly Tyr Asn
145                 150                 155                 160

Tyr Ser Tyr Tyr Leu Gly Cys Ser Thr Gly Gly Arg Gln Gly Tyr Gln
                165                 170                 175

Gln Val Gln Arg Phe Pro Asp Asp Tyr Asp Gly Val Ile Ala Gly Ser
            180                 185                 190

Ala Ala Met Asn Phe Ile Asn Leu Ile Ser Trp Gly Ala Phe Leu Trp
        195                 200                 205

Lys Ala Thr Gly Leu Ala Asp Asp Pro Asp Phe Ile Ser Ala Asn Leu
210                 215                 220

Trp Ser Val Ile His Gln Glu Ile Val Arg Gln Cys Asp Leu Val Asp
225                 230                 235                 240

Gly Ala Leu Asp Gly Ile Ile Glu Asp Pro Asp Phe Cys Ala Pro Val
                245                 250                 255

Ile Glu Arg Leu Ile Cys Asp Gly Thr Thr Asn Gly Thr Ser Cys Ile
            260                 265                 270

Thr Gly Ala Gln Ala Ala Lys Val Asn Arg Ala Leu Ser Asp Phe Tyr
        275                 280                 285

Gly Pro Asp Gly Thr Val Tyr Tyr Pro Arg Leu Asn Tyr Gly Gly Glu
    290                 295                 300

Ala Asp Ser Ala Ser Leu Tyr Phe Thr Gly Ser Met Tyr Ser Arg Thr
305                 310                 315                 320

Glu Glu Trp Tyr Lys Tyr Val Val Tyr Asn Asp Thr Asn Trp Asn Ser
                325                 330                 335

Ser Gln Trp Thr Leu Glu Ser Ala Lys Leu Ala Leu Glu Gln Asn Pro
            340                 345                 350

Phe Asn Ile Gln Ala Phe Asp Pro Asn Ile Thr Ala Phe Arg Asp Arg
```

```
                355                 360                 365
Gly Gly Lys Leu Leu Ser Tyr His Gly Thr Gln Asp Pro Ile Ile Ser
            370                 375                 380

Ser Thr Asp Ser Lys Leu Tyr Tyr Arg Arg Val Ala Asn Ala Leu Asn
385                 390                 395                 400

Ala Ala Pro Ser Glu Leu Asp Glu Phe Tyr Arg Phe Gln Ile Ser
                405                 410                 415

Gly Met Gly His Cys Gly Asp Gly Thr Gly Ala Ser Tyr Ile Gly Gln
            420                 425                 430

Gly Tyr Gly Thr Tyr Thr Ser Lys Ala Pro Gln Val Asn Leu Leu Arg
            435                 440                 445

Thr Met Val Asp Trp Val Glu Asn Gly Lys Ala Pro Glu Tyr Met Pro
            450                 455                 460

Gly Asn Lys Leu Asn Ala Asn Gly Ser Ile Glu Tyr Met Arg Lys His
465                 470                 475                 480

Cys Arg Tyr Pro Lys His Asn Ile His Thr Gly Pro Gly Asn Tyr Thr
                485                 490                 495

Asp Pro Asn Ser Trp Thr Cys Val Gly Ser Thr Tyr Ser Ser Gly Ser
            500                 505                 510

Ser Ser Gly Ser Gly Ser Ser Ser Ser Ser Ser Thr Thr Thr Lys
            515                 520                 525

Ala Thr Ser Thr Thr Leu Lys Thr Thr Ser Thr Thr Ser Ser Gly Ser
            530                 535                 540

Ser Ser Thr Ser Ala Ala Ser Thr Pro Ser Ser Thr Gly Glu Asn Asn
545                 550                 555                 560

Gly Phe Tyr Tyr Ser Phe Trp Thr Asp Gly Gly Gly Asp Val Thr Tyr
                565                 570                 575

Thr Asn Gly Asp Ala Gly Ala Tyr Thr Val Glu Trp Ser Asn Val Gly
            580                 585                 590

Asn Phe Val Gly Gly Lys Gly Trp Asn Pro Gly Ser Ala Gln Asp Ile
            595                 600                 605

Thr Tyr Ser Gly Thr Phe Thr Pro Ser Gly Asn Gly Tyr Leu Ser Val
            610                 615                 620

Tyr Gly Trp Thr Thr Asp Pro Leu Ile Glu Tyr Tyr Ile Val Glu Ser
625                 630                 635                 640

Tyr Gly Asp Tyr Asn Pro Gly Ser Gly Gly Thr Tyr Lys Gly Thr Val
                645                 650                 655

Thr Ser Asp Gly Ser Val Tyr Asp Ile Tyr Thr Ala Thr Arg Thr Asn
            660                 665                 670

Ala Ala Ser Ile Gln Gly Thr Ala Thr Phe Thr Gln Tyr Trp Ser Val
            675                 680                 685

Arg Gln Asn Lys Arg Val Gly Gly Thr Val Thr Thr Ser Asn His Phe
            690                 695                 700

Asn Ala Trp Ala Lys Leu Gly Met Asn Leu Gly Thr His Asn Tyr Gln
705                 710                 715                 720

Ile Val Ala Thr Glu Gly Tyr Gln Ser Ser Gly Ser Ser Ser Ile Thr
                725                 730                 735

Val Gln Gly Ser Thr Tyr Ser Ser Gly Ser Ser Ser Gly Ser Gly Ser
            740                 745                 750

Ser Ser Ser Ser Ser Ser Thr Thr Lys Ala Thr Ser Thr Thr Leu
            755                 760                 765

Lys Thr Ser Thr Thr Ser Ser Gly Ser Ser Ser Thr Ser Ala Ala
            770                 775                 780
```

```
Gln Ala Tyr Gly Gln Cys Gly Gly Gln Gly Trp Thr Gly Pro Thr Thr
785                 790                 795                 800

Cys Val Ser Gly Tyr Thr Cys Thr Tyr Glu Asn Ala Tyr Ser Gln
            805                 810                 815

Cys Leu

<210> SEQ ID NO 19
<211> LENGTH: 1545
<212> TYPE: DNA
<213> ORGANISM: Aspergillus niger
<220> FEATURE:
<221> NAME/KEY: CDS
<222> LOCATION: (1)..(1545)
<223> OTHER INFORMATION:

<400> SEQUENCE: 19 atg aag caa ttc tct gca aaa tac gcc ctc att ctt ttg gcg act gca      48
Met Lys Gln Phe Ser Ala Lys Tyr Ala Leu Ile Leu Leu Ala Thr Ala
1               5                   10                  15 gga caa gcc ctc gcg gcc tcc acg caa ggc atc tcc gaa gac ctc tac      96
Gly Gln Ala Leu Ala Ala Ser Thr Gln Gly Ile Ser Glu Asp Leu Tyr
            20                  25                  30 aat cgc ttg gta gag atg gcc act atc tcc caa gcc gcc tac gcc gac     144
Asn Arg Leu Val Glu Met Ala Thr Ile Ser Gln Ala Ala Tyr Ala Asp
        35                  40                  45 cta tgc aat att cca tcg act att atc aaa gga gag aaa att tac aac     192
Leu Cys Asn Ile Pro Ser Thr Ile Ile Lys Gly Glu Lys Ile Tyr Asn
    50                  55                  60 gct caa act gat atc aac gga tgg atc ctc cgc gac gac acc agc aaa     240
Ala Gln Thr Asp Ile Asn Gly Trp Ile Leu Arg Asp Asp Thr Ser Lys
65                  70                  75                  80 gaa att atc acc gtc ttc cgt ggc act ggc agt gac aca aac cta cag     288
Glu Ile Ile Thr Val Phe Arg Gly Thr Gly Ser Asp Thr Asn Leu Gln
                85                  90                  95 ctc gat act aac tac acg ctc acg cca ttc gac act cta cct caa tgc     336
Leu Asp Thr Asn Tyr Thr Leu Thr Pro Phe Asp Thr Leu Pro Gln Cys
            100                 105                 110 aac gat tgc gag gta cac ggt gga tac tat att gga tgg atc tca gtc     384
Asn Asp Cys Glu Val His Gly Gly Tyr Tyr Ile Gly Trp Ile Ser Val
        115                 120                 125 caa gac caa gtc gag tcg ctt gtc aaa caa cag gct agc cag tat ccg     432
Gln Asp Gln Val Glu Ser Leu Val Lys Gln Gln Ala Ser Gln Tyr Pro
    130                 135                 140 gac tat gcg ctt acc gtg aca ggc cat agt ctg gga gcg tcg atg gca     480
Asp Tyr Ala Leu Thr Val Thr Gly His Ser Leu Gly Ala Ser Met Ala
145                 150                 155                 160 gca ctc act gcc gcc cag ctg tcc gcg aca tac gac aac gtc cgt ctg     528
Ala Leu Thr Ala Ala Gln Leu Ser Ala Thr Tyr Asp Asn Val Arg Leu
                165                 170                 175 tac aca ttc ggc gaa ccg cgc agc ggc aac cag gcc ttc gcg tcg tac     576
Tyr Thr Phe Gly Glu Pro Arg Ser Gly Asn Gln Ala Phe Ala Ser Tyr
            180                 185                 190 atg aac gat gcg ttc cag gtc tcg agc ccg gag acg acc cag tac ttc     624
Met Asn Asp Ala Phe Gln Val Ser Ser Pro Glu Thr Thr Gln Tyr Phe
        195                 200                 205 cgg gtc act cat tcc aac gac ggc atc cca aac ttg ccc ccg gcg gac     672
Arg Val Thr His Ser Asn Asp Gly Ile Pro Asn Leu Pro Pro Ala Asp
    210                 215                 220 gag ggt tac gcc cat ggt ggt gta gag tac tgg agc gtt gat cct tac     720
Glu Gly Tyr Ala His Gly Gly Val Glu Tyr Trp Ser Val Asp Pro Tyr
225                 230                 235                 240
```

```
agc gcc cag aac acg ttt gtc tgt act ggg gat gaa gta cag tgc tgt    768
Ser Ala Gln Asn Thr Phe Val Cys Thr Gly Asp Glu Val Gln Cys Cys
            245                 250                 255 gag gca cag ggc gga cag ggg gtg aat gat gcg cat act act tat ttt    816
Glu Ala Gln Gly Gly Gln Gly Val Asn Asp Ala His Thr Thr Tyr Phe
        260                 265                 270 ggg atg acg agc gga gct tgt act tgg ggc tcg act tac tcc agt gga    864
Gly Met Thr Ser Gly Ala Cys Thr Trp Gly Ser Thr Tyr Ser Ser Gly
    275                 280                 285 tct tct tcg ggg tcg ggg tct agc tcc agc tcg agt tcg act acc act    912
Ser Ser Ser Gly Ser Gly Ser Ser Ser Ser Ser Ser Thr Thr Thr
290                 295                 300 aag gcc act tcg acg acc ttg aag act acc tcg acc acc agc agt gga    960
Lys Ala Thr Ser Thr Thr Leu Lys Thr Thr Ser Thr Thr Ser Ser Gly
305                 310                 315                 320 agc agt tcg aca tcg gcg gcg tcg acc ccg agc tcg acc ggc gag aac    1008
Ser Ser Ser Thr Ser Ala Ala Ser Thr Pro Ser Ser Thr Gly Glu Asn
                325                 330                 335 aac ggc ttc tac tac tcc ttc tgg acc gac ggc ggt gga gac gtg acc    1056
Asn Gly Phe Tyr Tyr Ser Phe Trp Thr Asp Gly Gly Gly Asp Val Thr
            340                 345                 350 tac acc aac gga gat gct ggt gcc tac act gtt gag tgg tcc aac gtg    1104
Tyr Thr Asn Gly Asp Ala Gly Ala Tyr Thr Val Glu Trp Ser Asn Val
        355                 360                 365 ggc aac ttt gtc ggt gga aag ggc tgg aac ccc gga agt gcg cag gac    1152
Gly Asn Phe Val Gly Gly Lys Gly Trp Asn Pro Gly Ser Ala Gln Asp
    370                 375                 380 atc acc tac agc ggc acc ttc acc cct agc ggc aac ggc tac ctc tcc    1200
Ile Thr Tyr Ser Gly Thr Phe Thr Pro Ser Gly Asn Gly Tyr Leu Ser
385                 390                 395                 400 gtc tat ggc tgg acc act gac cct ctg atc gag tac tac atc gtc gag    1248
Val Tyr Gly Trp Thr Thr Asp Pro Leu Ile Glu Tyr Tyr Ile Val Glu
                405                 410                 415 tct tac ggc gac tac aac ccc ggc agt gga ggc acg tac aag ggc acc    1296
Ser Tyr Gly Asp Tyr Asn Pro Gly Ser Gly Gly Thr Tyr Lys Gly Thr
            420                 425                 430 gtc acc tcg gac gga tcc gtt tac gat atc tac acg gct acc cgt acc    1344
Val Thr Ser Asp Gly Ser Val Tyr Asp Ile Tyr Thr Ala Thr Arg Thr
        435                 440                 445 aat gct gct tcc att cag gga acc gct acc ttc act cag tac tgg tcc    1392
Asn Ala Ala Ser Ile Gln Gly Thr Ala Thr Phe Thr Gln Tyr Trp Ser
    450                 455                 460 gtt cgc cag aac aag aga gtt ggc gga acc gtt acc acc tcc aac cac    1440
Val Arg Gln Asn Lys Arg Val Gly Gly Thr Val Thr Thr Ser Asn His
465                 470                 475                 480 ttc aat gct tgg gct aag ctg gga atg aac ctg ggt act cac aac tac    1488
Phe Asn Ala Trp Ala Lys Leu Gly Met Asn Leu Gly Thr His Asn Tyr
                485                 490                 495 cag atc gtg gct acc gag ggt tac cag agc agt gga tct tcg tcc atc    1536
Gln Ile Val Ala Thr Glu Gly Tyr Gln Ser Ser Gly Ser Ser Ser Ile
            500                 505                 510 act gtt cag                                                        1545
Thr Val Gln
        515

<210> SEQ ID NO 20
<211> LENGTH: 515
<212> TYPE: PRT
<213> ORGANISM: Aspergillus niger

<400> SEQUENCE: 20
```

```
Met Lys Gln Phe Ser Ala Lys Tyr Ala Leu Ile Leu Leu Ala Thr Ala
1               5                   10                  15

Gly Gln Ala Leu Ala Ala Ser Thr Gln Gly Ile Ser Glu Asp Leu Tyr
            20                  25                  30

Asn Arg Leu Val Glu Met Ala Thr Ile Ser Gln Ala Ala Tyr Ala Asp
            35                  40                  45

Leu Cys Asn Ile Pro Ser Thr Ile Ile Lys Gly Glu Lys Ile Tyr Asn
    50                  55                  60

Ala Gln Thr Asp Ile Asn Gly Trp Ile Leu Arg Asp Asp Thr Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Asp Cys Glu Val His Gly Gly Tyr Tyr Ile Gly Trp Ile Ser Val
            115                 120                 125

Gln Asp Gln Val Glu Ser Leu Val Lys Gln Gln Ala Ser Gln Tyr Pro
    130                 135                 140

Asp Tyr Ala Leu Thr Val Thr Gly His Ser Leu Gly Ala Ser Met Ala
145                 150                 155                 160

Ala Leu Thr Ala Ala Gln Leu Ser Ala Thr Tyr Asp Asn Val Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Val Ser Ser Pro Glu Thr Thr Gln Tyr Phe
    195                 200                 205

Arg Val Thr His Ser Asn Asp Gly Ile Pro Asn Leu Pro Pro Ala Asp
210                 215                 220

Glu Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asp Ala His Thr Thr Tyr Phe
            260                 265                 270

Gly Met Thr Ser Gly Ala Cys Thr Trp Gly Ser Thr Tyr Ser Ser Gly
    275                 280                 285

Ser Ser Ser Gly Ser Gly Ser Ser Ser Ser Ser Ser Thr Thr Thr
    290                 295                 300

Lys Ala Thr Ser Thr Thr Leu Lys Thr Thr Thr Ser Thr Ser Ser Gly
305                 310                 315                 320

Ser Ser Ser Thr Ser Ala Ala Ser Thr Pro Ser Ser Thr Gly Glu Asn
                325                 330                 335

Asn Gly Phe Tyr Tyr Ser Phe Trp Thr Asp Gly Gly Asp Val Thr
            340                 345                 350

Tyr Thr Asn Gly Asp Ala Gly Ala Tyr Thr Val Glu Trp Ser Asn Val
            355                 360                 365

Gly Asn Phe Val Gly Gly Lys Gly Trp Asn Pro Gly Ser Ala Gln Asp
    370                 375                 380

Ile Thr Tyr Ser Gly Thr Phe Thr Pro Ser Gly Asn Gly Tyr Leu Ser
385                 390                 395                 400

Val Tyr Gly Trp Thr Thr Asp Pro Leu Ile Glu Tyr Tyr Ile Val Glu
                405                 410                 415

Ser Tyr Gly Asp Tyr Asn Pro Gly Ser Gly Gly Thr Tyr Lys Gly Thr
            420                 425                 430
```

```
Val Thr Ser Asp Gly Ser Val Tyr Asp Ile Tyr Thr Ala Thr Arg Thr
        435                 440                 445

Asn Ala Ala Ser Ile Gln Gly Thr Ala Thr Phe Thr Gln Tyr Trp Ser
    450                 455                 460

Val Arg Gln Asn Lys Arg Val Gly Gly Thr Val Thr Thr Ser Asn His
465                 470                 475                 480

Phe Asn Ala Trp Ala Lys Leu Gly Met Asn Leu Gly Thr His Asn Tyr
                485                 490                 495

Gln Ile Val Ala Thr Glu Gly Tyr Gln Ser Ser Gly Ser Ser Ser Ile
            500                 505                 510

Thr Val Gln
        515

<210> SEQ ID NO 21
<211> LENGTH: 1785
<212> TYPE: DNA
<213> ORGANISM: Aspergillus niger
<220> FEATURE:
<221> NAME/KEY: CDS
<222> LOCATION: (1)..(1785)
<223> OTHER INFORMATION:

<400> SEQUENCE: 21 atg aag caa ttc tct gca aaa tac gcc ctc att ctt ttg gcg act gca      48
Met Lys Gln Phe Ser Ala Lys Tyr Ala Leu Ile Leu Leu Ala Thr Ala
1               5                   10                  15 gga caa gcc ctc gcg gcc tcc acg caa ggc atc tcc gaa gac ctc tac      96
Gly Gln Ala Leu Ala Ala Ser Thr Gln Gly Ile Ser Glu Asp Leu Tyr
            20                  25                  30 aat cgc ttg gta gag atg gcc act atc tcc caa gcc gcc tac gcc gac     144
Asn Arg Leu Val Glu Met Ala Thr Ile Ser Gln Ala Ala Tyr Ala Asp
        35                  40                  45 cta tgc aat att cca tcg act att atc aaa gga gag aaa att tac aac     192
Leu Cys Asn Ile Pro Ser Thr Ile Ile Lys Gly Glu Lys Ile Tyr Asn
    50                  55                  60 gct caa act gat atc aac gga tgg atc ctc cgc gac gac acc agc aaa     240
Ala Gln Thr Asp Ile Asn Gly Trp Ile Leu Arg Asp Asp Thr Ser Lys
65                  70                  75                  80 gaa att atc acc gtc ttc cgt ggc act ggc agt gac aca aac cta cag     288
Glu Ile Ile Thr Val Phe Arg Gly Thr Gly Ser Asp Thr Asn Leu Gln
                85                  90                  95 ctc gat act aac tac acg ctc acg cca ttc gac act cta cct caa tgc     336
Leu Asp Thr Asn Tyr Thr Leu Thr Pro Phe Asp Thr Leu Pro Gln Cys
            100                 105                 110 aac gat tgc gag gta cac ggt gga tac tat att gga tgg atc tca gtc     384
Asn Asp Cys Glu Val His Gly Gly Tyr Tyr Ile Gly Trp Ile Ser Val
        115                 120                 125 caa gac caa gtc gag tcg ctt gtc aaa caa cag gct agc cag tat ccg     432
Gln Asp Gln Val Glu Ser Leu Val Lys Gln Gln Ala Ser Gln Tyr Pro
    130                 135                 140 gac tat gcg ctt acc gtg aca ggc cat agt ctg gga gcg tcg atg gca     480
Asp Tyr Ala Leu Thr Val Thr Gly His Ser Leu Gly Ala Ser Met Ala
145                 150                 155                 160 gca ctc act gcc gcc cag ctg tcc gcg aca tac gac aac gtc cgt ctg     528
Ala Leu Thr Ala Ala Gln Leu Ser Ala Thr Tyr Asp Asn Val Arg Leu
                165                 170                 175 tac aca ttc ggc gaa ccg cgc agc ggc aac cag gcc ttc gcg tcg tac     576
Tyr Thr Phe Gly Glu Pro Arg Ser Gly Asn Gln Ala Phe Ala Ser Tyr
            180                 185                 190 atg aac gat gcg ttc cag gtc tcg agc ccg gag acg acc cag tac ttc     624
```

```
                Met Asn Asp Ala Phe Gln Val Ser Ser Pro Glu Thr Thr Gln Tyr Phe
                        195                 200                 205 cgg gtc act cat tcc aac gac ggc atc cca aac ttg ccc ccg gcg gac       672
Arg Val Thr His Ser Asn Asp Gly Ile Pro Asn Leu Pro Pro Ala Asp
    210                 215                 220 gag ggt tac gcc cat ggt ggt gta gag tac tgg agc gtt gat cct tac       720
Glu Gly Tyr Ala His Gly Gly Val Glu Tyr Trp Ser Val Asp Pro Tyr
225                 230                 235                 240 agc gcc cag aac acg ttt gtc tgt act ggg gat gaa gta cag tgc tgt       768
Ser Ala Gln Asn Thr Phe Val Cys Thr Gly Asp Glu Val Gln Cys Cys
                245                 250                 255 gag gca cag ggc gga cag ggg gtg aat gat gcg cat act act tat ttt       816
Glu Ala Gln Gly Gly Gln Gly Val Asn Asp Ala His Thr Thr Tyr Phe
            260                 265                 270 ggg atg acg agc gga gct tgt act tgg ggc tcg act tac tcc agt gga       864
Gly Met Thr Ser Gly Ala Cys Thr Trp Gly Ser Thr Tyr Ser Ser Gly
        275                 280                 285 tct tct tcg ggg tcg ggg tct agc tcc agc tcg agt tcg act acc act       912
Ser Ser Ser Gly Ser Gly Ser Ser Ser Ser Ser Ser Thr Thr Thr
    290                 295                 300 aag gcc act tcg acg acc ttg aag act acc tcg acc acc agc agt gga       960
Lys Ala Thr Ser Thr Thr Leu Lys Thr Thr Ser Thr Thr Ser Ser Gly
305                 310                 315                 320 agc agt tcg aca tcg gcg gcg tcg acc ccg agc tcg acc ggc gag aac      1008
Ser Ser Ser Thr Ser Ala Ala Ser Thr Pro Ser Ser Thr Gly Glu Asn
                325                 330                 335 aac ggc ttc tac tac tcc ttc tgg acc gac ggc ggt gga gac gtg acc      1056
Asn Gly Phe Tyr Tyr Ser Phe Trp Thr Asp Gly Gly Gly Asp Val Thr
            340                 345                 350 tac acc aac gga gat gct ggt gcc tac act gtt gag tgg tcc aac gtg      1104
Tyr Thr Asn Gly Asp Ala Gly Ala Tyr Thr Val Glu Trp Ser Asn Val
        355                 360                 365 ggc aac ttt gtc ggt gga aag ggc tgg aac ccc gga agt gcg cag gac      1152
Gly Asn Phe Val Gly Gly Lys Gly Trp Asn Pro Gly Ser Ala Gln Asp
    370                 375                 380 atc acc tac agc ggc acc ttc acc cct agc ggc aac ggc tac ctc tcc      1200
Ile Thr Tyr Ser Gly Thr Phe Thr Pro Ser Gly Asn Gly Tyr Leu Ser
385                 390                 395                 400 gtc tat ggc tgg acc act gac cct ctg atc gag tac tac atc gtc gag      1248
Val Tyr Gly Trp Thr Thr Asp Pro Leu Ile Glu Tyr Tyr Ile Val Glu
                405                 410                 415 tct tac ggc gac tac aac ccc ggc agt gga ggc acg tac aag ggc acc      1296
Ser Tyr Gly Asp Tyr Asn Pro Gly Ser Gly Gly Thr Tyr Lys Gly Thr
            420                 425                 430 gtc acc tcg gac gga tcc gtt tac gat atc tac acg gct acc cgt acc      1344
Val Thr Ser Asp Gly Ser Val Tyr Asp Ile Tyr Thr Ala Thr Arg Thr
        435                 440                 445 aat gct gct tcc att cag gga acc gct acc ttc act cag tac tgg tcc      1392
Asn Ala Ala Ser Ile Gln Gly Thr Ala Thr Phe Thr Gln Tyr Trp Ser
    450                 455                 460 gtt cgc cag aac aag aga gtt ggc gga acc gtt acc acc tcc aac cac      1440
Val Arg Gln Asn Lys Arg Val Gly Gly Thr Val Thr Thr Ser Asn His
465                 470                 475                 480 ttc aat gct tgg gct aag ctg gga atg aac ctg ggt act cac aac tac      1488
Phe Asn Ala Trp Ala Lys Leu Gly Met Asn Leu Gly Thr His Asn Tyr
                485                 490                 495 cag atc gtg gct acc gag ggt tac cag agc agt gga tct tcg tcc atc      1536
Gln Ile Val Ala Thr Glu Gly Tyr Gln Ser Ser Gly Ser Ser Ser Ile
            500                 505                 510 act gtt cag ggc tcg act tac tcc agt gga tct tct tcg ggg tcg ggg      1584
```

-continued

```
                Thr Val Gln Gly Ser Thr Tyr Ser Ser Gly Ser Ser Gly Ser Gly
                    515                 520                 525 tct agc tcc agc tcg agt tcg act acc act aag gcc act tcg acg acc       1632
Ser Ser Ser Ser Ser Ser Ser Thr Thr Thr Lys Ala Thr Ser Thr Thr
530                 535                 540 ttg aag act acc tcg acc acc agc agt gga agc agt tcg aca tcg gcg       1680
Leu Lys Thr Thr Ser Thr Thr Ser Ser Gly Ser Ser Thr Ser Ala
545                 550                 555                 560 gcg cag gcg tat gga cag tgt ggt gga cag ggc tgg act ggt ccg acc       1728
Ala Gln Ala Tyr Gly Gln Cys Gly Gly Gln Gly Trp Thr Gly Pro Thr
                565                 570                 575 act tgt gtg agt ggg tac act tgc acg tat gag aat gcg tac tac tcg       1776
Thr Cys Val Ser Gly Tyr Thr Cys Thr Tyr Glu Asn Ala Tyr Tyr Ser
                580                 585                 590 cag tgt ttg                                                            1785
Gln Cys Leu
    595

<210> SEQ ID NO 22
<211> LENGTH: 595
<212> TYPE: PRT
<213> ORGANISM: Aspergillus niger

<400> SEQUENCE: 22

Met Lys Gln Phe Ser Ala Lys Tyr Ala Leu Ile Leu Leu Ala Thr Ala
1               5                   10                  15

Gly Gln Ala Leu Ala Ala Ser Thr Gln Gly Ile Ser Glu Asp Leu Tyr
                20                  25                  30

Asn Arg Leu Val Glu Met Ala Thr Ile Ser Gln Ala Ala Tyr Ala Asp
            35                  40                  45

Leu Cys Asn Ile Pro Ser Thr Ile Ile Lys Gly Glu Lys Ile Tyr Asn
    50                  55                  60

Ala Gln Thr Asp Ile Asn Gly Trp Ile Leu Arg Asp Asp Thr Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Asp Cys Glu Val His Gly Gly Tyr Tyr Ile Gly Trp Ile Ser Val
        115                 120                 125

Gln Asp Gln Val Glu Ser Leu Val Lys Gln Gln Ala Ser Gln Tyr Pro
    130                 135                 140

Asp Tyr Ala Leu Thr Val Thr Gly His Ser Leu Gly Ala Ser Met Ala
145                 150                 155                 160

Ala Leu Thr Ala Ala Gln Leu Ser Ala Thr Tyr Asp Asn Val Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Val Ser Ser Pro Glu Thr Thr Gln Tyr Phe
        195                 200                 205

Arg Val Thr His Ser Asn Asp Gly Ile Pro Asn Leu Pro Pro Ala Asp
    210                 215                 220

Glu Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asp Ala His Thr Thr Tyr Phe
```

-continued

```
                            260                 265                 270
Gly Met Thr Ser Gly Ala Cys Thr Trp Gly Ser Thr Tyr Ser Ser Gly
                275                 280                 285
Ser Ser Ser Gly Ser Gly Ser Ser Ser Ser Ser Ser Thr Thr Thr
            290                 295                 300
Lys Ala Thr Ser Thr Thr Leu Lys Thr Thr Ser Thr Thr Ser Ser Gly
305                 310                 315                 320
Ser Ser Ser Thr Ser Ala Ala Ser Thr Pro Ser Ser Thr Gly Glu Asn
                325                 330                 335
Asn Gly Phe Tyr Tyr Ser Phe Trp Thr Asp Gly Gly Asp Val Thr
            340                 345                 350
Tyr Thr Asn Gly Asp Ala Gly Ala Tyr Thr Val Glu Trp Ser Asn Val
            355                 360                 365
Gly Asn Phe Val Gly Gly Lys Gly Trp Asn Pro Gly Ser Ala Gln Asp
        370                 375                 380
Ile Thr Tyr Ser Gly Thr Phe Thr Pro Ser Gly Asn Gly Tyr Leu Ser
385                 390                 395                 400
Val Tyr Gly Trp Thr Thr Asp Pro Leu Ile Glu Tyr Tyr Ile Val Glu
                405                 410                 415
Ser Tyr Gly Asp Tyr Asn Pro Gly Ser Gly Gly Thr Tyr Lys Gly Thr
                420                 425                 430
Val Thr Ser Asp Gly Ser Val Tyr Asp Ile Tyr Thr Ala Thr Arg Thr
            435                 440                 445
Asn Ala Ala Ser Ile Gln Gly Thr Ala Thr Phe Thr Gln Tyr Trp Ser
        450                 455                 460
Val Arg Gln Asn Lys Arg Val Gly Gly Thr Val Thr Thr Ser Asn His
465                 470                 475                 480
Phe Asn Ala Trp Ala Lys Leu Gly Met Asn Leu Gly Thr His Asn Tyr
                485                 490                 495
Gln Ile Val Ala Thr Glu Gly Tyr Gln Ser Ser Gly Ser Ser Ser Ile
                500                 505                 510
Thr Val Gln Gly Ser Thr Tyr Ser Ser Gly Ser Ser Gly Ser Gly
            515                 520                 525
Ser Ser Ser Ser Ser Ser Ser Thr Thr Thr Lys Ala Thr Ser Thr Thr
        530                 535                 540
Leu Lys Thr Thr Ser Thr Thr Ser Ser Gly Ser Ser Ser Thr Ser Ala
545                 550                 555                 560
Ala Gln Ala Tyr Gly Gln Cys Gly Gly Gln Gly Trp Thr Gly Pro Thr
                565                 570                 575
Thr Cys Val Ser Gly Tyr Thr Cys Thr Tyr Glu Asn Ala Tyr Tyr Ser
            580                 585                 590
Gln Cys Leu
        595

<210> SEQ ID NO 23
<211> LENGTH: 843
<212> TYPE: DNA
<213> ORGANISM: Aspergillus niger
<220> FEATURE:
<221> NAME/KEY: CDS
<222> LOCATION: (1)..(843)
<223> OTHER INFORMATION:

<400> SEQUENCE: 23 atg aag caa ttc tct gca aaa tac gcc ctc att ctt ttg gcg act gca       48
Met Lys Gln Phe Ser Ala Lys Tyr Ala Leu Ile Leu Leu Ala Thr Ala
1               5                   10                  15
```

```
gga caa gcc ctc gcg gcc tcc acg caa ggc atc tcc gaa gac ctc tac     96
Gly Gln Ala Leu Ala Ala Ser Thr Gln Gly Ile Ser Glu Asp Leu Tyr
         20                  25                  30 aat cgc ttg gta gag atg gcc act atc tcc caa gcc gcc tac gcc gac    144
Asn Arg Leu Val Glu Met Ala Thr Ile Ser Gln Ala Ala Tyr Ala Asp
     35                  40                  45 cta tgc aat att cca tcg act att atc aaa gga gag aaa att tac aac    192
Leu Cys Asn Ile Pro Ser Thr Ile Ile Lys Gly Glu Lys Ile Tyr Asn
 50                  55                  60 gct caa act gat atc aac gga tgg atc ctc cgc gac gac acc agc aaa    240
Ala Gln Thr Asp Ile Asn Gly Trp Ile Leu Arg Asp Asp Thr Ser Lys
 65                  70                  75                  80 gaa att atc acc gtc ttc cgt ggc act ggc agt gac aca aac cta cag    288
Glu Ile Ile Thr Val Phe Arg Gly Thr Gly Ser Asp Thr Asn Leu Gln
                 85                  90                  95 ctc gat act aac tac acg ctc acg cca ttc gac act cta cct caa tgc    336
Leu Asp Thr Asn Tyr Thr Leu Thr Pro Phe Asp Thr Leu Pro Gln Cys
            100                 105                 110 aac gat tgc gag gta cac ggt gga tac tat att gga tgg atc tca gtc    384
Asn Asp Cys Glu Val His Gly Gly Tyr Tyr Ile Gly Trp Ile Ser Val
        115                 120                 125 caa gac caa gtc gag tcg ctt gtc aaa caa cag gct agc cag tat ccg    432
Gln Asp Gln Val Glu Ser Leu Val Lys Gln Gln Ala Ser Gln Tyr Pro
    130                 135                 140 gac tat gcg ctt acc gtg aca ggc cat agt ctg gga gcg tcg atg gca    480
Asp Tyr Ala Leu Thr Val Thr Gly His Ser Leu Gly Ala Ser Met Ala
145                 150                 155                 160 gca ctc act gcc gcc cag ctg tcc gcg aca tac gac aac gtc cgt ctg    528
Ala Leu Thr Ala Ala Gln Leu Ser Ala Thr Tyr Asp Asn Val Arg Leu
                165                 170                 175 tac aca ttc ggc gaa ccg cgc agc ggc aac cag gcc ttc gcg tcg tac    576
Tyr Thr Phe Gly Glu Pro Arg Ser Gly Asn Gln Ala Phe Ala Ser Tyr
            180                 185                 190 atg aac gat gcg ttc cag gtc tcg agc ccg gag acg acc cag tac ttc    624
Met Asn Asp Ala Phe Gln Val Ser Ser Pro Glu Thr Thr Gln Tyr Phe
        195                 200                 205 cgg gtc act cat tcc aac gac ggc atc cca aac ttg ccc ccg gcg gac    672
Arg Val Thr His Ser Asn Asp Gly Ile Pro Asn Leu Pro Pro Ala Asp
    210                 215                 220 gag ggt tac gcc cat ggt ggt gta gag tac tgg agc gtt gat cct tac    720
Glu Gly Tyr Ala His Gly Gly Val Glu Tyr Trp Ser Val Asp Pro Tyr
225                 230                 235                 240 agc gcc cag aac acg ttt gtc tgt act ggg gat gaa gta cag tgc tgt    768
Ser Ala Gln Asn Thr Phe Val Cys Thr Gly Asp Glu Val Gln Cys Cys
                245                 250                 255 gag gca cag ggc gga cag ggg gtg aat gat gcg cat act act tat ttt    816
Glu Ala Gln Gly Gly Gln Gly Val Asn Asp Ala His Thr Thr Tyr Phe
            260                 265                 270 ggg atg acg agc gga gct tgt act tgg                                843
Gly Met Thr Ser Gly Ala Cys Thr Trp
        275                 280

<210> SEQ ID NO 24
<211> LENGTH: 281
<212> TYPE: PRT
<213> ORGANISM: Aspergillus niger

<400> SEQUENCE: 24

Met Lys Gln Phe Ser Ala Lys Tyr Ala Leu Ile Leu Leu Ala Thr Ala
1               5                   10                  15
```

```
Gly Gln Ala Leu Ala Ala Ser Thr Gln Gly Ile Ser Glu Asp Leu Tyr
         20                  25                  30

Asn Arg Leu Val Glu Met Ala Thr Ile Ser Gln Ala Ala Tyr Ala Asp
             35                  40                  45

Leu Cys Asn Ile Pro Ser Thr Ile Ile Lys Gly Glu Lys Ile Tyr Asn
 50                  55                  60

Ala Gln Thr Asp Ile Asn Gly Trp Ile Leu Arg Asp Asp Thr Ser Lys
 65                  70                  75                  80

Glu Ile Ile Thr Val Phe Arg Gly Thr Gly Ser Asp Thr Asn Leu Gln
                 85                  90                  95

Leu Asp Thr Asn Tyr Thr Leu Thr Pro Phe Asp Thr Leu Pro Gln Cys
            100                 105                 110

Asn Asp Cys Glu Val His Gly Gly Tyr Tyr Ile Gly Trp Ile Ser Val
        115                 120                 125

Gln Asp Gln Val Glu Ser Leu Val Lys Gln Gln Ala Ser Gln Tyr Pro
130                 135                 140

Asp Tyr Ala Leu Thr Val Thr Gly His Ser Leu Gly Ala Ser Met Ala
145                 150                 155                 160

Ala Leu Thr Ala Ala Gln Leu Ser Ala Thr Tyr Asp Asn Val Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Val Ser Ser Pro Glu Thr Thr Gln Tyr Phe
        195                 200                 205

Arg Val Thr His Ser Asn Asp Gly Ile Pro Asn Leu Pro Pro Ala Asp
    210                 215                 220

Glu Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asp Ala His Thr Thr Tyr Phe
            260                 265                 270

Gly Met Thr Ser Gly Ala Cys Thr Trp
        275                 280

<210> SEQ ID NO 25
<211> LENGTH: 2265
<212> TYPE: DNA
<213> ORGANISM: Aspergillus niger
<220> FEATURE:
<221> NAME/KEY: CDS
<222> LOCATION: (1)..(2265)
<223> OTHER INFORMATION:

<400> SEQUENCE: 25 atg aaa gta gca agt ctc ctc tcc ctg gca ctg cct ggg gca gcc ctc      48
Met Lys Val Ala Ser Leu Leu Ser Leu Ala Leu Pro Gly Ala Ala Leu
 1               5                  10                  15 gct gcg acc gac ccc ttc cag tcg cgg tgc aat gaa ttc cag aac aag      96
Ala Ala Thr Asp Pro Phe Gln Ser Arg Cys Asn Glu Phe Gln Asn Lys
             20                  25                  30 atc gac atc gcc aat gtc acc gtc aga tcg gtc gca tac gtt gct gct     144
Ile Asp Ile Ala Asn Val Thr Val Arg Ser Val Ala Tyr Val Ala Ala
         35                  40                  45 gga cag aac atc tcc caa gcg gag gtc gcc tcc gtg tgt aaa gca tcg     192
Gly Gln Asn Ile Ser Gln Ala Glu Val Ala Ser Val Cys Lys Ala Ser
 50                  55                  60 gtt caa gcc agt gtc gac ctg tgc cgg gta acc atg aac atc tcg acg     240
```

```
Val Gln Ala Ser Val Asp Leu Cys Arg Val Thr Met Asn Ile Ser Thr
 65                  70                  75                  80 tcg gat cgc agc cat ctg tgg gct gag gcc tgg ctc cca aga aat tat       288
Ser Asp Arg Ser His Leu Trp Ala Glu Ala Trp Leu Pro Arg Asn Tyr
                     85                  90                  95 acc ggt cgc ttc gtg agc acg ggg aat gga ggt cta gcc ggc tgt gtc       336
Thr Gly Arg Phe Val Ser Thr Gly Asn Gly Gly Leu Ala Gly Cys Val
                100                 105                 110 caa gaa acg gac ctc aac ttt gca gcc aac ttt ggt ttc gct acc gtg       384
Gln Glu Thr Asp Leu Asn Phe Ala Ala Asn Phe Gly Phe Ala Thr Val
            115                 120                 125 ggc acc aac ggt gga cat gac ggg gac acg gcc aaa tac ttc ctc aac       432
Gly Thr Asn Gly Gly His Asp Gly Asp Thr Ala Lys Tyr Phe Leu Asn
        130                 135                 140 aac tcg gag gtt ctg gcc gat ttt gcc tat cgc tca gtg cac gaa ggg       480
Asn Ser Glu Val Leu Ala Asp Phe Ala Tyr Arg Ser Val His Glu Gly
145                 150                 155                 160 acc gtg gtg ggt aag caa cta act caa ttg ttt tat gac gag gga tac       528
Thr Val Val Gly Lys Gln Leu Thr Gln Leu Phe Tyr Asp Glu Gly Tyr
                165                 170                 175 aac tac tcc tac tat ttg ggt tgc tcc acc gga ggc cgc caa ggc tac       576
Asn Tyr Ser Tyr Tyr Leu Gly Cys Ser Thr Gly Gly Arg Gln Gly Tyr
                180                 185                 190 cag caa gtc caa cgg ttt ccc gac gac tat gac gga gtg att gcg ggc       624
Gln Gln Val Gln Arg Phe Pro Asp Asp Tyr Asp Gly Val Ile Ala Gly
            195                 200                 205 tcc gca gcg atg aac ttt atc aac ctg atc tcc tgg ggg gcc ttc ttg       672
Ser Ala Ala Met Asn Phe Ile Asn Leu Ile Ser Trp Gly Ala Phe Leu
        210                 215                 220 tgg aag gcg acg ggg tta gcg gat gat cca gac ttt atc tct gca aac       720
Trp Lys Ala Thr Gly Leu Ala Asp Asp Pro Asp Phe Ile Ser Ala Asn
225                 230                 235                 240 ctg tgg tcc gta atc cac cag gag att gtt cgt cag tgc gac ctg gtc       768
Leu Trp Ser Val Ile His Gln Glu Ile Val Arg Gln Cys Asp Leu Val
                245                 250                 255 gat ggg gct ctg gat gga atc atc gaa gac cct gat ttc tgt gct cca       816
Asp Gly Ala Leu Asp Gly Ile Ile Glu Asp Pro Asp Phe Cys Ala Pro
                260                 265                 270 gtc atc gag cgc ttg atc tgc gac ggg act acc aac ggc acc tct tgt       864
Val Ile Glu Arg Leu Ile Cys Asp Gly Thr Thr Asn Gly Thr Ser Cys
            275                 280                 285 atc acg gga gcc cag gca gca aag gtc aac cgg gcc ttg agt gac ttc       912
Ile Thr Gly Ala Gln Ala Ala Lys Val Asn Arg Ala Leu Ser Asp Phe
        290                 295                 300 tat ggc ccc gac ggg aca gtg tac tac ccg cgc ctg aac tat ggg ggt       960
Tyr Gly Pro Asp Gly Thr Val Tyr Tyr Pro Arg Leu Asn Tyr Gly Gly
305                 310                 315                 320 gag gcc gac tcg gct tcc ctg tac ttc acg ggg tcg atg tac agc cgt      1008
Glu Ala Asp Ser Ala Ser Leu Tyr Phe Thr Gly Ser Met Tyr Ser Arg
                325                 330                 335 acg gag gaa tgg tac aaa tat gtg gtc tat aac gac acc aac tgg aac      1056
Thr Glu Glu Trp Tyr Lys Tyr Val Val Tyr Asn Asp Thr Asn Trp Asn
                340                 345                 350 tcc agc cag tgg acg ctg gag agt gcc aag ctg gcc ctg gag cag aat      1104
Ser Ser Gln Trp Thr Leu Glu Ser Ala Lys Leu Ala Leu Glu Gln Asn
            355                 360                 365 ccg ttc aat atc cag gcg ttt gat ccc aac atc acg gcc ttc cgg gac      1152
Pro Phe Asn Ile Gln Ala Phe Asp Pro Asn Ile Thr Ala Phe Arg Asp
        370                 375                 380 cgg ggt ggc aag ctg ctg tcc tac cac ggc acg cag gat ccc att atc      1200
```

```
                Arg Gly Gly Lys Leu Leu Ser Tyr His Gly Thr Gln Asp Pro Ile Ile
                385                 390                 395                 400 agc tcc acg gat agc aag ctc tac tac cga cgg gta gcg aat gcc ctg          1248
Ser Ser Thr Asp Ser Lys Leu Tyr Tyr Arg Arg Val Ala Asn Ala Leu
                    405                 410                 415 aat gcc gcg ccg tcc gag cta gat gag ttt tat cgg ttc ttc cag atc          1296
Asn Ala Ala Pro Ser Glu Leu Asp Glu Phe Tyr Arg Phe Phe Gln Ile
                420                 425                 430 tcc ggc atg ggc cac tgt ggc gat ggc acg gga gca tcg tac atc ggc          1344
Ser Gly Met Gly His Cys Gly Asp Gly Thr Gly Ala Ser Tyr Ile Gly
            435                 440                 445 cag gga tat ggc acg tac acc tcc aag gcg ccc caa gtc aac ctg ctg          1392
Gln Gly Tyr Gly Thr Tyr Thr Ser Lys Ala Pro Gln Val Asn Leu Leu
        450                 455                 460 cgc acg atg gtg gac tgg gtg gaa aac gga aag gcg ccc gag tat atg          1440
Arg Thr Met Val Asp Trp Val Glu Asn Gly Lys Ala Pro Glu Tyr Met
465                 470                 475                 480 ccg ggc aac aag ctc aac gcg aac ggg tca att gag tac atg cgc aag          1488
Pro Gly Asn Lys Leu Asn Ala Asn Gly Ser Ile Glu Tyr Met Arg Lys
                    485                 490                 495 cac tgc cgg tat ccg aag cat aac att cac acg ggg ccg ggt aac tac          1536
His Cys Arg Tyr Pro Lys His Asn Ile His Thr Gly Pro Gly Asn Tyr
                500                 505                 510 acc gat cct aac tcc tgg act tgc gta ggc tcg act tac tcc agt gga          1584
Thr Asp Pro Asn Ser Trp Thr Cys Val Gly Ser Thr Tyr Ser Ser Gly
            515                 520                 525 tct tct tcg ggg tcg ggg tct agc tcc agc tcg agt tcg act acc act          1632
Ser Ser Ser Gly Ser Gly Ser Ser Ser Ser Ser Ser Thr Thr Thr
        530                 535                 540 aag gcc act tcg acg acc ttg aag act acc tcg acc acc agc agt gga          1680
Lys Ala Thr Ser Thr Thr Leu Lys Thr Thr Ser Thr Thr Ser Ser Gly
545                 550                 555                 560 agc agt tcg aca tcg gcg gcg tcg acc ccg agc tcg acc ggc gag aac          1728
Ser Ser Ser Thr Ser Ala Ala Ser Thr Pro Ser Ser Thr Gly Glu Asn
                    565                 570                 575 aac ggc ttc tac tac tcc ttc tgg acc gac ggc ggt gga gac gtg acc          1776
Asn Gly Phe Tyr Tyr Ser Phe Trp Thr Asp Gly Gly Gly Asp Val Thr
                580                 585                 590 tac acc aac gga gat gct ggt gcc tac act gtt gag tgg tcc aac gtg          1824
Tyr Thr Asn Gly Asp Ala Gly Ala Tyr Thr Val Glu Trp Ser Asn Val
            595                 600                 605 ggc aac ttt gtc ggt gga aag ggc tgg aac ccc gga agt gcg cag gac          1872
Gly Asn Phe Val Gly Gly Lys Gly Trp Asn Pro Gly Ser Ala Gln Asp
        610                 615                 620 atc acc tac agc ggc acc ttc acc cct agc ggc aac ggc tac ctc tcc          1920
Ile Thr Tyr Ser Gly Thr Phe Thr Pro Ser Gly Asn Gly Tyr Leu Ser
625                 630                 635                 640 gtc tat ggc tgg acc act gac cct ctg atc gag tac tac atc gtc gag          1968
Val Tyr Gly Trp Thr Thr Asp Pro Leu Ile Glu Tyr Tyr Ile Val Glu
                    645                 650                 655 tct tac ggc gac tac aac ccc ggc agt gga ggc acg tac aag ggc acc          2016
Ser Tyr Gly Asp Tyr Asn Pro Gly Ser Gly Gly Thr Tyr Lys Gly Thr
                660                 665                 670 gtc acc tcg gac gga tcc gtt tac gat atc tac acg gct acc cgt acc          2064
Val Thr Ser Asp Gly Ser Val Tyr Asp Ile Tyr Thr Ala Thr Arg Thr
            675                 680                 685 aat gct gct tcc att cag gga acc gct acc ttc act cag tac tgg tcc          2112
Asn Ala Ala Ser Ile Gln Gly Thr Ala Thr Phe Thr Gln Tyr Trp Ser
        690                 695                 700 gtt cgc cag aac aag aga gtt ggc gga acc gtt acc acc tcc aac cac          2160
```

-continued

```
Val Arg Gln Asn Lys Arg Val Gly Gly Thr Val Thr Thr Ser Asn His
705                 710                 715                 720 ttc aat gct tgg gct aag ctg gga atg aac ctg ggt act cac aac tac    2208
Phe Asn Ala Trp Ala Lys Leu Gly Met Asn Leu Gly Thr His Asn Tyr
                725                 730                 735 cag atc gtg gct acc gag ggt tac cag agc agt gga tct tcg tcc atc    2256
Gln Ile Val Ala Thr Glu Gly Tyr Gln Ser Ser Gly Ser Ser Ser Ile
            740                 745                 750 act gtt cag                                                        2265
Thr Val Gln
        755

<210> SEQ ID NO 26
<211> LENGTH: 755
<212> TYPE: PRT
<213> ORGANISM: Aspergillus niger

<400> SEQUENCE: 26

Met Lys Val Ala Ser Leu Leu Ser Leu Ala Leu Pro Gly Ala Ala Leu
1               5                   10                  15

Ala Ala Thr Asp Pro Phe Gln Ser Arg Cys Asn Glu Phe Gln Asn Lys
            20                  25                  30

Ile Asp Ile Ala Asn Val Thr Val Arg Ser Val Ala Tyr Val Ala Ala
        35                  40                  45

Gly Gln Asn Ile Ser Gln Ala Glu Val Ala Ser Val Cys Lys Ala Ser
    50                  55                  60

Val Gln Ala Ser Val Asp Leu Cys Arg Val Thr Met Asn Ile Ser Thr
65                  70                  75                  80

Ser Asp Arg Ser His Leu Trp Ala Glu Ala Trp Leu Pro Arg Asn Tyr
                85                  90                  95

Thr Gly Arg Phe Val Ser Thr Gly Asn Gly Gly Leu Ala Gly Cys Val
            100                 105                 110

Gln Glu Thr Asp Leu Asn Phe Ala Ala Asn Phe Gly Phe Ala Thr Val
        115                 120                 125

Gly Thr Asn Gly Gly His Asp Gly Asp Thr Ala Lys Tyr Phe Leu Asn
    130                 135                 140

Asn Ser Glu Val Leu Ala Asp Phe Ala Tyr Arg Ser Val His Glu Gly
145                 150                 155                 160

Thr Val Val Gly Lys Gln Leu Thr Gln Leu Phe Tyr Asp Glu Gly Tyr
                165                 170                 175

Asn Tyr Ser Tyr Tyr Leu Gly Cys Ser Thr Gly Gly Arg Gln Gly Tyr
            180                 185                 190

Gln Gln Val Gln Arg Phe Pro Asp Asp Tyr Asp Gly Val Ile Ala Gly
        195                 200                 205

Ser Ala Ala Met Asn Phe Ile Asn Leu Ile Ser Trp Gly Ala Phe Leu
    210                 215                 220

Trp Lys Ala Thr Gly Leu Ala Asp Asp Pro Asp Phe Ile Ser Ala Asn
225                 230                 235                 240

Leu Trp Ser Val Ile His Gln Glu Ile Val Arg Gln Cys Asp Leu Val
                245                 250                 255

Asp Gly Ala Leu Asp Gly Ile Ile Glu Asp Pro Asp Phe Cys Ala Pro
            260                 265                 270

Val Ile Glu Arg Leu Ile Cys Asp Gly Thr Thr Asn Gly Thr Ser Cys
        275                 280                 285

Ile Thr Gly Ala Gln Ala Ala Lys Val Asn Arg Ala Leu Ser Asp Phe
    290                 295                 300
```

-continued

```
Tyr Gly Pro Asp Gly Thr Val Tyr Tyr Pro Arg Leu Asn Tyr Gly Gly
305                 310                 315                 320

Glu Ala Asp Ser Ala Ser Leu Tyr Phe Thr Gly Ser Met Tyr Ser Arg
                325                 330                 335

Thr Glu Glu Trp Tyr Lys Tyr Val Val Tyr Asn Asp Thr Asn Trp Asn
            340                 345                 350

Ser Ser Gln Trp Thr Leu Glu Ser Ala Lys Leu Ala Leu Glu Gln Asn
        355                 360                 365

Pro Phe Asn Ile Gln Ala Phe Asp Pro Asn Ile Thr Ala Phe Arg Asp
    370                 375                 380

Arg Gly Gly Lys Leu Leu Ser Tyr His Gly Thr Gln Asp Pro Ile Ile
385                 390                 395                 400

Ser Ser Thr Asp Ser Lys Leu Tyr Tyr Arg Arg Val Ala Asn Ala Leu
                405                 410                 415

Asn Ala Ala Pro Ser Glu Leu Asp Glu Phe Tyr Arg Phe Phe Gln Ile
            420                 425                 430

Ser Gly Met Gly His Cys Gly Asp Gly Thr Gly Ala Ser Tyr Ile Gly
        435                 440                 445

Gln Gly Tyr Gly Thr Tyr Thr Ser Lys Ala Pro Gln Val Asn Leu Leu
    450                 455                 460

Arg Thr Met Val Asp Trp Val Glu Asn Gly Lys Ala Pro Glu Tyr Met
465                 470                 475                 480

Pro Gly Asn Lys Leu Asn Ala Asn Gly Ser Ile Glu Tyr Met Arg Lys
                485                 490                 495

His Cys Arg Tyr Pro Lys His Asn Ile His Thr Gly Pro Gly Asn Tyr
            500                 505                 510

Thr Asp Pro Asn Ser Trp Thr Cys Val Gly Ser Thr Tyr Ser Ser Gly
        515                 520                 525

Ser Ser Ser Gly Ser Gly Ser Ser Ser Ser Ser Ser Thr Thr Thr
    530                 535                 540

Lys Ala Thr Ser Thr Thr Leu Lys Thr Thr Ser Thr Thr Ser Ser Gly
545                 550                 555                 560

Ser Ser Ser Thr Ser Ala Ala Ser Thr Pro Ser Ser Thr Gly Glu Asn
                565                 570                 575

Asn Gly Phe Tyr Tyr Ser Phe Trp Thr Asp Gly Gly Asp Val Thr
            580                 585                 590

Tyr Thr Asn Gly Asp Ala Gly Ala Tyr Thr Val Glu Trp Ser Asn Val
        595                 600                 605

Gly Asn Phe Val Gly Gly Lys Gly Trp Asn Pro Gly Ser Ala Gln Asp
    610                 615                 620

Ile Thr Tyr Ser Gly Thr Phe Thr Pro Ser Gly Asn Gly Tyr Leu Ser
625                 630                 635                 640

Val Tyr Gly Trp Thr Thr Asp Pro Leu Ile Glu Tyr Tyr Ile Val Glu
                645                 650                 655

Ser Tyr Gly Asp Tyr Asn Pro Gly Ser Gly Thr Tyr Lys Gly Thr
            660                 665                 670

Val Thr Ser Asp Gly Ser Val Tyr Asp Ile Tyr Thr Ala Thr Arg Thr
        675                 680                 685

Asn Ala Ala Ser Ile Gln Gly Thr Ala Thr Phe Thr Gln Tyr Trp Ser
    690                 695                 700

Val Arg Gln Asn Lys Arg Val Gly Gly Thr Val Thr Thr Ser Asn His
705                 710                 715                 720

Phe Asn Ala Trp Ala Lys Leu Gly Met Asn Leu Gly Thr His Asn Tyr
                725                 730                 735
```

```
Gln Ile Val Ala Thr Glu Gly Tyr Gln Ser Ser Gly Ser Ser Ser Ile
                740                 745                 750

Thr Val Gln
        755

<210> SEQ ID NO 27
<211> LENGTH: 2505
<212> TYPE: DNA
<213> ORGANISM: Aspergillus niger
<220> FEATURE:
<221> NAME/KEY: CDS
<222> LOCATION: (1)..(2505)
<223> OTHER INFORMATION:

<400> SEQUENCE: 27 atg aaa gta gca agt ctc ctc tcc ctg gca ctg cct ggg gca gcc ctc       48
Met Lys Val Ala Ser Leu Leu Ser Leu Ala Leu Pro Gly Ala Ala Leu
1               5                   10                  15 gct gcg acc gac ccc ttc cag tcg cgg tgc aat gaa ttc cag aac aag       96
Ala Ala Thr Asp Pro Phe Gln Ser Arg Cys Asn Glu Phe Gln Asn Lys
            20                  25                  30 atc gac atc gcc aat gtc acc gtc aga tcg gtc gca tac gtt gct gct      144
Ile Asp Ile Ala Asn Val Thr Val Arg Ser Val Ala Tyr Val Ala Ala
        35                  40                  45 gga cag aac atc tcc caa gcg gag gtc gcc tcc gtg tgt aaa gca tcg      192
Gly Gln Asn Ile Ser Gln Ala Glu Val Ala Ser Val Cys Lys Ala Ser
    50                  55                  60 gtt caa gcc agt gtc gac ctg tgc cgg gta acc atg aac atc tcg acg      240
Val Gln Ala Ser Val Asp Leu Cys Arg Val Thr Met Asn Ile Ser Thr
65                  70                  75                  80 tcg gat cgc agc cat ctg tgg gct gag gcc tgg ctc cca aga aat tat      288
Ser Asp Arg Ser His Leu Trp Ala Glu Ala Trp Leu Pro Arg Asn Tyr
                85                  90                  95 acc ggt cgc ttc gtg agc acg ggg aat gga ggt cta gcc ggc tgt gtc      336
Thr Gly Arg Phe Val Ser Thr Gly Asn Gly Gly Leu Ala Gly Cys Val
            100                 105                 110 caa gaa acg gac ctc aac ttt gca gcc aac ttt ggt ttc gct acc gtg      384
Gln Glu Thr Asp Leu Asn Phe Ala Ala Asn Phe Gly Phe Ala Thr Val
        115                 120                 125 ggc acc aac ggt gga cat gac ggg gac acg gcc aaa tac ttc ctc aac      432
Gly Thr Asn Gly Gly His Asp Gly Asp Thr Ala Lys Tyr Phe Leu Asn
    130                 135                 140 aac tcg gag gtt ctg gcc gat ttt gcc tat cgc tca gtg cac gaa ggg      480
Asn Ser Glu Val Leu Ala Asp Phe Ala Tyr Arg Ser Val His Glu Gly
145                 150                 155                 160 acc gtg gtg ggt aag caa cta act caa ttg ttt tat gac gag gga tac      528
Thr Val Val Gly Lys Gln Leu Thr Gln Leu Phe Tyr Asp Glu Gly Tyr
                165                 170                 175 aac tac tcc tac tat ttg ggt tgc tcc acc gga ggc cgc caa ggc tac      576
Asn Tyr Ser Tyr Tyr Leu Gly Cys Ser Thr Gly Gly Arg Gln Gly Tyr
            180                 185                 190 cag caa gtc caa cgg ttt ccc gac gac tat gac gga gtg att gcg ggc      624
Gln Gln Val Gln Arg Phe Pro Asp Asp Tyr Asp Gly Val Ile Ala Gly
        195                 200                 205 tcc gca gcg atg aac ttt atc aac ctg atc tcc tgg ggg gcc ttc ttg      672
Ser Ala Ala Met Asn Phe Ile Asn Leu Ile Ser Trp Gly Ala Phe Leu
    210                 215                 220 tgg aag gcg acg ggg tta gcg gat gat cca gac ttt atc tct gca aac      720
Trp Lys Ala Thr Gly Leu Ala Asp Asp Pro Asp Phe Ile Ser Ala Asn
225                 230                 235                 240 ctg tgg tcc gta atc cac cag gag att gtt cgt cag tgc gac ctg gtc      768
```

-continued

```
                Leu Trp Ser Val Ile His Gln Glu Ile Val Arg Gln Cys Asp Leu Val
                                245                 250                 255 gat ggg gct ctg gat gga atc atc gaa gac cct gat ttc tgt gct cca        816
Asp Gly Ala Leu Asp Gly Ile Ile Glu Asp Pro Asp Phe Cys Ala Pro
                260                 265                 270 gtc atc gag cgc ttg atc tgc gac ggg act acc aac ggc acc tct tgt        864
Val Ile Glu Arg Leu Ile Cys Asp Gly Thr Thr Asn Gly Thr Ser Cys
            275                 280                 285 atc acg gga gcc cag gca gca aag gtc aac cgg gcc ttg agt gac ttc        912
Ile Thr Gly Ala Gln Ala Ala Lys Val Asn Arg Ala Leu Ser Asp Phe
        290                 295                 300 tat ggc ccc gac ggg aca gtg tac tac ccg cgc ctg aac tat ggg ggt        960
Tyr Gly Pro Asp Gly Thr Val Tyr Tyr Pro Arg Leu Asn Tyr Gly Gly
305                 310                 315                 320 gag gcc gac tcg gct tcc ctg tac ttc acg ggg tcg atg tac agc cgt       1008
Glu Ala Asp Ser Ala Ser Leu Tyr Phe Thr Gly Ser Met Tyr Ser Arg
                325                 330                 335 acg gag gaa tgg tac aaa tat gtc gtc tat aac gac acc aac tgg aac       1056
Thr Glu Glu Trp Tyr Lys Tyr Val Val Tyr Asn Asp Thr Asn Trp Asn
                340                 345                 350 tcc agc cag tgg acg ctg gag agt gcc aag ctg gcc ctg gag cag aat       1104
Ser Ser Gln Trp Thr Leu Glu Ser Ala Lys Leu Ala Leu Glu Gln Asn
            355                 360                 365 ccg ttc aat atc cag gcg ttt gat ccc aac atc acg gcc ttc cgg gac       1152
Pro Phe Asn Ile Gln Ala Phe Asp Pro Asn Ile Thr Ala Phe Arg Asp
        370                 375                 380 cgg ggt ggc aag ctg ctg tcc tac cac ggc acg cag gat ccc att atc       1200
Arg Gly Gly Lys Leu Leu Ser Tyr His Gly Thr Gln Asp Pro Ile Ile
385                 390                 395                 400 agc tcc acg gat agc aag ctc tac tac cga cgg gta gcg aat gcc ctg       1248
Ser Ser Thr Asp Ser Lys Leu Tyr Tyr Arg Arg Val Ala Asn Ala Leu
                405                 410                 415 aat gcc gcg ccg tcc gag cta gat gag ttc tat cgg ttc ttc cag atc       1296
Asn Ala Ala Pro Ser Glu Leu Asp Glu Phe Tyr Arg Phe Phe Gln Ile
                420                 425                 430 tcc ggc atg ggc cac tgt ggc gat ggc acg gga gca tcg tac atc ggc       1344
Ser Gly Met Gly His Cys Gly Asp Gly Thr Gly Ala Ser Tyr Ile Gly
            435                 440                 445 cag gga tat ggc acg tac acc tcc aag gcg ccc caa gtc aac ctg ctg       1392
Gln Gly Tyr Gly Thr Tyr Thr Ser Lys Ala Pro Gln Val Asn Leu Leu
        450                 455                 460 cgc acg atg gtg gac tgg gtg gaa aac gga aag gcg ccc gag tat atg       1440
Arg Thr Met Val Asp Trp Val Glu Asn Gly Lys Ala Pro Glu Tyr Met
465                 470                 475                 480 ccg ggc aac aag ctc aac gcg aac ggg tca att gag tac atg cgc aag       1488
Pro Gly Asn Lys Leu Asn Ala Asn Gly Ser Ile Glu Tyr Met Arg Lys
                485                 490                 495 cac tgc cgg tat ccg aag cat aac att cac acg ggg ccg ggt aac tac       1536
His Cys Arg Tyr Pro Lys His Asn Ile His Thr Gly Pro Gly Asn Tyr
                500                 505                 510 acc gat cct aac tcc tgg act tgc gta ggc tcg act tac tcc agt gga       1584
Thr Asp Pro Asn Ser Trp Thr Cys Val Gly Ser Thr Tyr Ser Ser Gly
            515                 520                 525 tct tct tcg ggg tcg ggg tct agc tcc agc tcg agt tcg act acc act       1632
Ser Ser Ser Gly Ser Gly Ser Ser Ser Ser Ser Ser Thr Thr Thr
        530                 535                 540 aag gcc act tcg acg acc ttg aag act acc tcg acc acc agc agt gga       1680
Lys Ala Thr Ser Thr Thr Leu Lys Thr Thr Ser Thr Thr Ser Ser Gly
545                 550                 555                 560 agc agt tcg aca tcg gcg gcg tcg acc ccg agc tcg acc ggc gag aac       1728
```

-continued

| | | | | | | | | | | | | | |
|---|---|---|---|---|---|---|---|---|---|---|---|---|---|
|Ser|Ser|Ser|Thr|Ser|Ala|Ala|Ser|Thr|Pro|Ser|Ser|Thr|Gly|Glu|Asn|
| | | |565| | | |570| | | |575| | |

```
aac ggc ttc tac tac tcc ttc tgg acc gac ggc ggt gga gac gtg acc      1776
Asn Gly Phe Tyr Tyr Ser Phe Trp Thr Asp Gly Gly Asp Val Thr
            580                 585                 590 tac acc aac gga gat gct ggt gcc tac act gtt gag tgg tcc aac gtg      1824
Tyr Thr Asn Gly Asp Ala Gly Ala Tyr Thr Val Glu Trp Ser Asn Val
        595                 600                 605 ggc aac ttt gtc ggt gga aag ggc tgg aac ccc gga agt gcg cag gac      1872
Gly Asn Phe Val Gly Gly Lys Gly Trp Asn Pro Gly Ser Ala Gln Asp
    610                 615                 620 atc acc tac agc ggc acc ttc acc cct agc ggc aac ggc tac ctc tcc      1920
Ile Thr Tyr Ser Gly Thr Phe Thr Pro Ser Gly Asn Gly Tyr Leu Ser
625                 630                 635                 640 gtc tat ggc tgg acc act gac cct ctg atc gag tac tac atc gtc gag      1968
Val Tyr Gly Trp Thr Thr Asp Pro Leu Ile Glu Tyr Tyr Ile Val Glu
                645                 650                 655 tct tac ggc gac tac aac ccc ggc agt gga ggc acg tac aag ggc acc      2016
Ser Tyr Gly Asp Tyr Asn Pro Gly Ser Gly Gly Thr Tyr Lys Gly Thr
            660                 665                 670 gtc acc tcg gac gga tcc gtt tac gat atc tac acg gct acc cgt acc      2064
Val Thr Ser Asp Gly Ser Val Tyr Asp Ile Tyr Thr Ala Thr Arg Thr
        675                 680                 685 aat gct gct tcc att cag gga acc gct acc ttc act cag tac tgg tcc      2112
Asn Ala Ala Ser Ile Gln Gly Thr Ala Thr Phe Thr Gln Tyr Trp Ser
    690                 695                 700 gtt cgc cag aac aag aga gtt ggc gga acc gtt acc acc tcc aac cac      2160
Val Arg Gln Asn Lys Arg Val Gly Gly Thr Val Thr Thr Ser Asn His
705                 710                 715                 720 ttc aat gct tgg gct aag ctg gga atg aac ctg ggt act cac aac tac      2208
Phe Asn Ala Trp Ala Lys Leu Gly Met Asn Leu Gly Thr His Asn Tyr
                725                 730                 735 cag atc gtg gct acc gag ggt tac cag agc agt gga tct tcg tcc atc      2256
Gln Ile Val Ala Thr Glu Gly Tyr Gln Ser Ser Gly Ser Ser Ser Ile
            740                 745                 750 act gtt cag ggc tcg act tac tcc agt gga tct tct tcg ggg tcg ggg      2304
Thr Val Gln Gly Ser Thr Tyr Ser Ser Gly Ser Ser Ser Gly Ser Gly
        755                 760                 765 tct agc tcc agc tcg agt tcg act acc act aag gcc act tcg acg acc      2352
Ser Ser Ser Ser Ser Ser Ser Thr Thr Thr Lys Ala Thr Ser Thr Thr
    770                 775                 780 ttg aag act acc tcg acc acc agc agt gga agc agt tcg aca tcg gcg      2400
Leu Lys Thr Thr Ser Thr Thr Ser Ser Gly Ser Ser Ser Thr Ser Ala
785                 790                 795                 800 gcg cag gcg tat gga cag tgt ggt gga cag ggc tgg act ggt ccg acc      2448
Ala Gln Ala Tyr Gly Gln Cys Gly Gly Gln Gly Trp Thr Gly Pro Thr
                805                 810                 815 act tgt gtg agt ggg tac act tgc acg tat gag aat gcg tac tac tcg      2496
Thr Cys Val Ser Gly Tyr Thr Cys Thr Tyr Glu Asn Ala Tyr Tyr Ser
            820                 825                 830 cag tgt ttg                                                          2505
Gln Cys Leu
    835

<210> SEQ ID NO 28
<211> LENGTH: 835
<212> TYPE: PRT
<213> ORGANISM: Aspergillus niger

<400> SEQUENCE: 28

Met Lys Val Ala Ser Leu Leu Ser Leu Ala Leu Pro Gly Ala Ala Leu
```

```
1               5                   10                  15
Ala Ala Thr Asp Pro Phe Gln Ser Arg Cys Asn Glu Phe Gln Asn Lys
                    20                  25                  30

Ile Asp Ile Ala Asn Val Thr Val Arg Ser Val Ala Tyr Val Ala Ala
            35                  40                  45

Gly Gln Asn Ile Ser Gln Ala Glu Val Ala Ser Val Cys Lys Ala Ser
        50                  55                  60

Val Gln Ala Ser Val Asp Leu Cys Arg Val Thr Met Asn Ile Ser Thr
65                  70                  75                  80

Ser Asp Arg Ser His Leu Trp Ala Glu Ala Trp Leu Pro Arg Asn Tyr
                85                  90                  95

Thr Gly Arg Phe Val Ser Thr Gly Asn Gly Leu Ala Gly Cys Val
                    100                 105                 110

Gln Glu Thr Asp Leu Asn Phe Ala Ala Asn Phe Gly Phe Ala Thr Val
                115                 120                 125

Gly Thr Asn Gly Gly His Asp Gly Asp Thr Ala Lys Tyr Phe Leu Asn
        130                 135                 140

Asn Ser Glu Val Leu Ala Asp Phe Ala Tyr Arg Ser Val His Glu Gly
145                 150                 155                 160

Thr Val Val Gly Lys Gln Leu Thr Gln Leu Phe Tyr Asp Glu Gly Tyr
                    165                 170                 175

Asn Tyr Ser Tyr Tyr Leu Gly Cys Ser Thr Gly Arg Gln Gly Tyr
                180                 185                 190

Gln Gln Val Gln Arg Phe Pro Asp Asp Tyr Asp Gly Val Ile Ala Gly
                195                 200                 205

Ser Ala Ala Met Asn Phe Ile Asn Leu Ile Ser Trp Gly Ala Phe Leu
        210                 215                 220

Trp Lys Ala Thr Gly Leu Ala Asp Asp Pro Asp Phe Ile Ser Ala Asn
225                 230                 235                 240

Leu Trp Ser Val Ile His Gln Glu Ile Val Arg Gln Cys Asp Leu Val
                    245                 250                 255

Asp Gly Ala Leu Asp Gly Ile Ile Glu Asp Pro Asp Phe Cys Ala Pro
                260                 265                 270

Val Ile Glu Arg Leu Ile Cys Asp Gly Thr Thr Asn Gly Thr Ser Cys
        275                 280                 285

Ile Thr Gly Ala Gln Ala Ala Lys Val Asn Arg Ala Leu Ser Asp Phe
        290                 295                 300

Tyr Gly Pro Asp Gly Thr Val Tyr Tyr Pro Arg Leu Asn Tyr Gly Gly
305                 310                 315                 320

Glu Ala Asp Ser Ala Ser Leu Tyr Phe Thr Gly Ser Met Tyr Ser Arg
                325                 330                 335

Thr Glu Glu Trp Tyr Lys Tyr Val Val Tyr Asn Asp Thr Asn Trp Asn
                340                 345                 350

Ser Ser Gln Trp Thr Leu Glu Ser Ala Lys Leu Ala Leu Glu Gln Asn
        355                 360                 365

Pro Phe Asn Ile Gln Ala Phe Asp Pro Asn Ile Thr Ala Phe Arg Asp
        370                 375                 380

Arg Gly Gly Lys Leu Leu Ser Tyr His Gly Thr Gln Asp Pro Ile Ile
385                 390                 395                 400

Ser Ser Thr Asp Ser Lys Leu Tyr Tyr Arg Arg Val Ala Asn Ala Leu
                405                 410                 415

Asn Ala Ala Pro Ser Glu Leu Asp Glu Phe Tyr Arg Phe Phe Gln Ile
                420                 425                 430
```

```
Ser Gly Met Gly His Cys Gly Asp Gly Thr Gly Ala Ser Tyr Ile Gly
        435                 440                 445

Gln Gly Tyr Gly Thr Tyr Thr Ser Lys Ala Pro Gln Val Asn Leu Leu
450                 455                 460

Arg Thr Met Val Asp Trp Val Glu Asn Gly Lys Ala Pro Glu Tyr Met
465                 470                 475                 480

Pro Gly Asn Lys Leu Asn Ala Asn Gly Ser Ile Glu Tyr Met Arg Lys
            485                 490                 495

His Cys Arg Tyr Pro Lys His Asn Ile His Thr Gly Pro Gly Asn Tyr
            500                 505                 510

Thr Asp Pro Asn Ser Trp Thr Cys Val Gly Ser Thr Tyr Ser Ser Gly
            515                 520                 525

Ser Ser Ser Gly Ser Gly Ser Ser Ser Ser Ser Ser Thr Thr Thr
530                 535                 540

Lys Ala Thr Ser Thr Thr Leu Lys Thr Thr Ser Thr Thr Ser Ser Gly
545                 550                 555                 560

Ser Ser Ser Thr Ser Ala Ala Ser Thr Pro Ser Ser Thr Gly Glu Asn
            565                 570                 575

Asn Gly Phe Tyr Tyr Ser Phe Trp Thr Asp Gly Gly Asp Val Thr
            580                 585                 590

Tyr Thr Asn Gly Asp Ala Gly Ala Tyr Thr Val Glu Trp Ser Asn Val
        595                 600                 605

Gly Asn Phe Val Gly Gly Lys Gly Trp Asn Pro Gly Ser Ala Gln Asp
    610                 615                 620

Ile Thr Tyr Ser Gly Thr Phe Thr Pro Ser Gly Asn Gly Tyr Leu Ser
625                 630                 635                 640

Val Tyr Gly Trp Thr Thr Asp Pro Leu Ile Glu Tyr Tyr Ile Val Glu
            645                 650                 655

Ser Tyr Gly Asp Tyr Asn Pro Gly Ser Gly Gly Thr Tyr Lys Gly Thr
            660                 665                 670

Val Thr Ser Asp Gly Ser Val Tyr Asp Ile Tyr Thr Ala Thr Arg Thr
        675                 680                 685

Asn Ala Ala Ser Ile Gln Gly Thr Ala Thr Phe Thr Gln Tyr Trp Ser
    690                 695                 700

Val Arg Gln Asn Lys Arg Val Gly Gly Thr Val Thr Thr Ser Asn His
705                 710                 715                 720

Phe Asn Ala Trp Ala Lys Leu Gly Met Asn Leu Gly Thr His Asn Tyr
            725                 730                 735

Gln Ile Val Ala Thr Glu Gly Tyr Gln Ser Ser Gly Ser Ser Ser Ile
            740                 745                 750

Thr Val Gln Gly Ser Thr Tyr Ser Ser Gly Ser Ser Gly Ser Gly
        755                 760                 765

Ser Ser Ser Ser Ser Ser Thr Thr Thr Lys Ala Thr Ser Thr Thr
770                 775                 780

Leu Lys Thr Thr Ser Thr Thr Ser Ser Gly Ser Ser Ser Thr Ser Ala
785                 790                 795                 800

Ala Gln Ala Tyr Gly Gln Cys Gly Gly Gln Gly Trp Thr Gly Pro Thr
            805                 810                 815

Thr Cys Val Ser Gly Tyr Thr Cys Thr Tyr Glu Asn Ala Tyr Tyr Ser
            820                 825                 830

Gln Cys Leu
        835

<210> SEQ ID NO 29
```

<211> LENGTH: 1563
<212> TYPE: DNA
<213> ORGANISM: Aspergillus niger
<220> FEATURE:
<221> NAME/KEY: CDS
<222> LOCATION: (1)..(1563)
<223> OTHER INFORMATION:

<400> SEQUENCE: 29

| | | | | | | | | | | | | | | | | |
|---|---|---|---|---|---|---|---|---|---|---|---|---|---|---|---|---|
| atg | aaa | gta | gca | agt | ctc | ctc | tcc | ctg | gca | ctg | cct | ggg | gca | gcc | ctc | 48 |
| Met | Lys | Val | Ala | Ser | Leu | Leu | Ser | Leu | Ala | Leu | Pro | Gly | Ala | Ala | Leu | |
| 1 | | | | 5 | | | | | 10 | | | | | 15 | | |
| gct | gcg | acc | gac | ccc | ttc | cag | tcg | cgg | tgc | aat | gaa | ttc | cag | aac | aag | 96 |
| Ala | Ala | Thr | Asp | Pro | Phe | Gln | Ser | Arg | Cys | Asn | Glu | Phe | Gln | Asn | Lys | |
| | | | 20 | | | | | 25 | | | | | 30 | | | |
| atc | gac | atc | gcc | aat | gtc | acc | gtc | aga | tcg | gtc | gca | tac | gtt | gct | gct | 144 |
| Ile | Asp | Ile | Ala | Asn | Val | Thr | Val | Arg | Ser | Val | Ala | Tyr | Val | Ala | Ala | |
| | | 35 | | | | | 40 | | | | | 45 | | | | |
| gga | cag | aac | atc | tcc | caa | gcg | gag | gtc | gcc | tcc | gtg | tgt | aaa | gca | tcg | 192 |
| Gly | Gln | Asn | Ile | Ser | Gln | Ala | Glu | Val | Ala | Ser | Val | Cys | Lys | Ala | Ser | |
| | 50 | | | | | 55 | | | | | 60 | | | | | |
| gtt | caa | gcc | agt | gtc | gac | ctg | tgc | cgg | gta | acc | atg | aac | atc | tcg | acg | 240 |
| Val | Gln | Ala | Ser | Val | Asp | Leu | Cys | Arg | Val | Thr | Met | Asn | Ile | Ser | Thr | |
| 65 | | | | | 70 | | | | | 75 | | | | | 80 | |
| tcg | gat | cgc | agc | cat | ctg | tgg | gct | gag | gcc | tgg | ctc | cca | aga | aat | tat | 288 |
| Ser | Asp | Arg | Ser | His | Leu | Trp | Ala | Glu | Ala | Trp | Leu | Pro | Arg | Asn | Tyr | |
| | | | | 85 | | | | | 90 | | | | | 95 | | |
| acc | ggt | cgc | ttc | gtg | agc | acg | ggg | aat | gga | ggt | cta | gcc | ggc | tgt | gtc | 336 |
| Thr | Gly | Arg | Phe | Val | Ser | Thr | Gly | Asn | Gly | Gly | Leu | Ala | Gly | Cys | Val | |
| | | | 100 | | | | | 105 | | | | | 110 | | | |
| caa | gaa | acg | gac | ctc | aac | ttt | gca | gcc | aac | ttt | ggt | ttc | gct | acc | gtg | 384 |
| Gln | Glu | Thr | Asp | Leu | Asn | Phe | Ala | Ala | Asn | Phe | Gly | Phe | Ala | Thr | Val | |
| | | 115 | | | | | 120 | | | | | 125 | | | | |
| ggc | acc | aac | ggt | gga | cat | gac | ggg | gac | acg | gcc | aaa | tac | ttc | ctc | aac | 432 |
| Gly | Thr | Asn | Gly | Gly | His | Asp | Gly | Asp | Thr | Ala | Lys | Tyr | Phe | Leu | Asn | |
| | 130 | | | | | 135 | | | | | 140 | | | | | |
| aac | tcg | gag | gtt | ctg | gcc | gat | ttt | gcc | tat | cgc | tca | gtg | cac | gaa | ggg | 480 |
| Asn | Ser | Glu | Val | Leu | Ala | Asp | Phe | Ala | Tyr | Arg | Ser | Val | His | Glu | Gly | |
| 145 | | | | | 150 | | | | | 155 | | | | | 160 | |
| acc | gtg | gtg | ggt | aag | caa | cta | act | caa | ttg | ttt | tat | gac | gag | gga | tac | 528 |
| Thr | Val | Val | Gly | Lys | Gln | Leu | Thr | Gln | Leu | Phe | Tyr | Asp | Glu | Gly | Tyr | |
| | | | 165 | | | | | 170 | | | | | 175 | | | |
| aac | tac | tcc | tac | tat | ttg | ggt | tgc | tcc | acc | gga | ggc | cgc | caa | ggc | tac | 576 |
| Asn | Tyr | Ser | Tyr | Tyr | Leu | Gly | Cys | Ser | Thr | Gly | Gly | Arg | Gln | Gly | Tyr | |
| | | 180 | | | | | 185 | | | | | 190 | | | | |
| cag | caa | gtc | caa | cgg | ttt | ccc | gac | gac | tat | gac | gga | gtg | att | gcg | ggc | 624 |
| Gln | Gln | Val | Gln | Arg | Phe | Pro | Asp | Asp | Tyr | Asp | Gly | Val | Ile | Ala | Gly | |
| | 195 | | | | | 200 | | | | | 205 | | | | | |
| tcc | gca | gcg | atg | aac | ttt | atc | aac | ctg | atc | tcc | tgg | ggg | gcc | ttc | ttg | 672 |
| Ser | Ala | Ala | Met | Asn | Phe | Ile | Asn | Leu | Ile | Ser | Trp | Gly | Ala | Phe | Leu | |
| 210 | | | | | 215 | | | | | 220 | | | | | | |
| tgg | aag | gcg | acg | ggg | tta | gcg | gat | gat | cca | gac | ttt | atc | tct | gca | aac | 720 |
| Trp | Lys | Ala | Thr | Gly | Leu | Ala | Asp | Asp | Pro | Asp | Phe | Ile | Ser | Ala | Asn | |
| 225 | | | | 230 | | | | | 235 | | | | | 240 | | |
| ctg | tgg | tcc | gta | atc | cac | cag | gag | att | gtt | cgt | cag | tgc | gac | ctg | gtc | 768 |
| Leu | Trp | Ser | Val | Ile | His | Gln | Glu | Ile | Val | Arg | Gln | Cys | Asp | Leu | Val | |
| | | | | 245 | | | | | 250 | | | | | 255 | | |
| gat | ggg | gct | ctg | gat | gga | atc | atc | gaa | gac | cct | gat | ttc | tgt | gct | cca | 816 |
| Asp | Gly | Ala | Leu | Asp | Gly | Ile | Ile | Glu | Asp | Pro | Asp | Phe | Cys | Ala | Pro | |
| | | | 260 | | | | | 265 | | | | | 270 | | | |
| gtc | atc | gag | cgc | ttg | atc | tgc | gac | ggg | act | acc | aac | ggc | acc | tct | tgt | 864 |
| Val | Ile | Glu | Arg | Leu | Ile | Cys | Asp | Gly | Thr | Thr | Asn | Gly | Thr | Ser | Cys | |

```
              275                 280                 285
atc acg gga gcc cag gca gca aag gtc aac cgg gcc ttg agt gac ttc    912
Ile Thr Gly Ala Gln Ala Ala Lys Val Asn Arg Ala Leu Ser Asp Phe
    290                 295                 300 tat ggc ccc gac ggg aca gtg tac tac ccg cgc ctg aac tat ggg ggt    960
Tyr Gly Pro Asp Gly Thr Val Tyr Tyr Pro Arg Leu Asn Tyr Gly Gly
305                 310                 315                 320 gag gcc gac tcg gct tcc ctg tac ttc acg ggg tcg atg tac agc cgt   1008
Glu Ala Asp Ser Ala Ser Leu Tyr Phe Thr Gly Ser Met Tyr Ser Arg
                325                 330                 335 acg gag gaa tgg tac aaa tat gtg gtc tat aac gac acc aac tgg aac   1056
Thr Glu Glu Trp Tyr Lys Tyr Val Val Tyr Asn Asp Thr Asn Trp Asn
        340                 345                 350 tcc agc cag tgg acg ctg gag agt gcc aag ctg gcc ctg gag cag aat   1104
Ser Ser Gln Trp Thr Leu Glu Ser Ala Lys Leu Ala Leu Glu Gln Asn
    355                 360                 365 ccg ttc aat atc cag gcg ttt gat ccc aac atc acg gcc ttc cgg gac   1152
Pro Phe Asn Ile Gln Ala Phe Asp Pro Asn Ile Thr Ala Phe Arg Asp
370                 375                 380 cgg ggt ggc aag ctg ctg tcc tac cac ggc acg cag gat ccc att atc   1200
Arg Gly Gly Lys Leu Leu Ser Tyr His Gly Thr Gln Asp Pro Ile Ile
385                 390                 395                 400 agc tcc acg gat agc aag ctc tac tac cga cgg gta gcg aat gcc ctg   1248
Ser Ser Thr Asp Ser Lys Leu Tyr Tyr Arg Arg Val Ala Asn Ala Leu
                405                 410                 415 aat gcc gcg ccg tcc gag cta gat gag ttc tat cgg ttc ttc cag atc   1296
Asn Ala Ala Pro Ser Glu Leu Asp Glu Phe Tyr Arg Phe Phe Gln Ile
        420                 425                 430 tcc ggc atg ggc cac tgt ggc gat ggc acg gga gca tcg tac atc ggc   1344
Ser Gly Met Gly His Cys Gly Asp Gly Thr Gly Ala Ser Tyr Ile Gly
    435                 440                 445 cag gga tat ggc acg tac acc tcc aag gcg ccc caa gtc aac ctg ctg   1392
Gln Gly Tyr Gly Thr Tyr Thr Ser Lys Ala Pro Gln Val Asn Leu Leu
450                 455                 460 cgc acg atg gtg gac tgg gtg gaa aac gga aag gcg ccc gag tat atg   1440
Arg Thr Met Val Asp Trp Val Glu Asn Gly Lys Ala Pro Glu Tyr Met
465                 470                 475                 480 ccg ggc aac aag ctc aac gcg aac ggg tca att gag tac atg cgc aag   1488
Pro Gly Asn Lys Leu Asn Ala Asn Gly Ser Ile Glu Tyr Met Arg Lys
                485                 490                 495 cac tgc cgg tat ccg aag cat aac att cac acg ggg ccg ggt aac tac   1536
His Cys Arg Tyr Pro Lys His Asn Ile His Thr Gly Pro Gly Asn Tyr
        500                 505                 510 acc gat cct aac tcc tgg act tgc gta                                1563
Thr Asp Pro Asn Ser Trp Thr Cys Val
    515                 520

<210> SEQ ID NO 30
<211> LENGTH: 521
<212> TYPE: PRT
<213> ORGANISM: Aspergillus niger

<400> SEQUENCE: 30

Met Lys Val Ala Ser Leu Leu Ser Leu Ala Leu Pro Gly Ala Ala Leu
1               5                   10                  15

Ala Ala Thr Asp Pro Phe Gln Ser Arg Cys Asn Glu Phe Gln Asn Lys
            20                  25                  30

Ile Asp Ile Ala Asn Val Thr Val Arg Ser Val Ala Tyr Val Ala Ala
        35                  40                  45

Gly Gln Asn Ile Ser Gln Ala Glu Val Ala Ser Val Cys Lys Ala Ser
```

```
            50                  55                  60
Val Gln Ala Ser Val Asp Leu Cys Arg Val Thr Met Asn Ile Ser Thr
65                  70                  75                  80

Ser Asp Arg Ser His Leu Trp Ala Glu Ala Trp Leu Pro Arg Asn Tyr
                85                  90                  95

Thr Gly Arg Phe Val Ser Thr Gly Asn Gly Leu Ala Gly Cys Val
            100                 105                 110

Gln Glu Thr Asp Leu Asn Phe Ala Ala Asn Phe Gly Phe Ala Thr Val
                115                 120                 125

Gly Thr Asn Gly Gly His Asp Gly Asp Thr Ala Lys Tyr Phe Leu Asn
130                 135                 140

Asn Ser Glu Val Leu Ala Asp Phe Ala Tyr Arg Ser Val His Glu Gly
145                 150                 155                 160

Thr Val Val Gly Lys Gln Leu Thr Gln Leu Phe Tyr Asp Glu Gly Tyr
                165                 170                 175

Asn Tyr Ser Tyr Tyr Leu Gly Cys Ser Thr Gly Arg Gln Gly Tyr
            180                 185                 190

Gln Gln Val Gln Arg Phe Pro Asp Asp Tyr Asp Gly Val Ile Ala Gly
                195                 200                 205

Ser Ala Ala Met Asn Phe Ile Asn Leu Ile Ser Trp Gly Ala Phe Leu
210                 215                 220

Trp Lys Ala Thr Gly Leu Ala Asp Pro Asp Phe Ile Ser Ala Asn
225                 230                 235                 240

Leu Trp Ser Val Ile His Gln Glu Ile Val Arg Gln Cys Asp Leu Val
            245                 250                 255

Asp Gly Ala Leu Asp Gly Ile Ile Glu Asp Pro Asp Phe Cys Ala Pro
                260                 265                 270

Val Ile Glu Arg Leu Ile Cys Asp Gly Thr Thr Asn Gly Thr Ser Cys
            275                 280                 285

Ile Thr Gly Ala Gln Ala Ala Lys Val Asn Arg Ala Leu Ser Asp Phe
            290                 295                 300

Tyr Gly Pro Asp Gly Thr Val Tyr Tyr Pro Arg Leu Asn Tyr Gly Gly
305                 310                 315                 320

Glu Ala Asp Ser Ala Ser Leu Tyr Phe Thr Gly Ser Met Tyr Ser Arg
                325                 330                 335

Thr Glu Glu Trp Tyr Lys Tyr Val Val Tyr Asn Asp Thr Asn Trp Asn
                340                 345                 350

Ser Ser Gln Trp Thr Leu Glu Ser Ala Lys Leu Ala Leu Glu Gln Asn
            355                 360                 365

Pro Phe Asn Ile Gln Ala Phe Asp Pro Asn Ile Thr Ala Phe Arg Asp
370                 375                 380

Arg Gly Gly Lys Leu Leu Ser Tyr His Gly Thr Gln Asp Pro Ile Ile
385                 390                 395                 400

Ser Ser Thr Asp Ser Lys Leu Tyr Tyr Arg Arg Val Ala Asn Ala Leu
                405                 410                 415

Asn Ala Ala Pro Ser Glu Leu Asp Glu Phe Tyr Arg Phe Phe Gln Ile
            420                 425                 430

Ser Gly Met Gly His Cys Gly Asp Gly Thr Gly Ala Ser Tyr Ile Gly
            435                 440                 445

Gln Gly Tyr Gly Thr Tyr Thr Ser Lys Ala Pro Gln Val Asn Leu Leu
            450                 455                 460

Arg Thr Met Val Asp Trp Val Glu Asn Gly Lys Ala Pro Glu Tyr Met
465                 470                 475                 480
```

```
Pro Gly Asn Lys Leu Asn Ala Asn Gly Ser Ile Glu Tyr Met Arg Lys
            485                 490                 495

His Cys Arg Tyr Pro Lys His Asn Ile His Thr Gly Pro Gly Asn Tyr
            500                 505                 510

Thr Asp Pro Asn Ser Trp Thr Cys Val
            515             520
```